United States Patent [19]
Narula et al.

[11] Patent Number: 5,240,907
[45] Date of Patent: Aug. 31, 1993

[54] SUBSTITUTED CYCLOPENTYL OXABICYCLOOCTANES, CYCLOPENYL VINYL PYRANS, CYCLOPENTYLFORMYLCYCLOHEXENES AND CYCLOPENTYLHYDROXYMETHYL CYCLOHEXENES, PROCESSES FOR PREPARING SAME AND ORGANOLEPTIC USES THEREOF

[75] Inventors: Anubhav P. S. Narula, Hazlet; John J. De Virgilio, Red Bank, both of N.J.; Franc T. Schiet, New York, N.Y.; Charles E. J. Beck, Summit, N.J.; Charles J. Vinals, Weekhawken, N.J.; Marie R. Hanna, Keyport, N.J.

[73] Assignee: International Flavors & Fragrances Inc., New York, N.Y.

[21] Appl. No.: 966,093

[22] Filed: Oct. 23, 1992

[51] Int. Cl.$^5$ .................................. A61K 7/46
[52] U.S. Cl. .......................... 512/8; 512/12; 512/13; 512/22; 512/24; 568/446; 568/816; 549/397; 549/356; 549/463
[58] Field of Search ............... 512/8, 22, 13, 12, 24; 568/446, 816; 549/397, 356, 463

[56] References Cited
U.S. PATENT DOCUMENTS

| | | | |
|---|---|---|---|
| 4,269,862 | 5/1981 | Spricker | 426/536 |
| 4,547,315 | 10/1985 | Rohr et al. | 512/68 |
| 5,081,262 | 1/1992 | Narula et al. | 549/355 |
| 5,128,317 | 7/1992 | Narula et al. | 512/13 |

Primary Examiner—James H. Reamer
Attorney, Agent, or Firm—Arthur L. Liberman

[57] ABSTRACT

Described are substituted cyclopentyl oxabicyclooctanes, cyclopentyl vinyl pyrans, cyclopentylformylcyclohexenes and cyclopentylhydroxymethyl cyclohexenes having the generic structures:

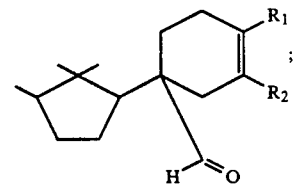
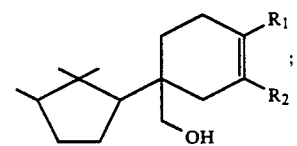
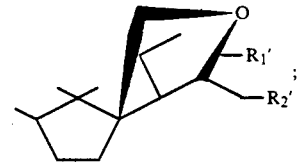
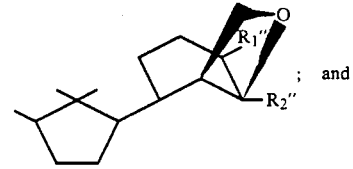
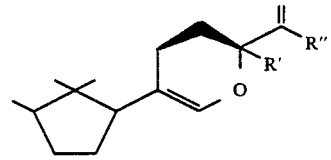

wherein $R_1$, $R_2$, R', R", $R_1'$, $R_2'$, $R_1''$ and $R_2''$ represent hydrogen or methyl with the provisos that:
(i) $R_1$ and $R_2$ are not both methyl;
(ii) R' and R" are not both methyl;
(iii) when $R_1'$ is methyl, $R_2'$ is hydrogen; and
(iv) when $R_2''$ is methyl, then $R_1''$ is hydrogen, processes for preparing same and uses thereof in augmenting or enhancing the aroma of perfume compositions, colognes and perfumed articles, e.g., solid or liquid, anionic, cationic, nonionic or zwitterionic detergents, cosmetic preparations, fabric softener compositions, fabric softener articles, hair preparations and perfumed polymers.

17 Claims, 47 Drawings

NMR SPECTRUM FOR EXAMPLE I(a).

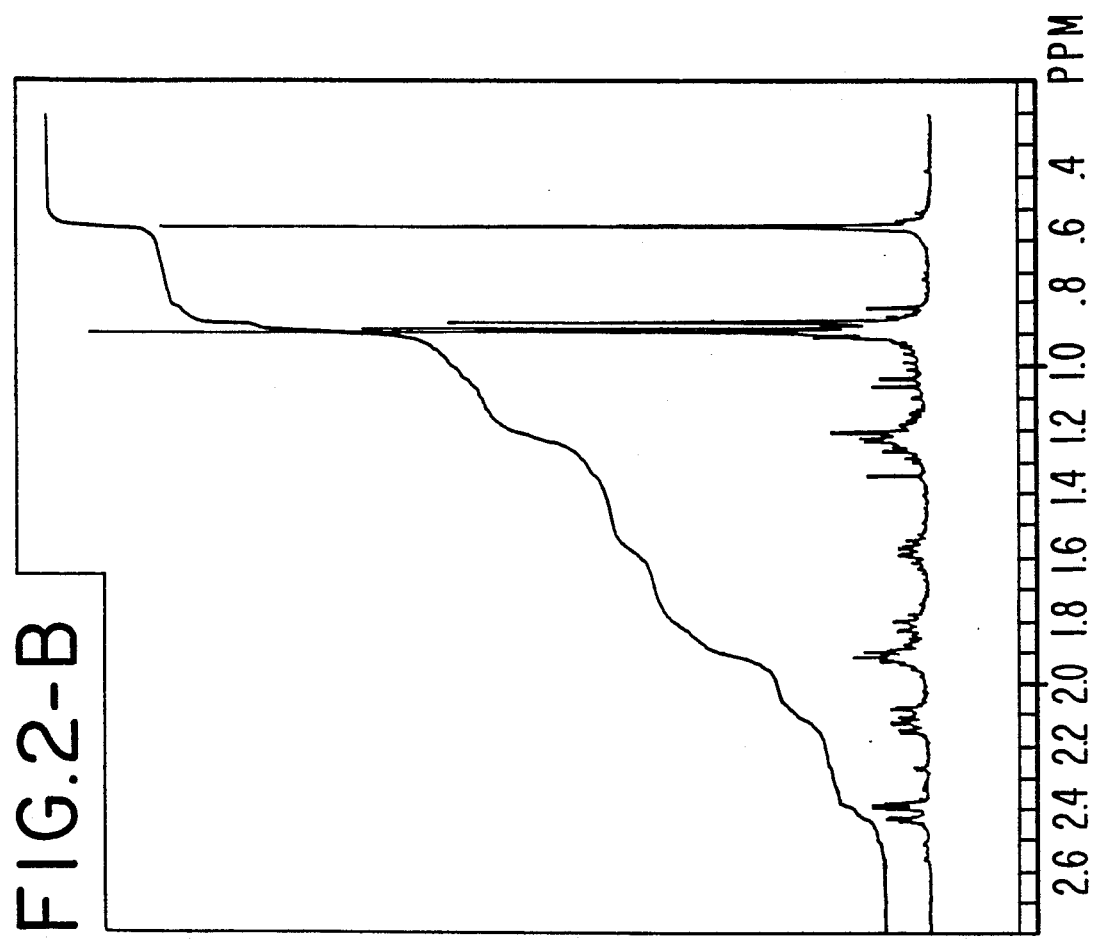
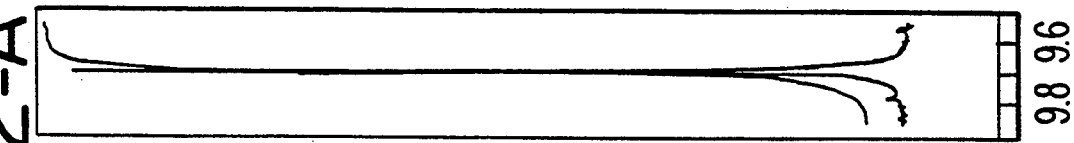

I.R. SPECTRUM FOR EXAMPLE I(a).

GC PROFILE FOR EXAMPLE I(b).

NMR SPECTRUM FOR EXAMPLE I(b).

FIG.5-A
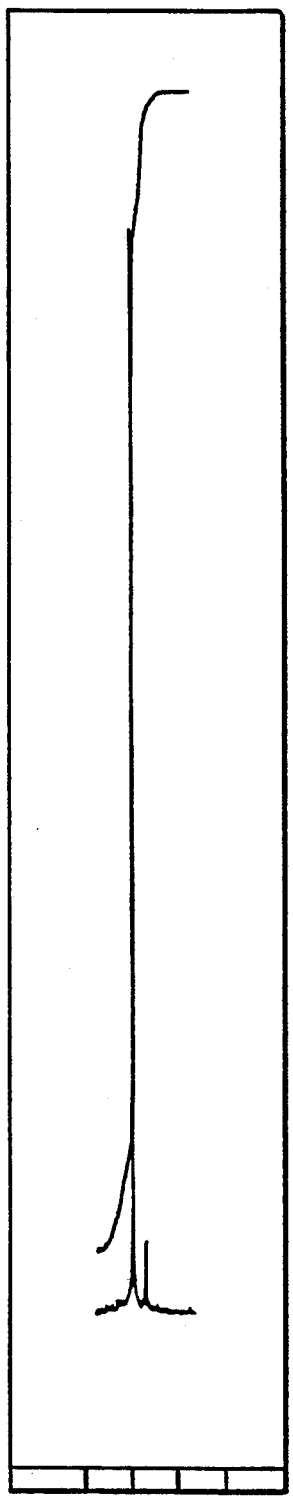
9.5
PPM
FIG.5-B
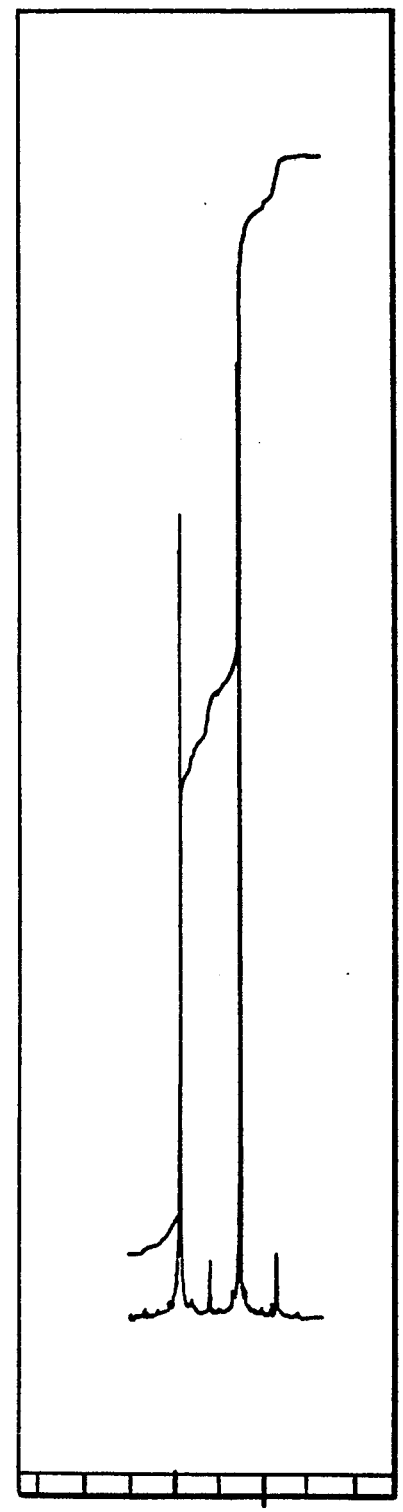
6.2  6.0
PPM

FIG.5-C
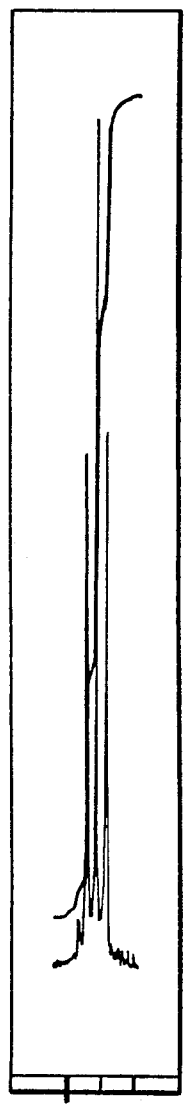
3.0  2.8
PPM
FIG.5-D
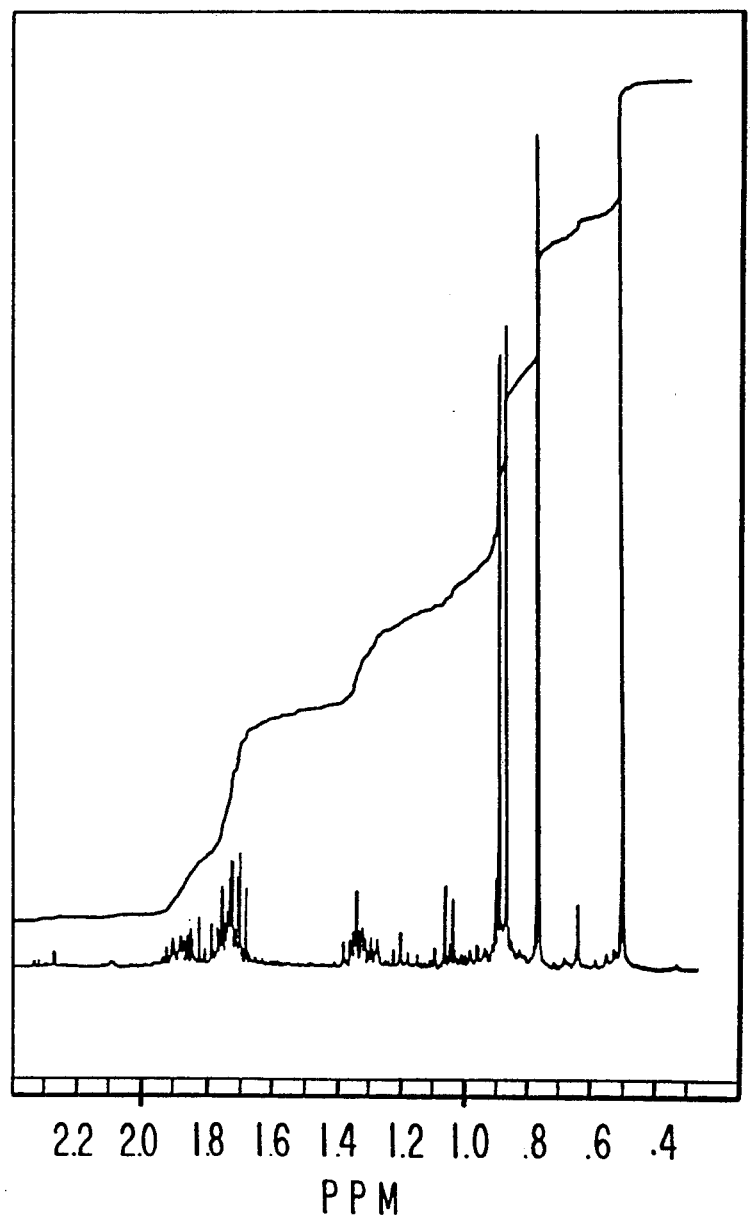
2.2  2.0  1.8  1.6  1.4  1.2  1.0  .8  .6  .4
PPM

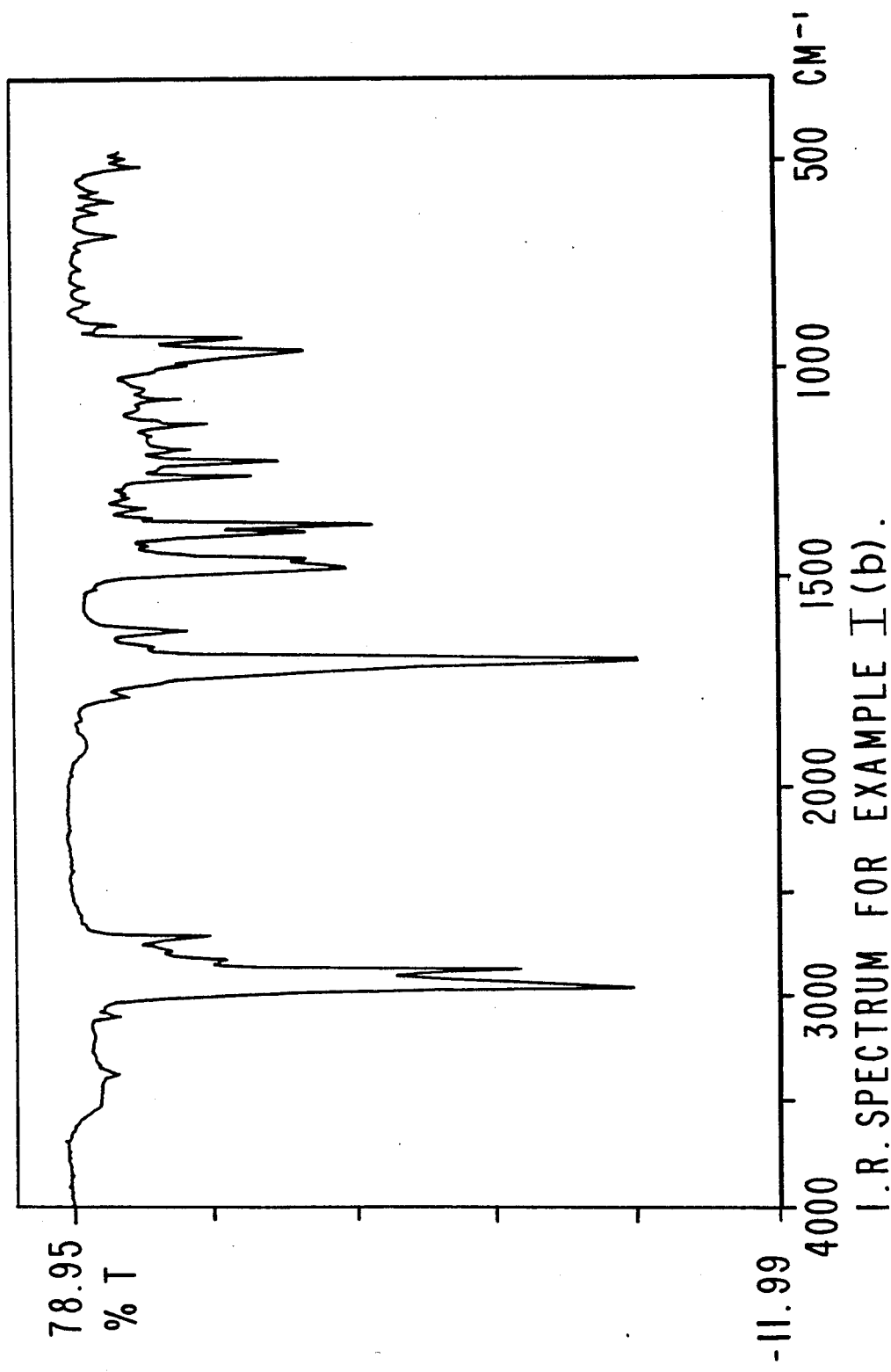

G C PROFILE FOR EXAMPLE I(c).

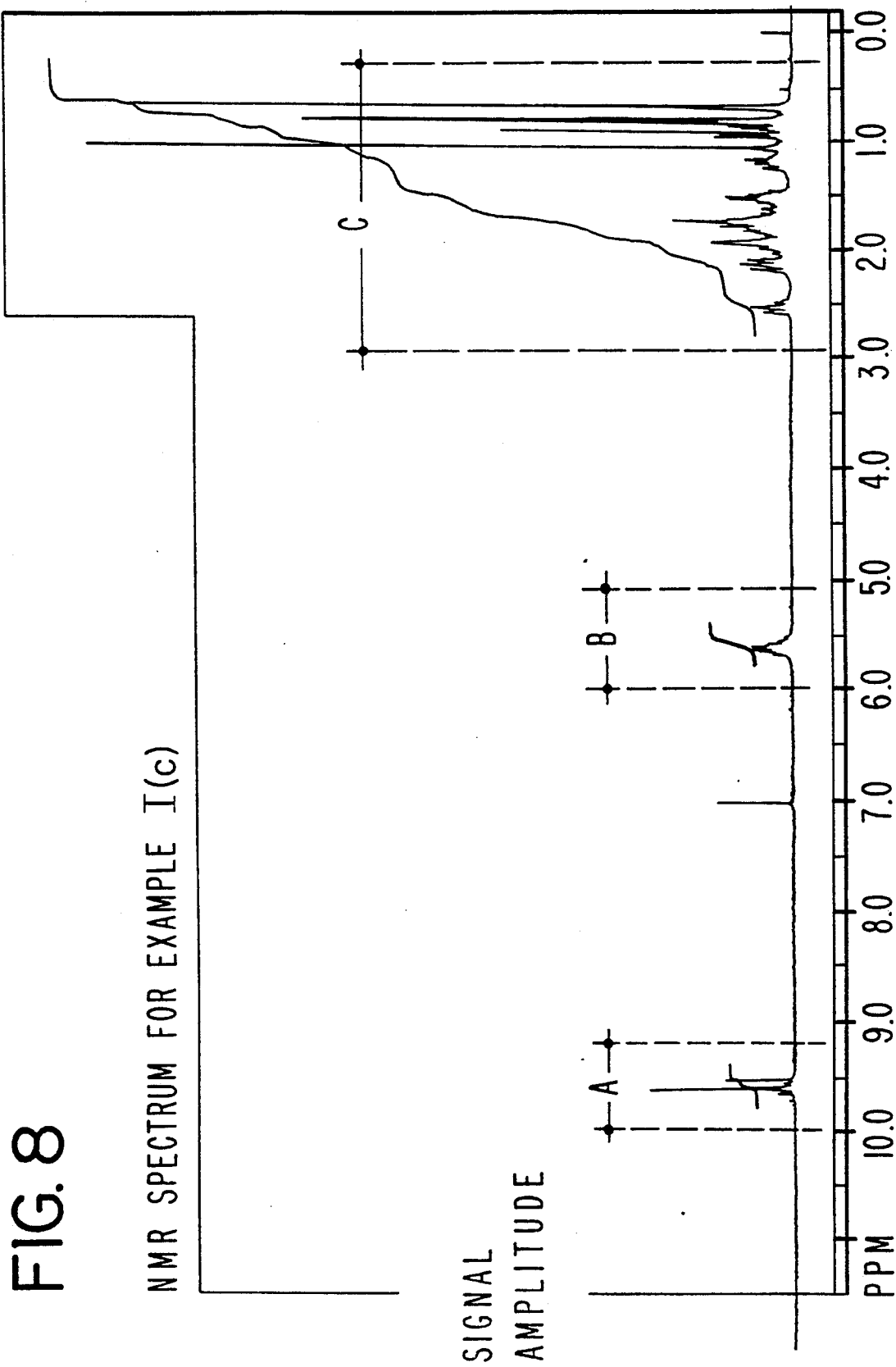

FIG. 8-A
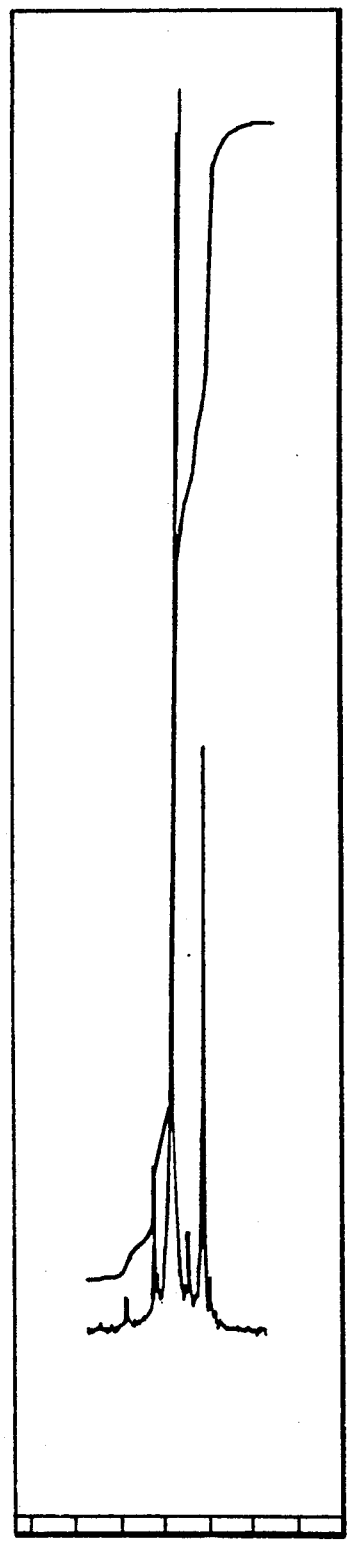
9.6
PPM
FIG. 8-B
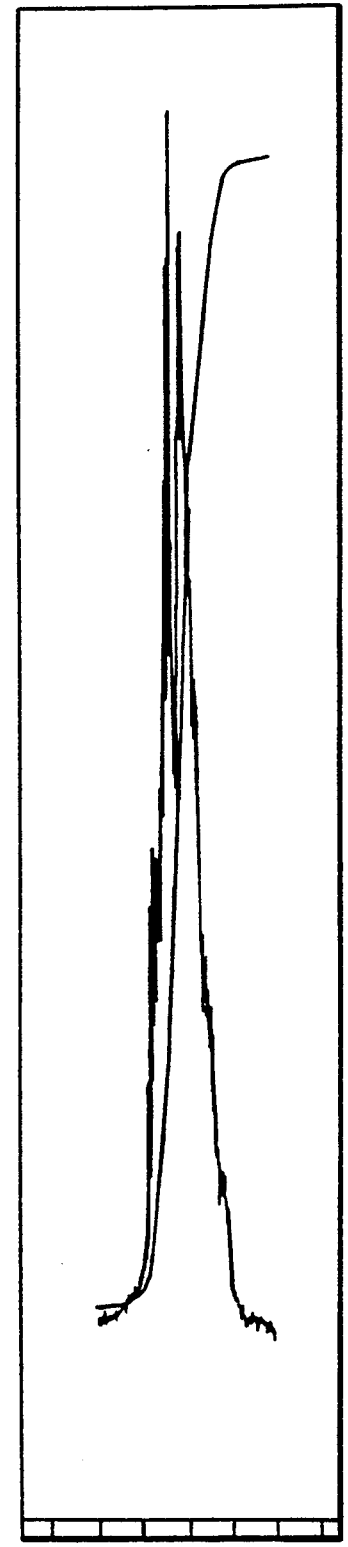
5.6
PPM

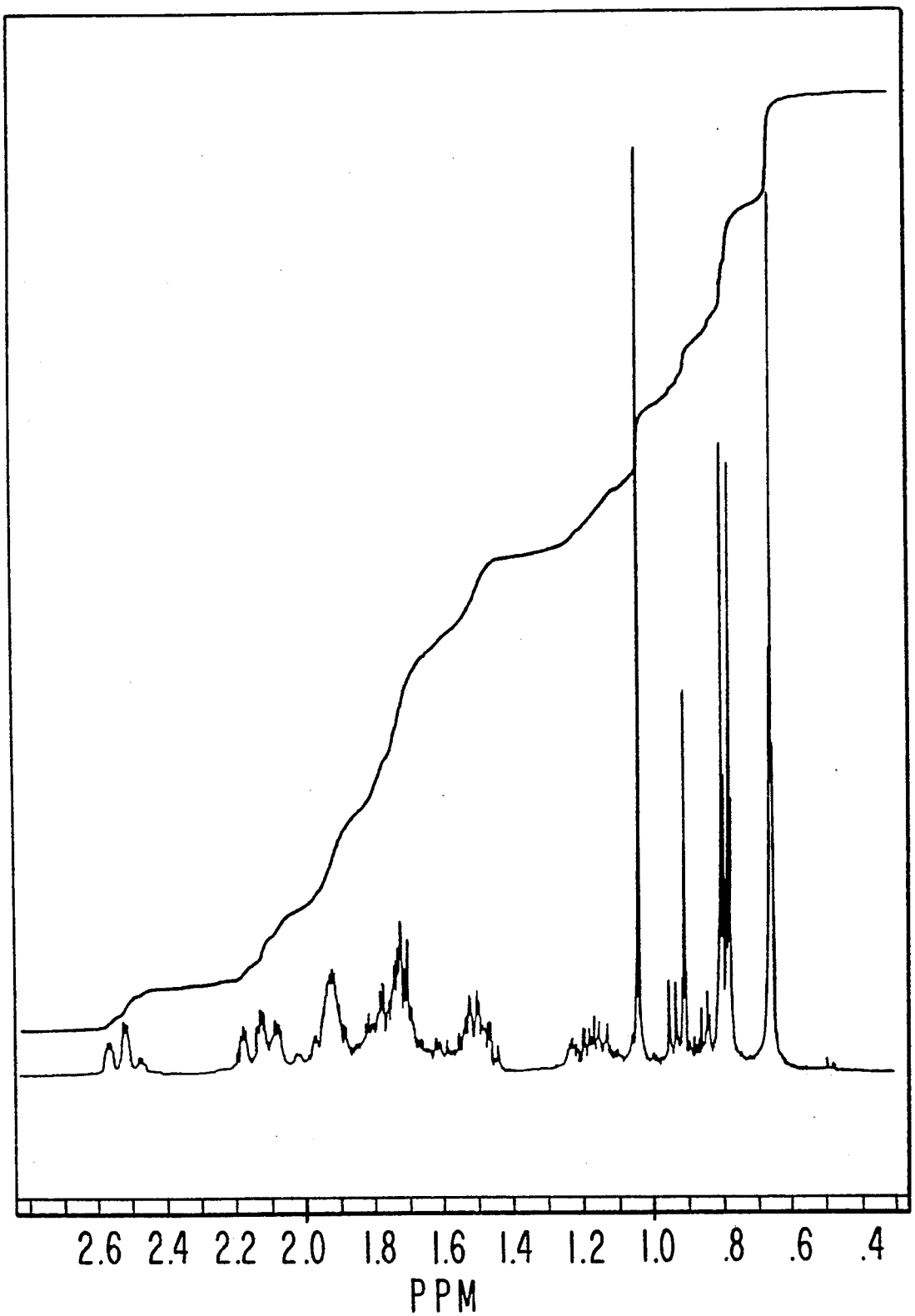
FIG.8-C

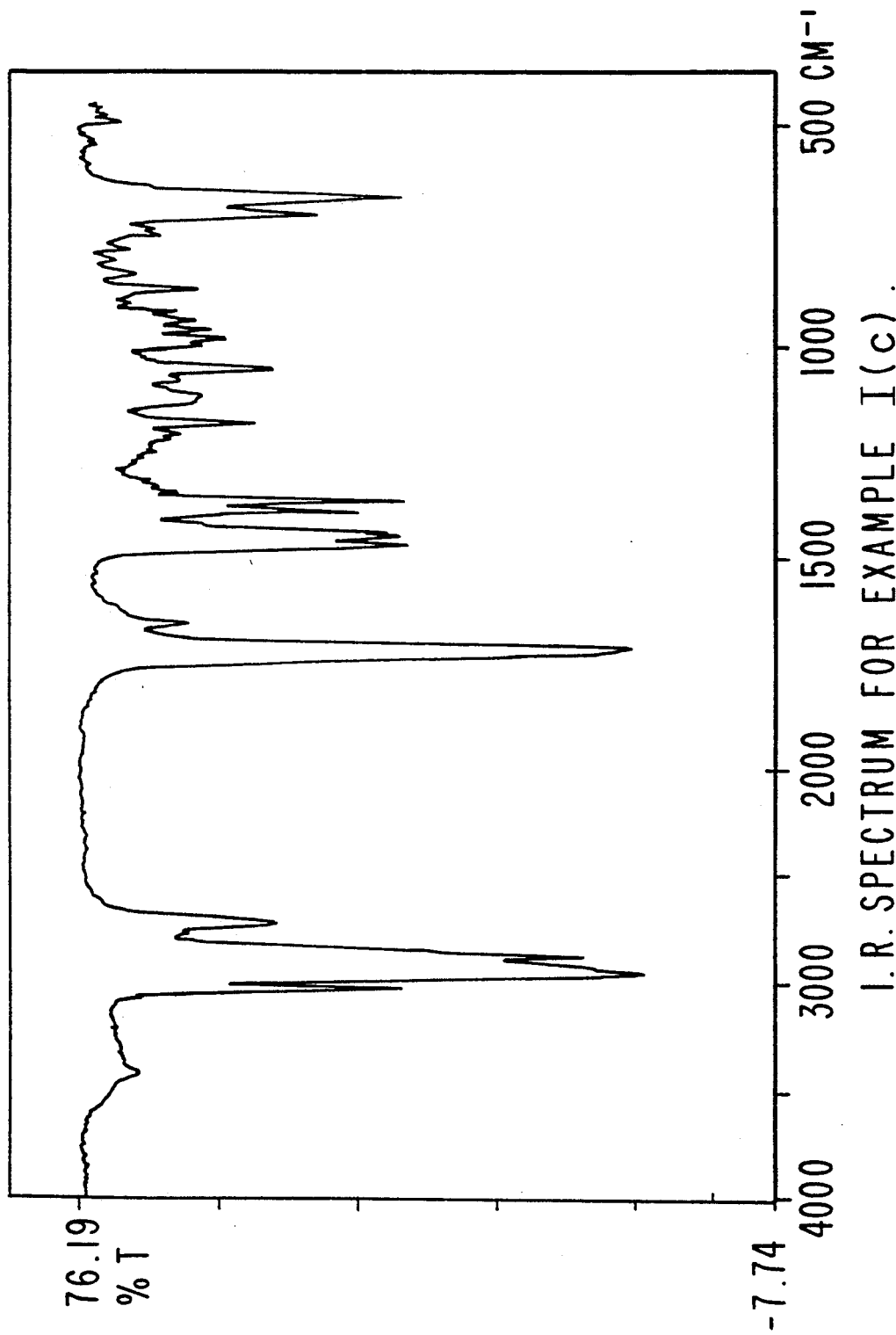

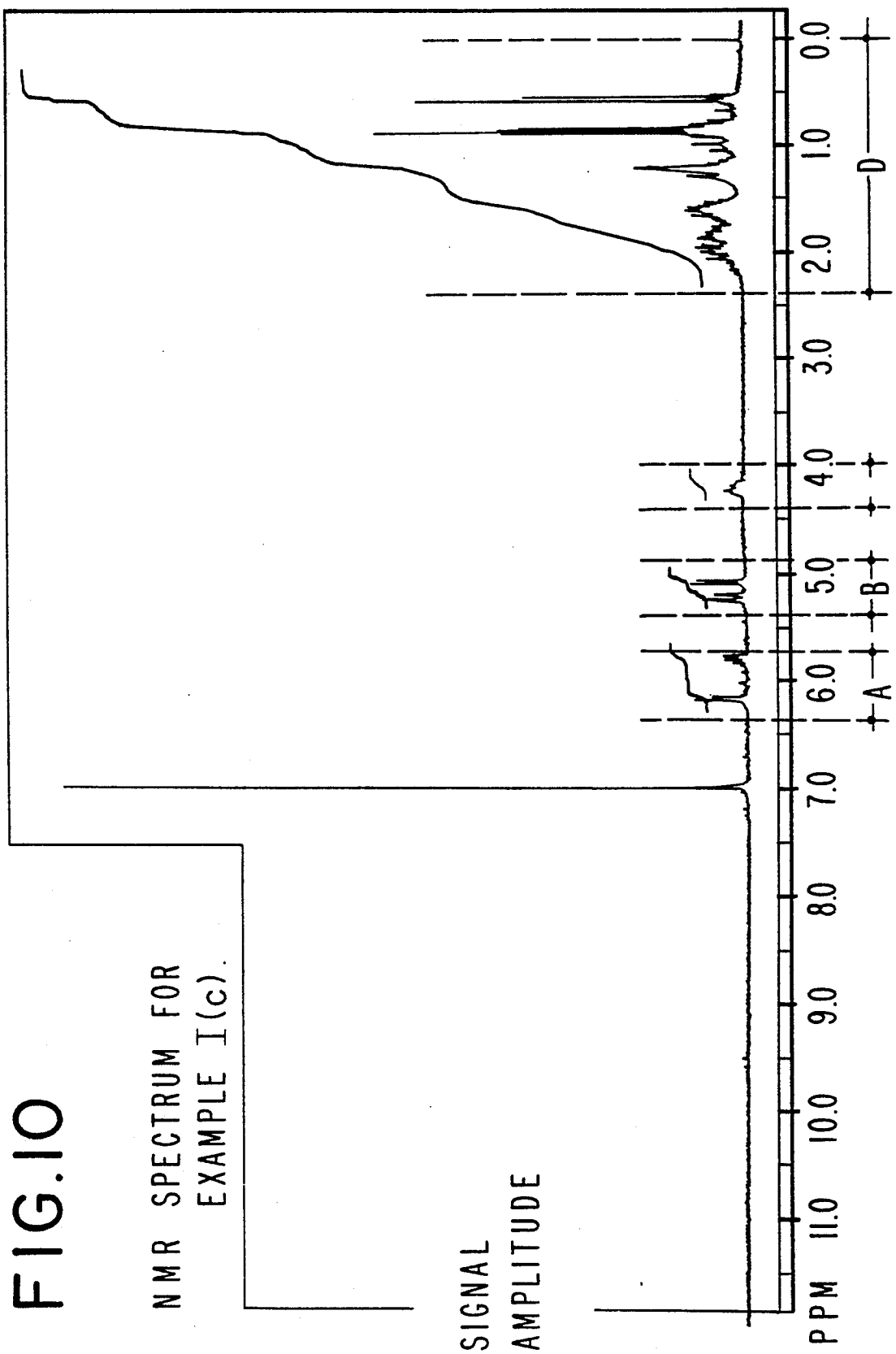

FIG.10-A
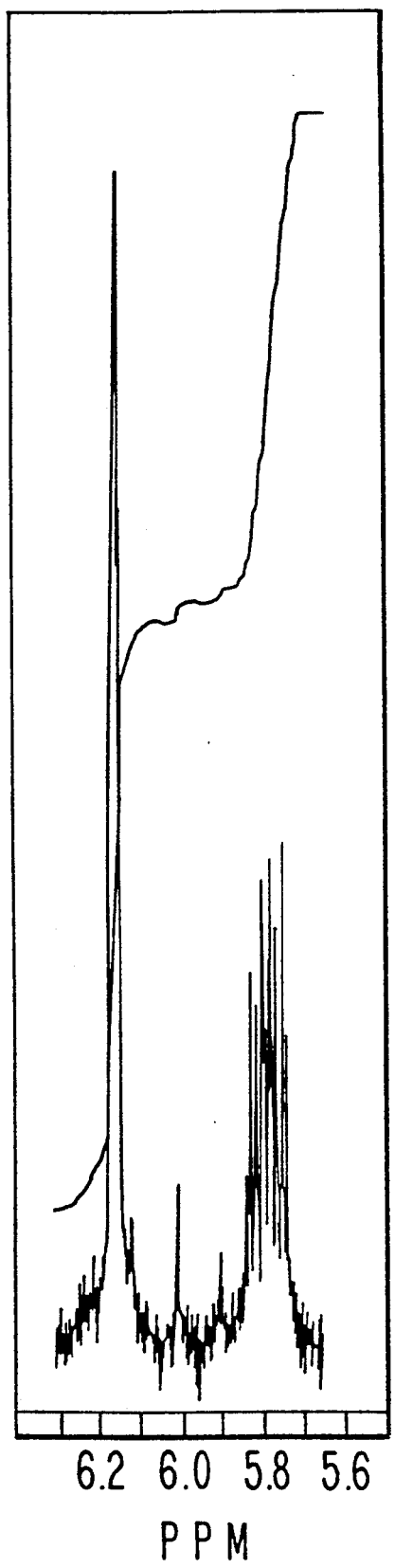
FIG.10-B
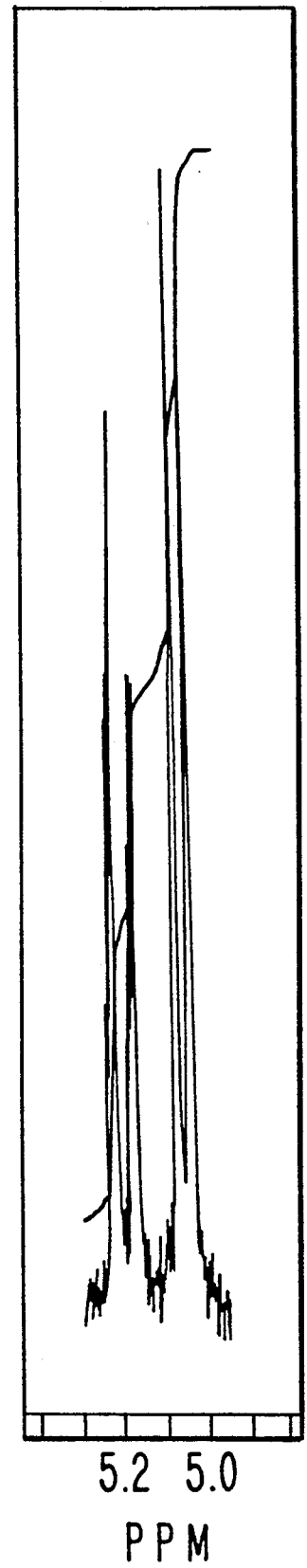

FIG.10-C
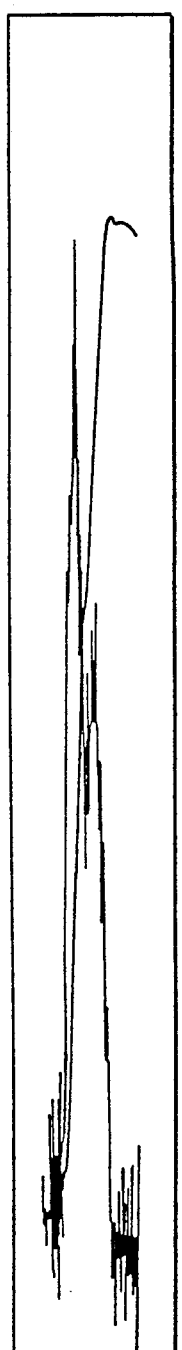
4.2
PPM
FIG.10-D
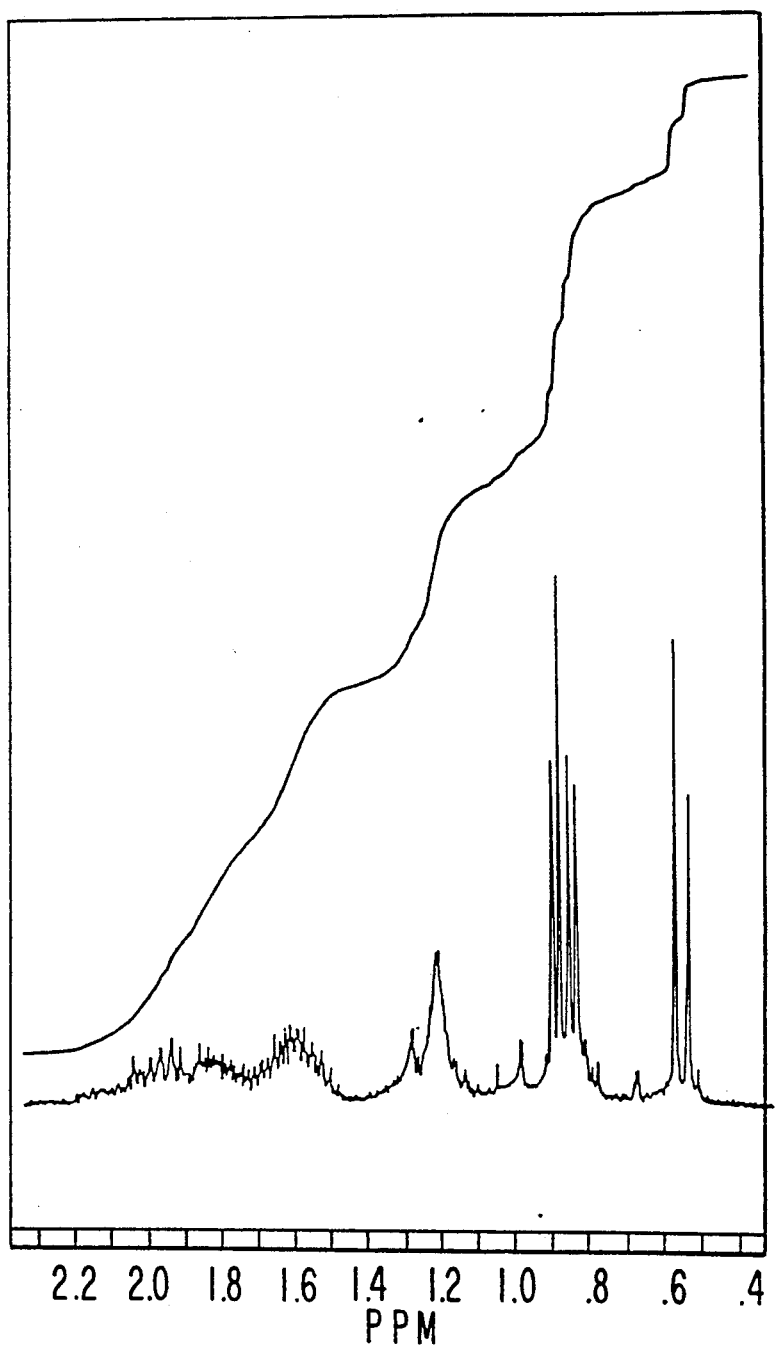
2.2  2.0  1.8  1.6  1.4  1.2  1.0  .8  .6  .4
PPM GC PROFILE FOR EXAMPLE I(d).

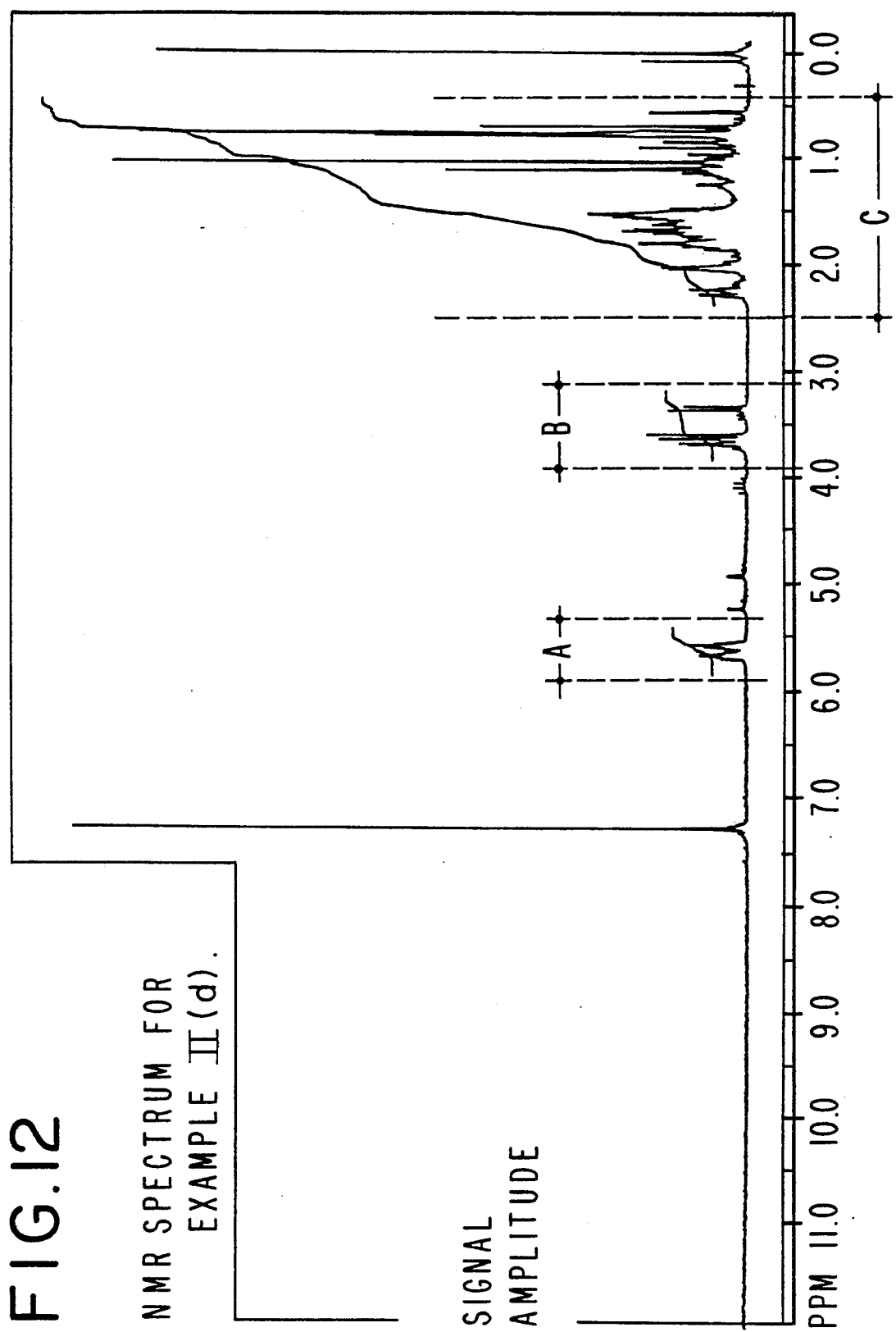

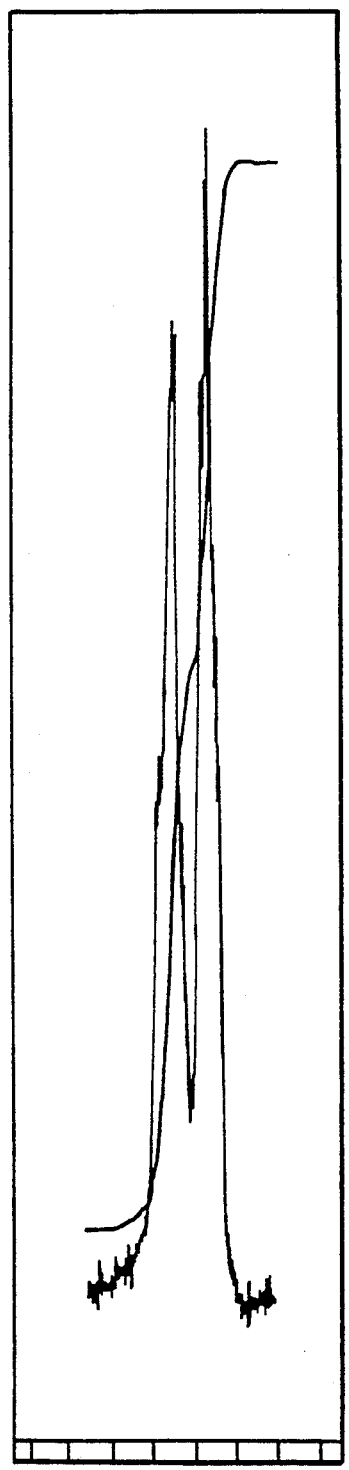# FIG.12-A
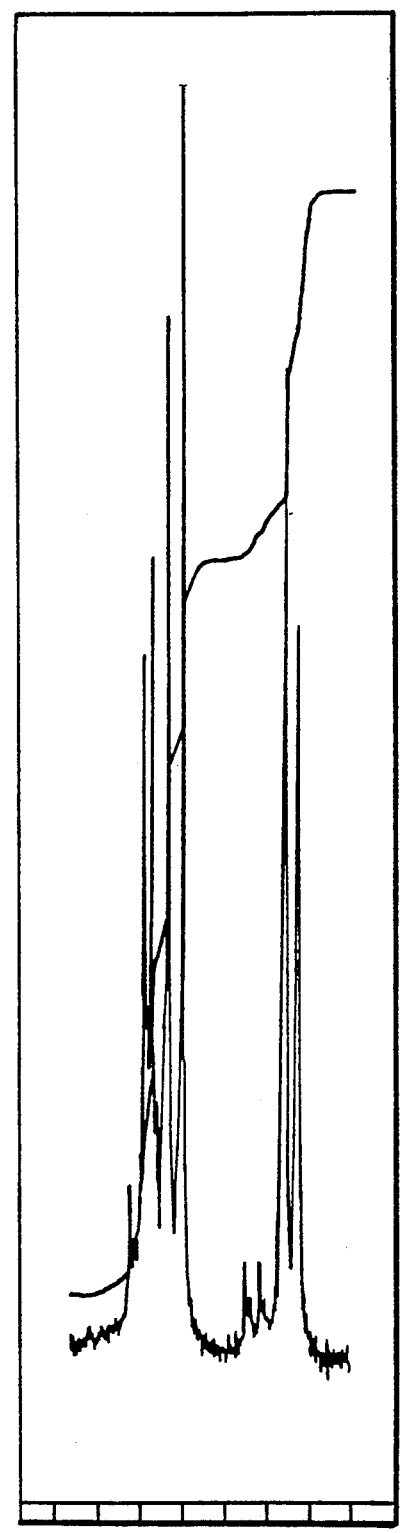# FIG.12-B

FIG. 12-C
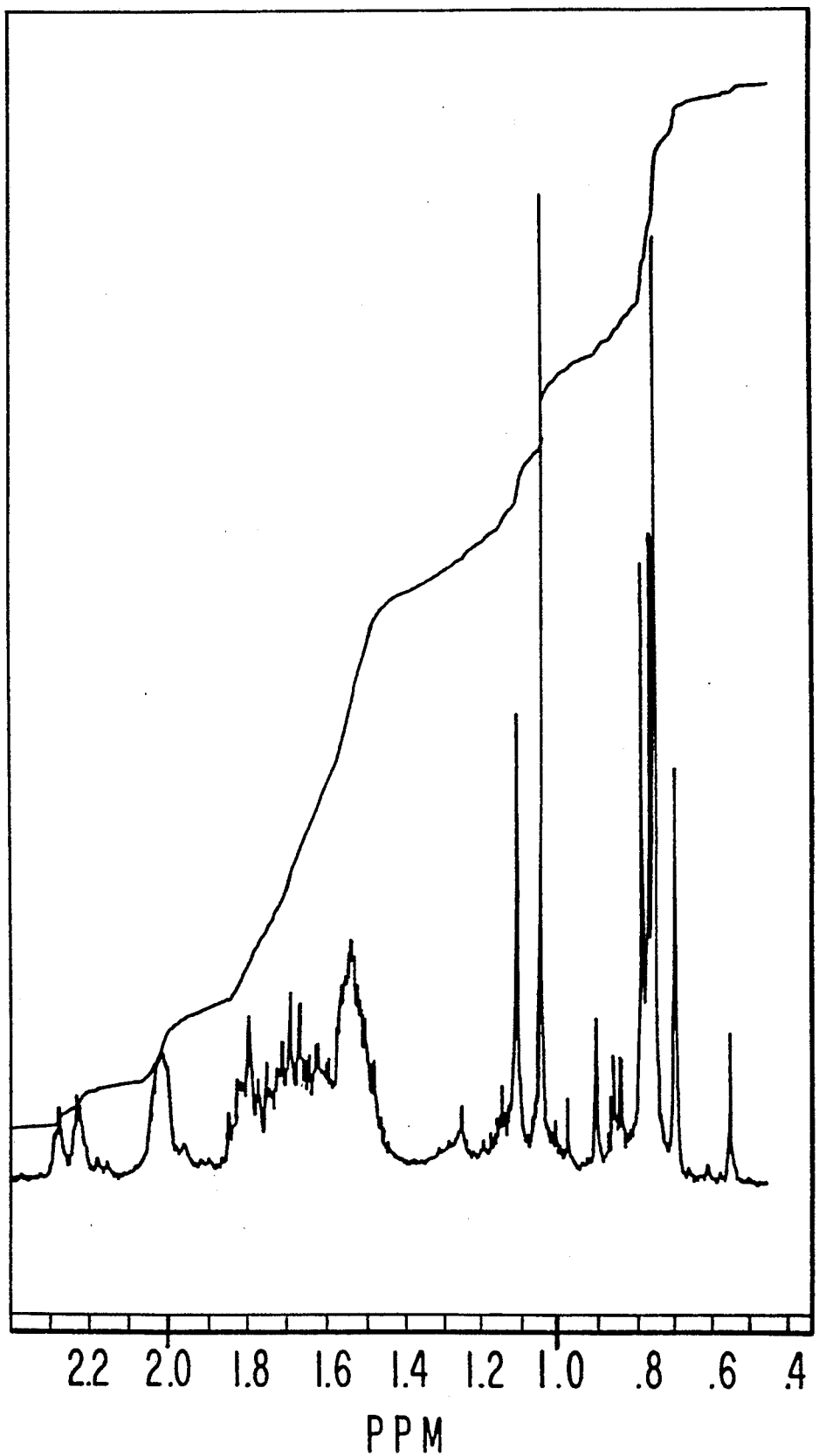

IR SPECTRUM FOR EXAMPLE I(d).

GC PROFILE FOR EXAMPLE I(e).

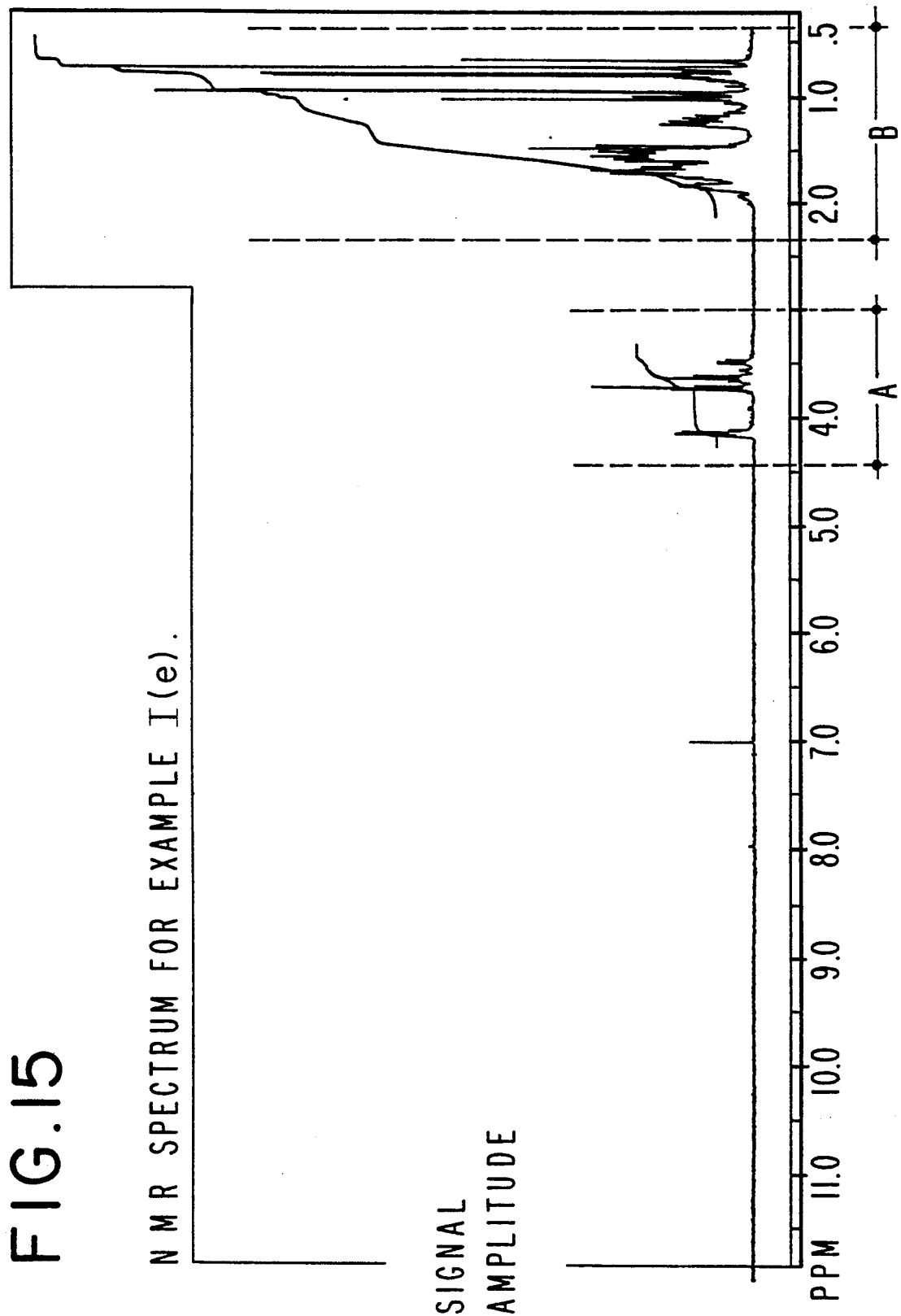

FIG. 15-A
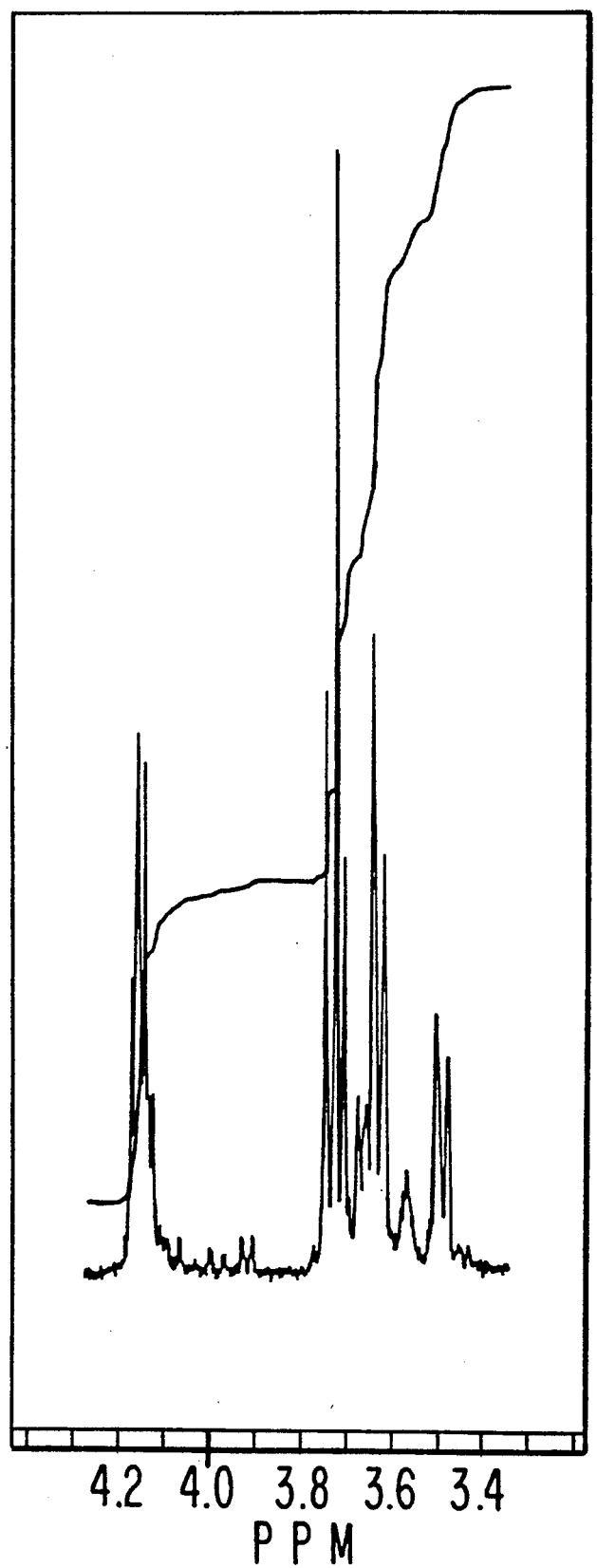

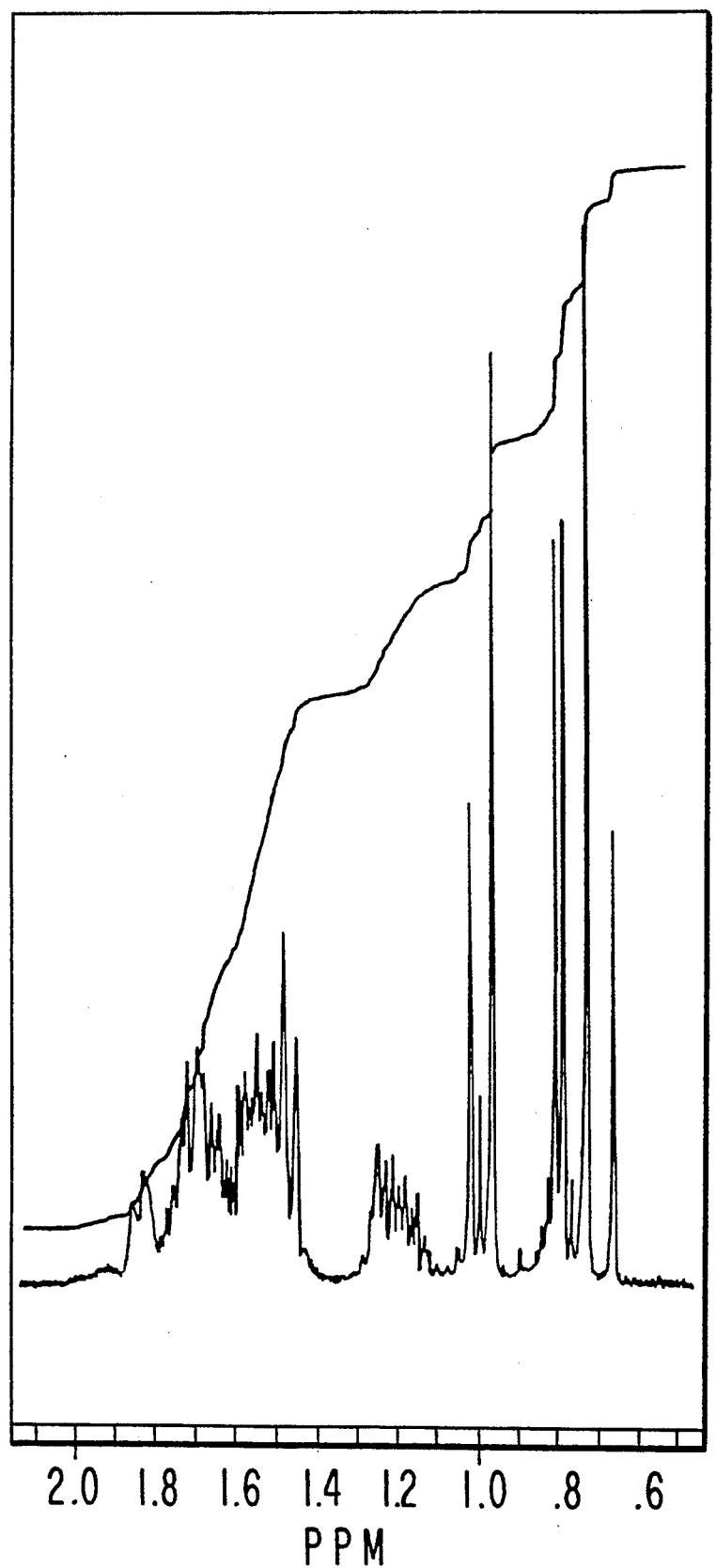
FIG.15-B

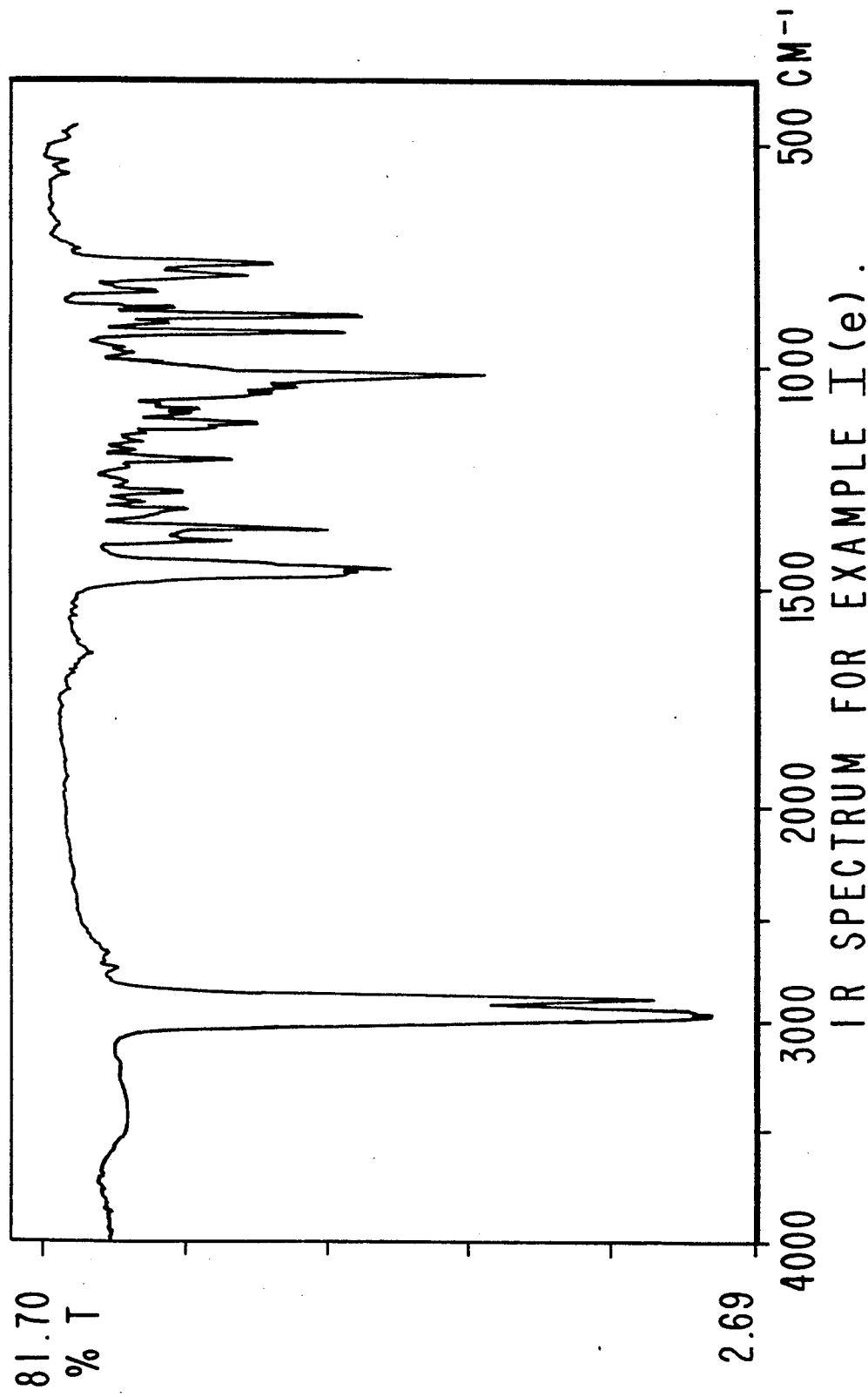

GC PROFILE FOR EXAMPLE II(a).

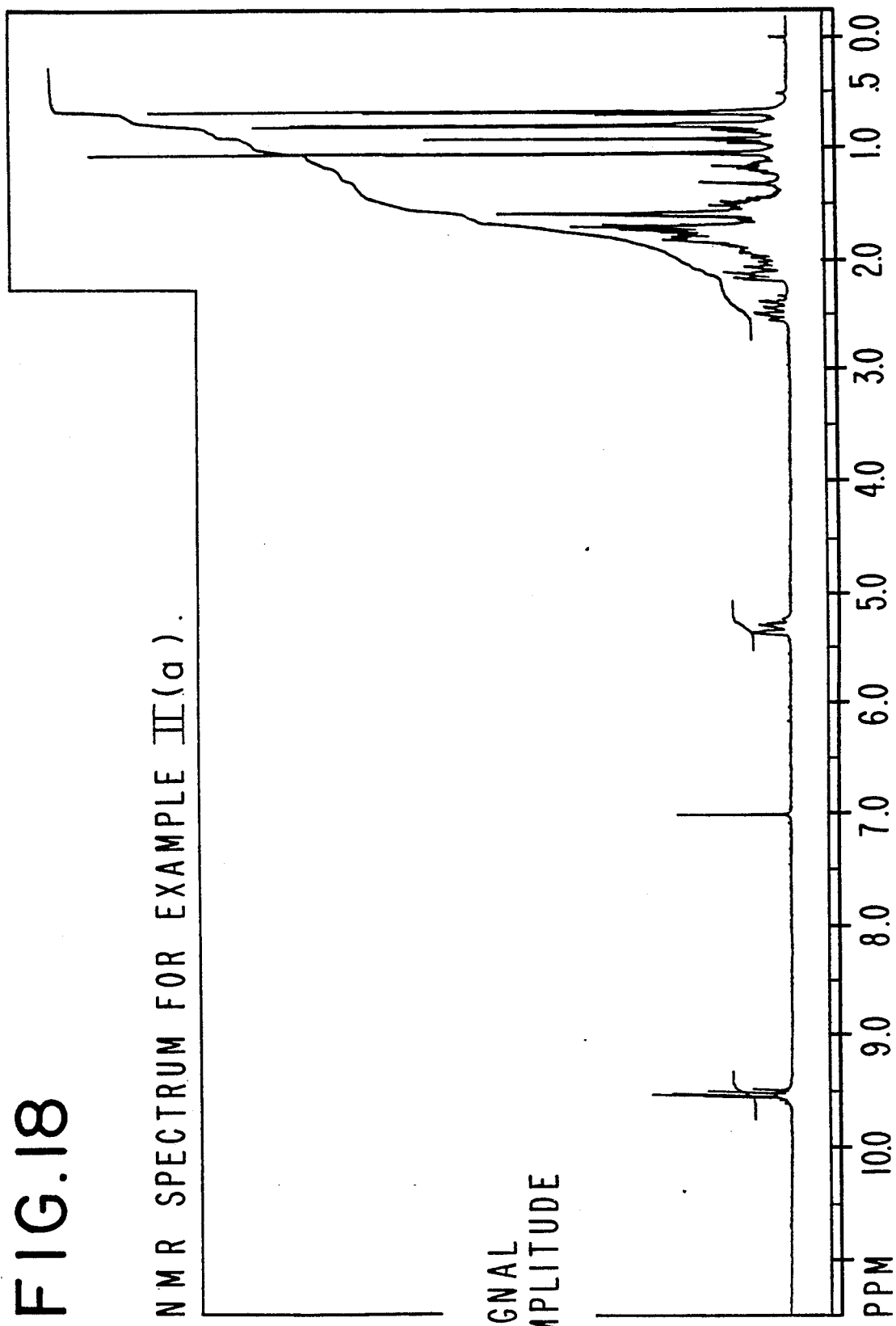
FIG.18 NMR SPECTRUM FOR EXAMPLE II(a).

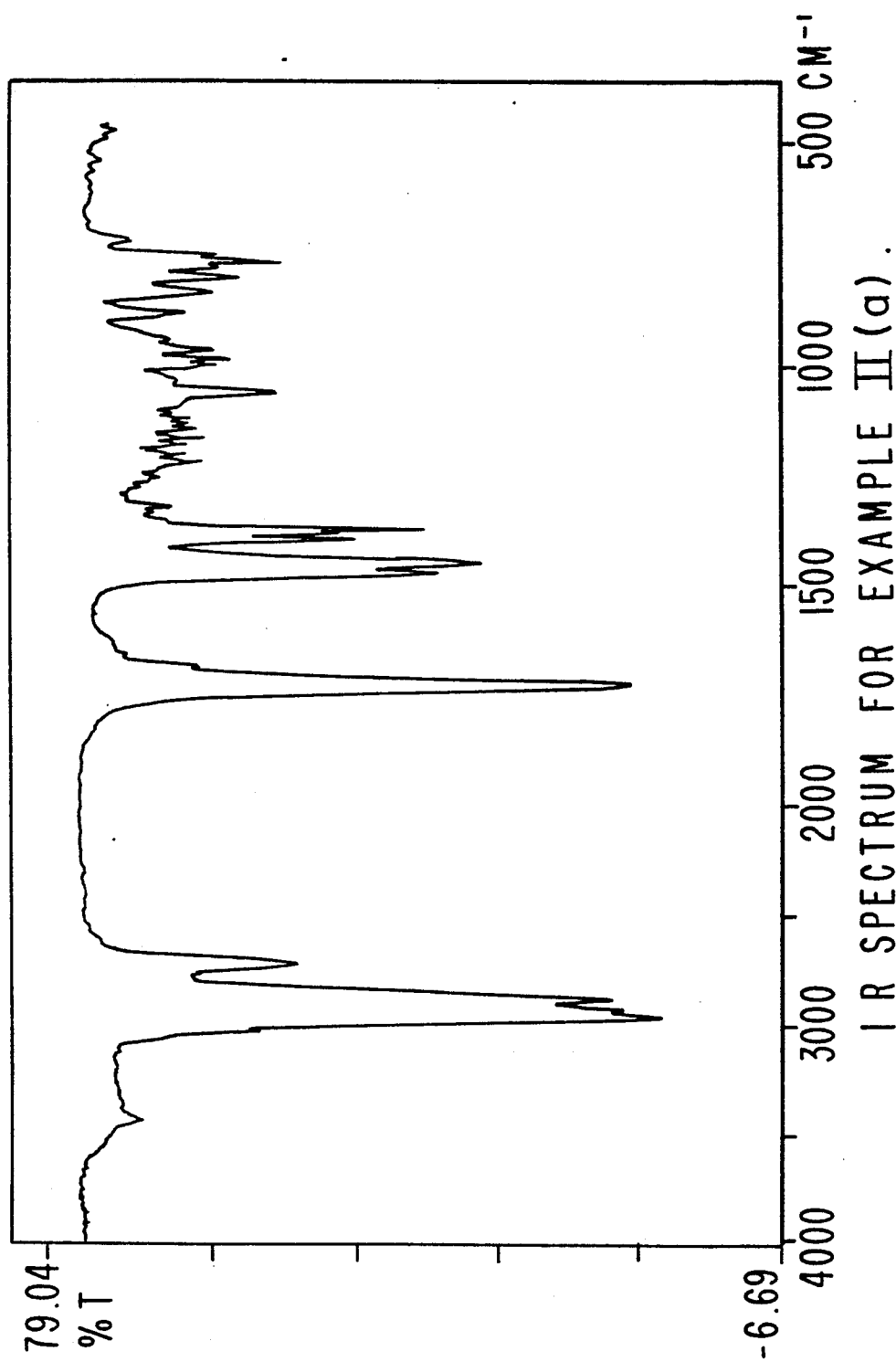
FIG.19 IR SPECTRUM FOR EXAMPLE II(a).

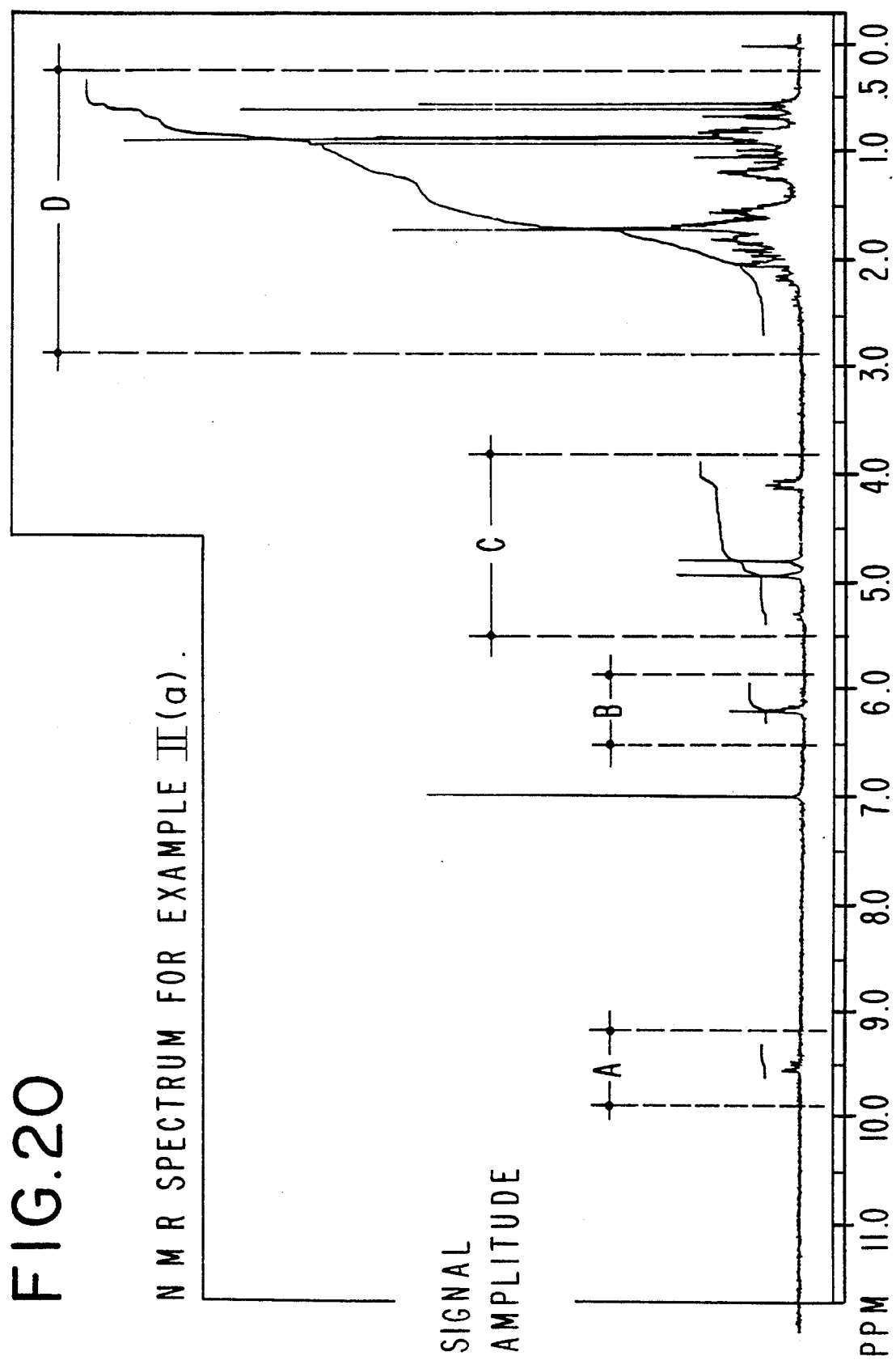

FIG.20-A
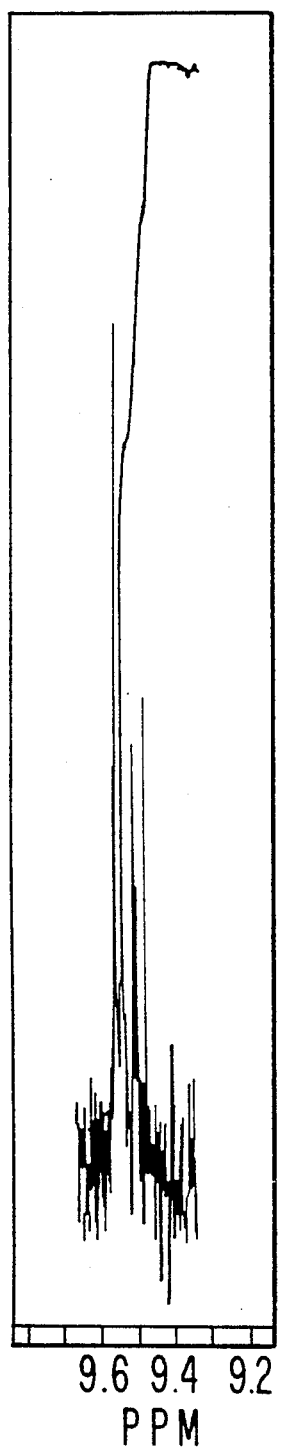
FIG.20-B
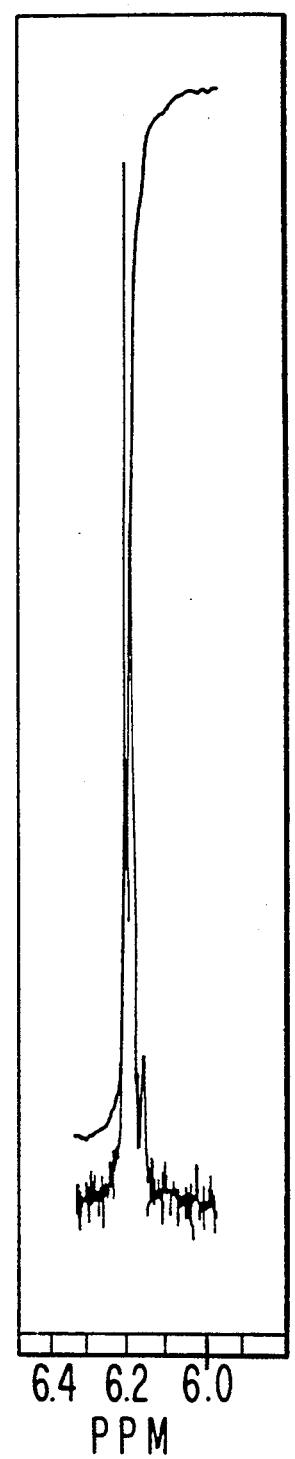

FIG. 20-C
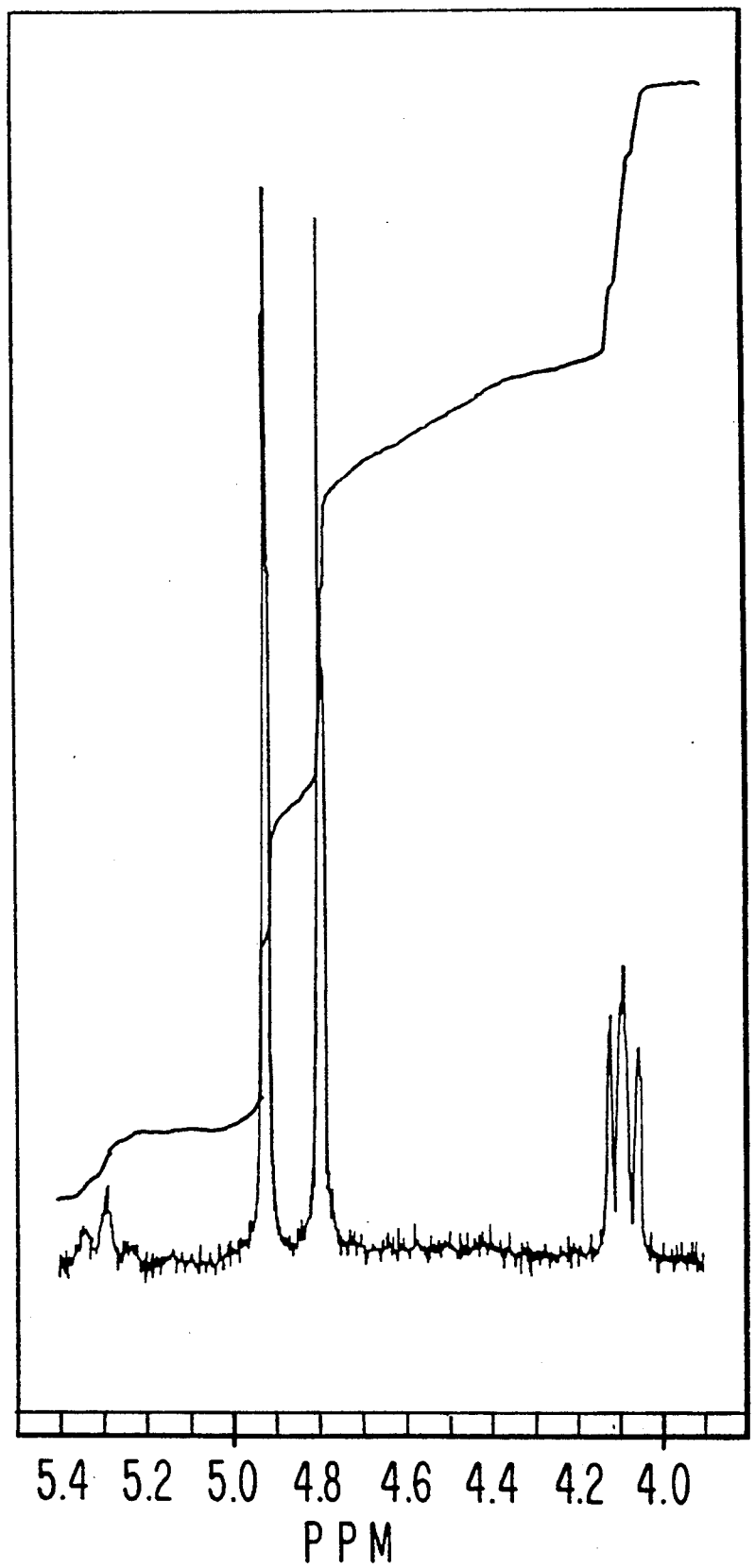

FIG.20-D
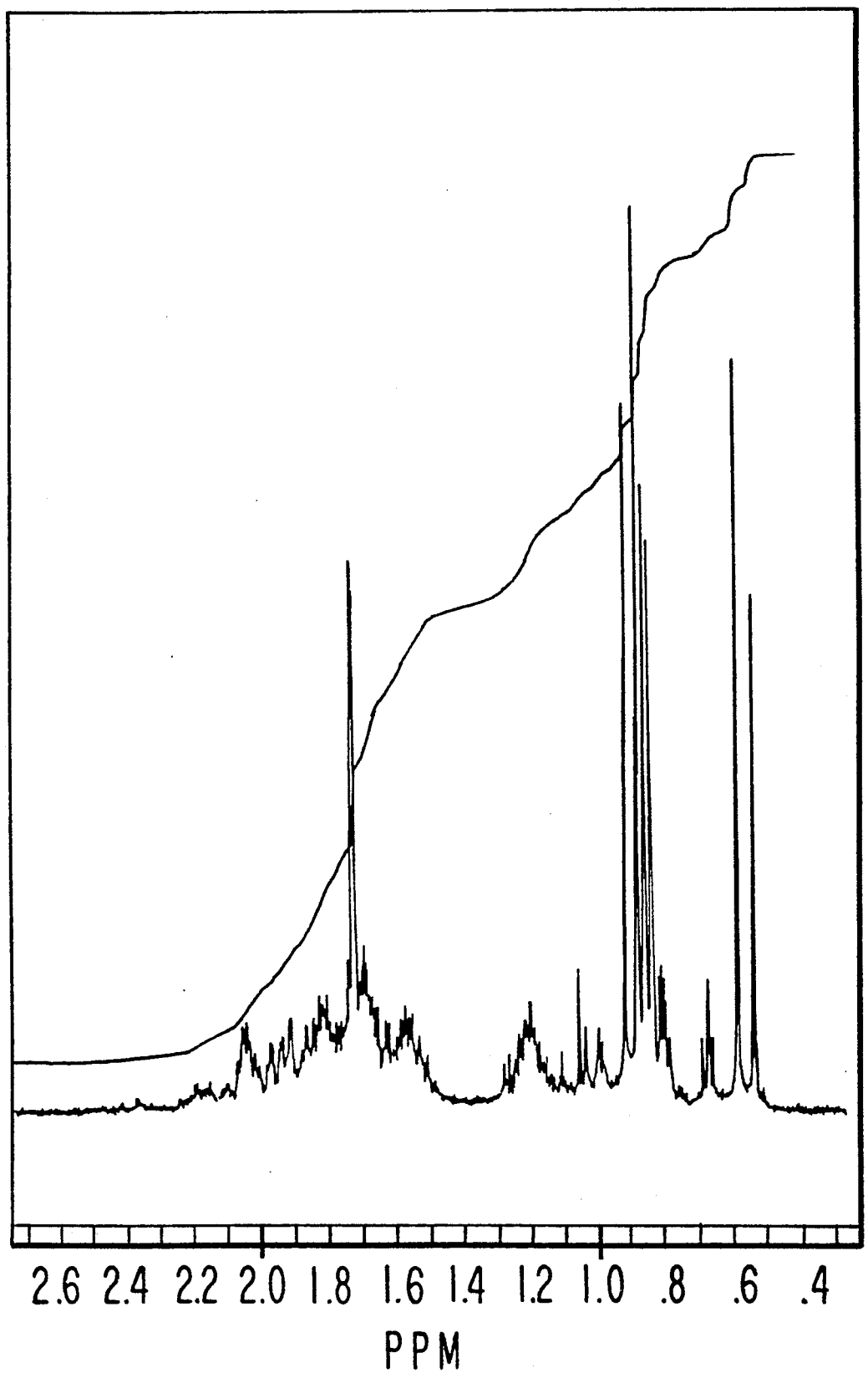

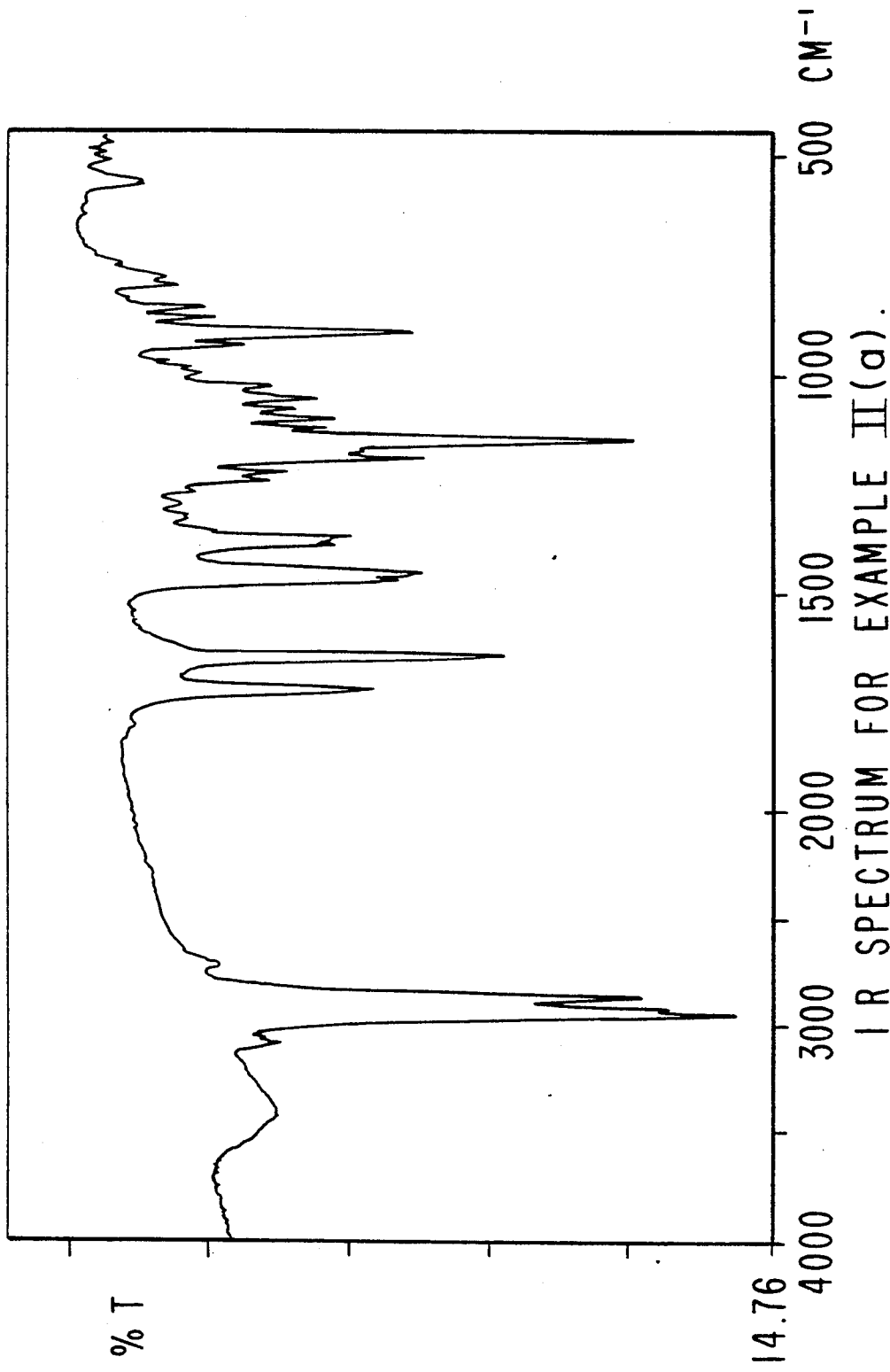

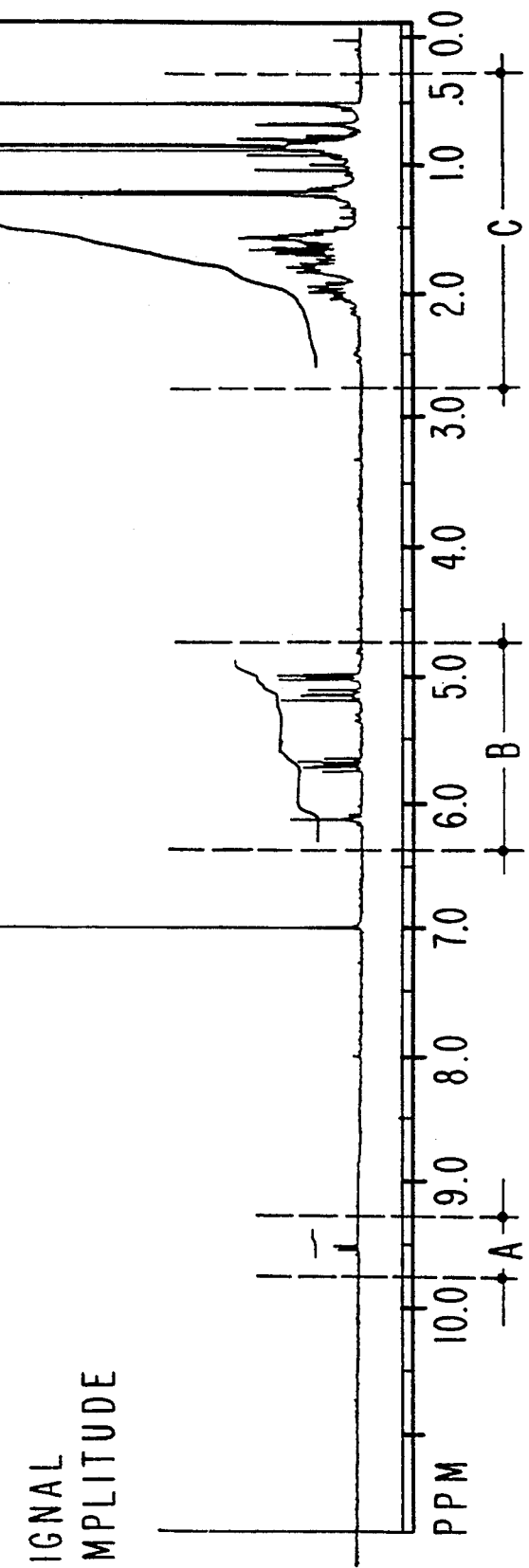
FIG. 22 NMR SPECTRUM FOR EXAMPLE II(a).

FIG.22-A
FIG.22-B
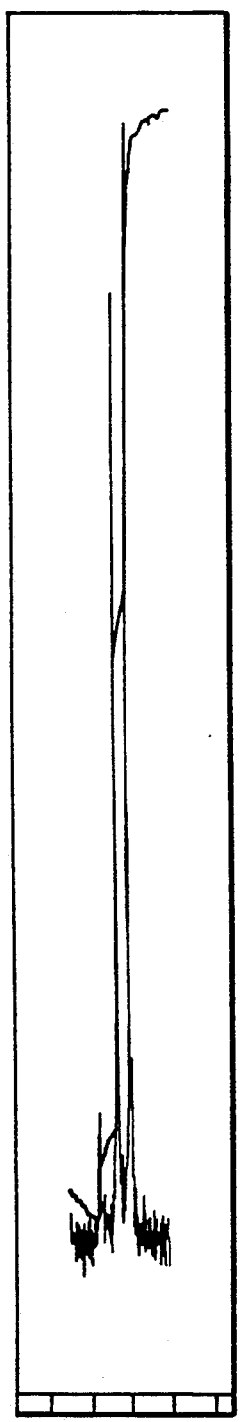
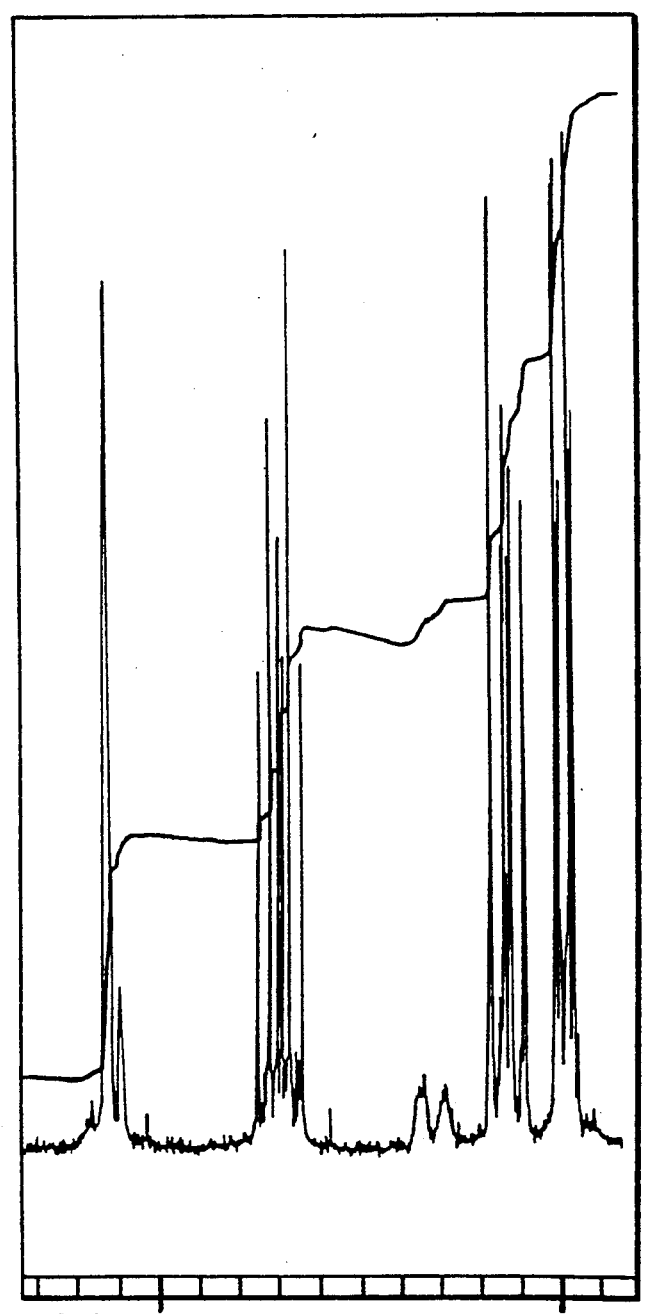

FIG.22-C
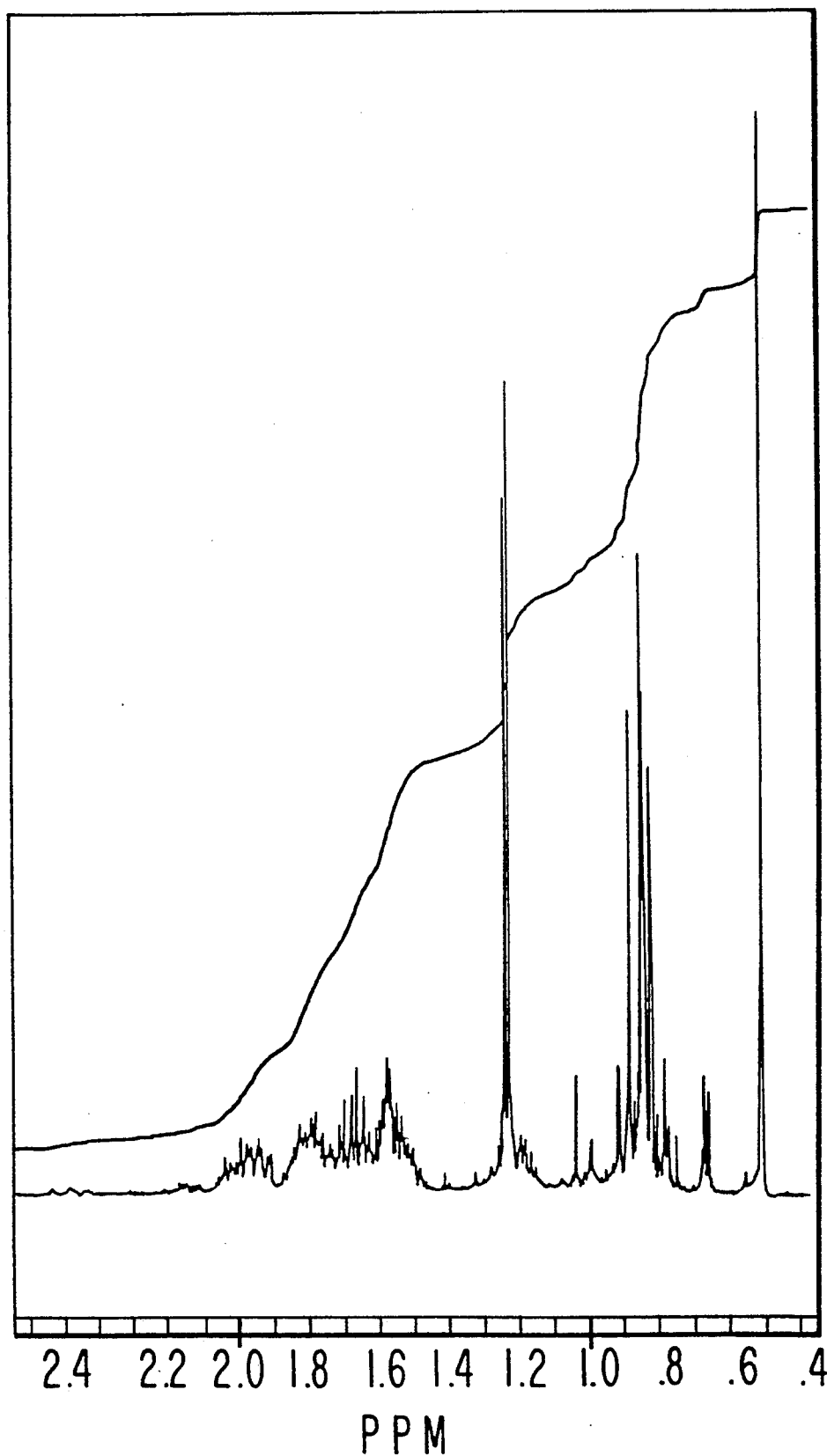

GLC PROFILE FOR EXAMPLE II (b).

NMR SPECTRUM FOR EXAMPLE II(b).

FIG.24-A
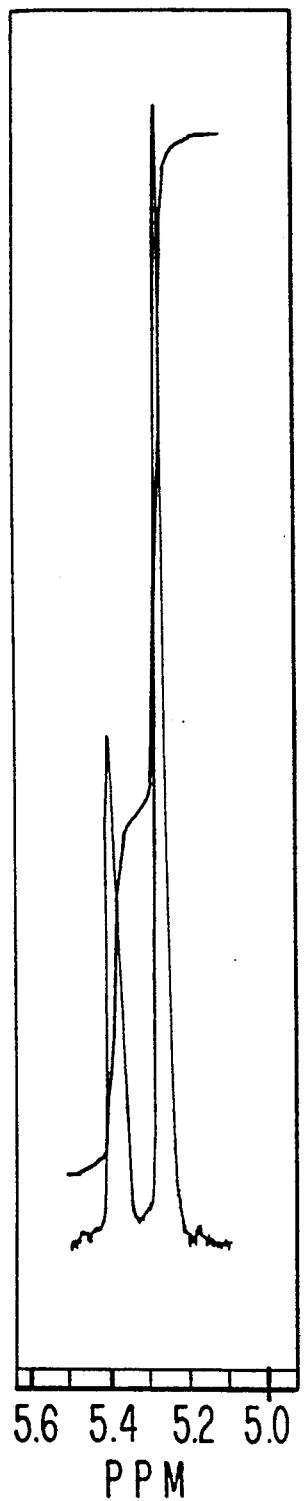
FIG.24-B
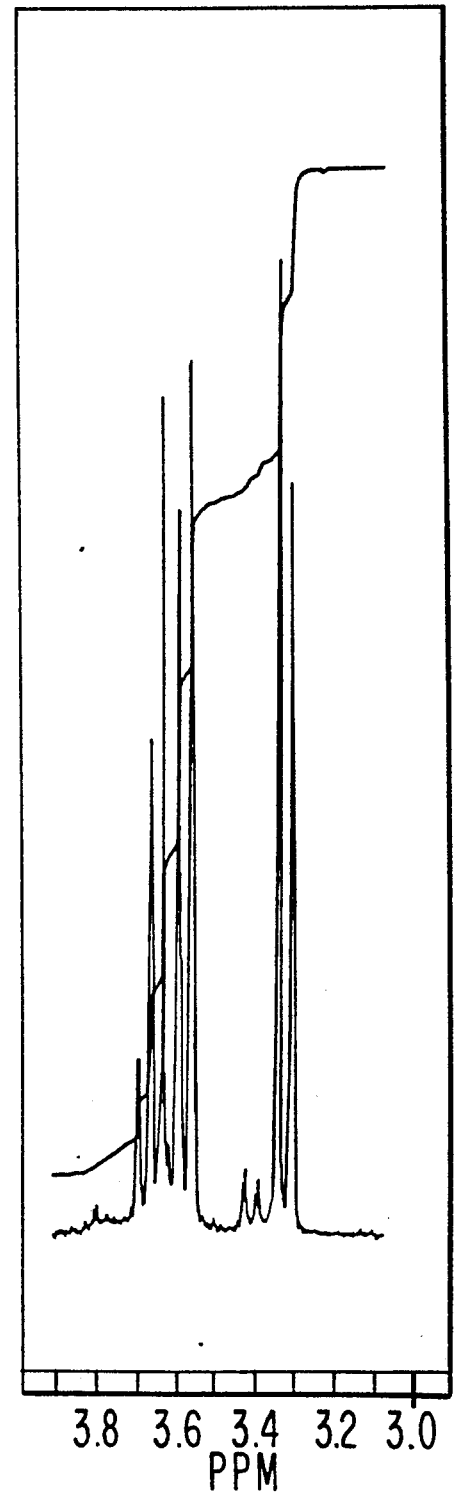

FIG. 24-C
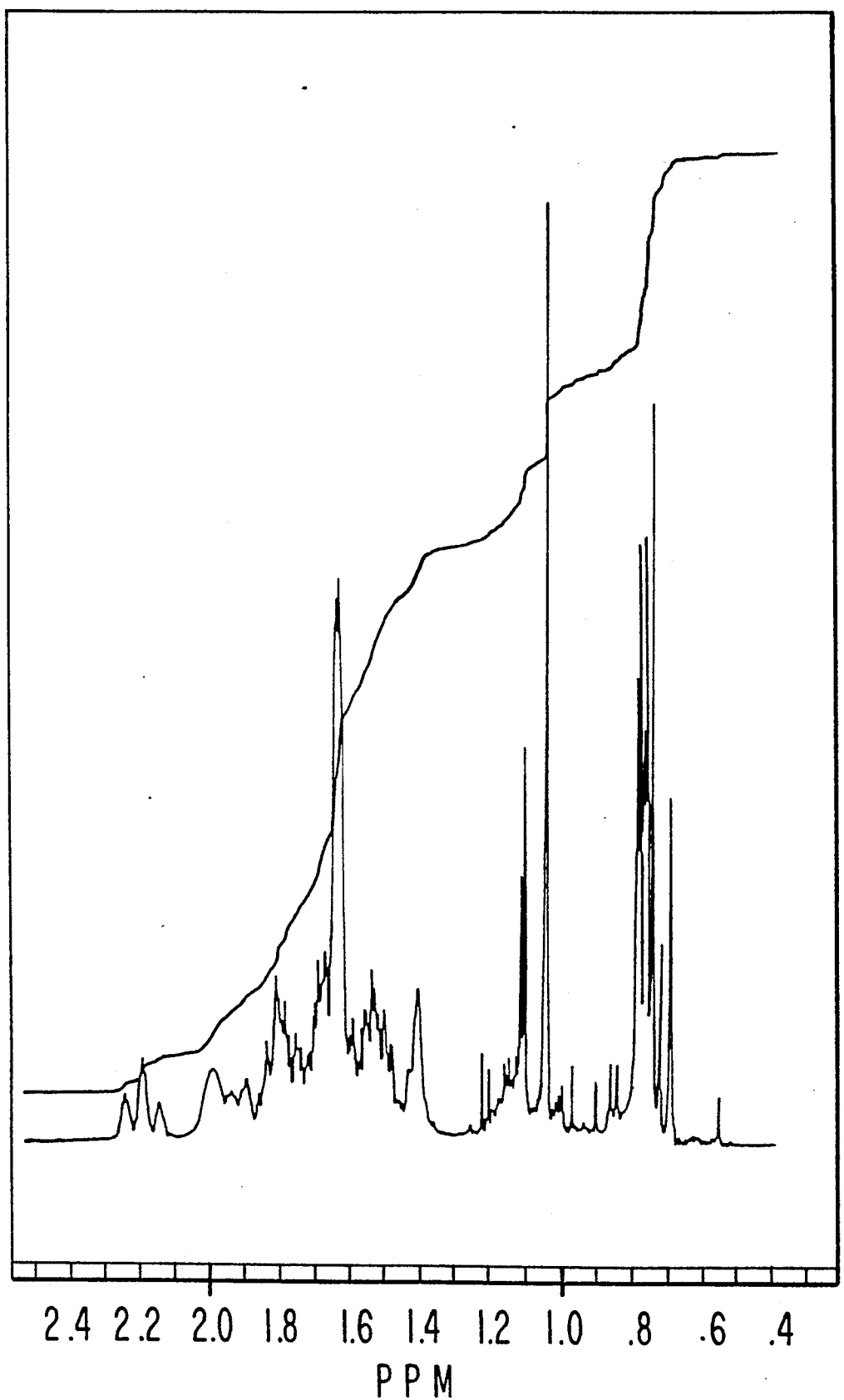

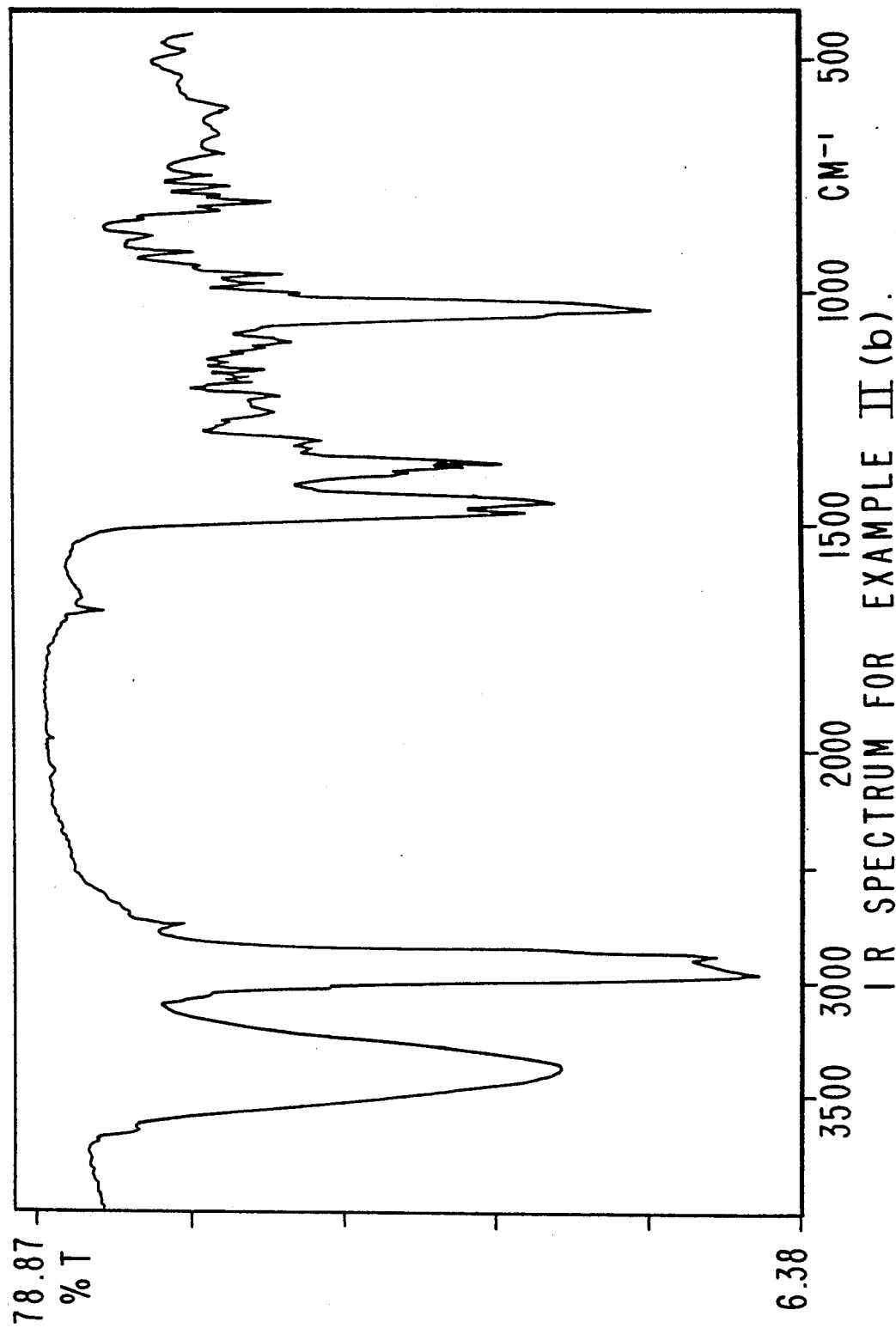

GC PROFILE FOR EXAMPLE II(c).

NMR SPECTRUM FOR EXAMPLE II(a).

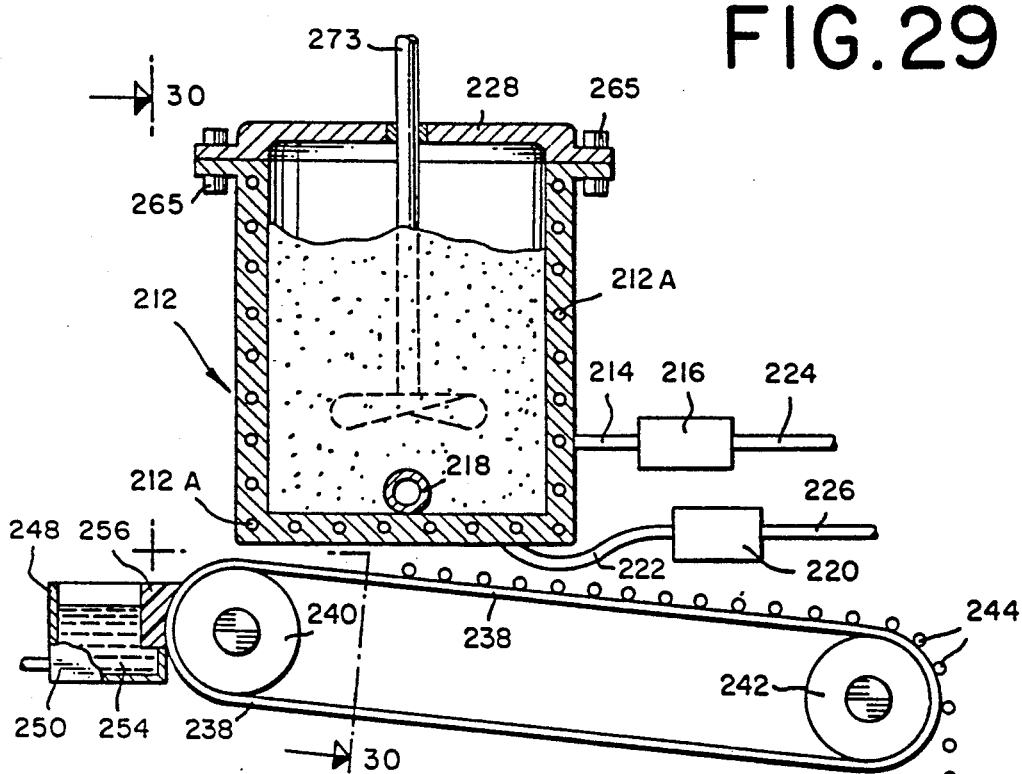
FIG.29
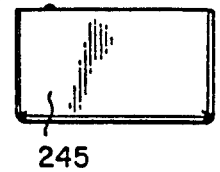
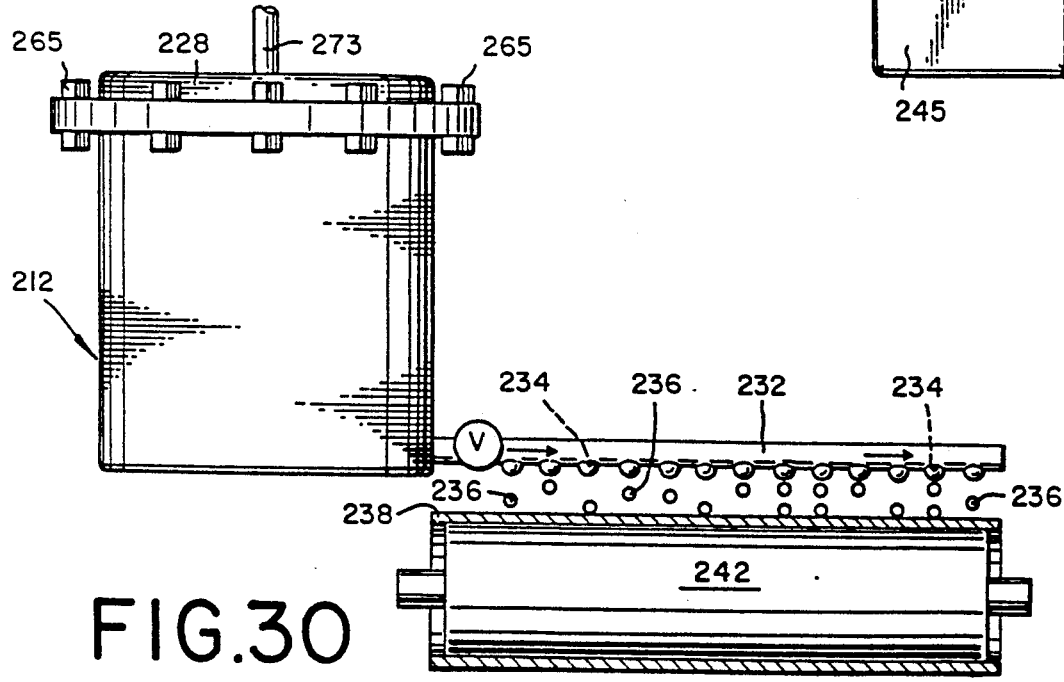
FIG.30

SUBSTITUTED CYCLOPENTYL OXABICYCLOOCTANES, CYCLOPENYL VINYL PYRANS, CYCLOPENTYLFORMYLCYCLOHEXENES AND CYCLOPENTYLHYDROXYMETHYL CYCLOHEXENES, PROCESSES FOR PREPARING SAME AND ORGANOLEPTIC USES THEREOF

BACKGROUND OF THE INVENTION

This invention relates to substituted cyclopentyl oxabicyclooctanes, cyclopentyl vinyl pyrans, cyclopentylformylcyclohexenes and cyclopentylhydroxymethyl cyclohexenes and uses thereof in augmenting or enhancing the aroma of perfume compositions, perfumed articles and colognes.

Balsamic, piney, sweaty, animalic, woody, ambery, fruity, musky, tobacco-like, sweet, apple-like, lactonic and coumarin-like aromas, with piney, ozoney, balsamic, herbaceous, buttery, ambery, orris-like, woody, plum-like, sweaty and animalic topnotes and "air dried clothing" undertones are particularly desirable in augmenting or enhancing the aroma of perfume compositions, colognes and perfumed articles (e.g., solid or liquid, anionic, cationic, nonionic or zwitterionic detergents, fabric softener compositions, fabric softener articles, hair preparations, cosmetic powders and perfumed polymers).

Compounds having the oxabicyclooctane nucleus have been known for use in augmenting or enhancing the aroma of perfume compositions, perfumed articles and colognes for a number of years. Thus, the compound having the structure:

is disclosed at column 4, lines 35-40 of U.S. Pat. No. 4,269,862 (Sprecker, et al, II) to have a minty, camphor, woody and piney aroma profile. U.S. Pat. No. 4,269,862 further discloses the genus defined according to the structure:

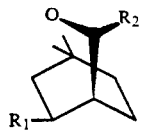

wherein $R_1$ is hydrogen or methyl and $R_2$ is $C_3$–$C_5$ alkyl or alkenyl to have utility in augmenting or enhancing the aroma of perfume compositions, colognes and perfumed articles.

Furthermore, cineole itself having the structure:

is disclosed by Arctander "Perfume and Flavor Chemicals" (Aroma Chemicals), at monograph 616 to have a eucalyptus aroma (its common name is "eucalyptol").

U.S. Pat. No. 5,081,262 issued on Jan. 14, 1992 discloses substituted cyclopentenyl oxabicyclooctanes, cyclopentenylformylcyclohexenes and cyclopentenylhydroxymethyl cyclohexenes, processes for preparing same and organoleptic uses thereof. The oxabicyclooctane derivatives, the cyclopentenylformylcyclohexenes and cyclopentenylhydroxymethyl cyclohexenes of U.S. Pat. No. 5,081,262 have the generic structures:

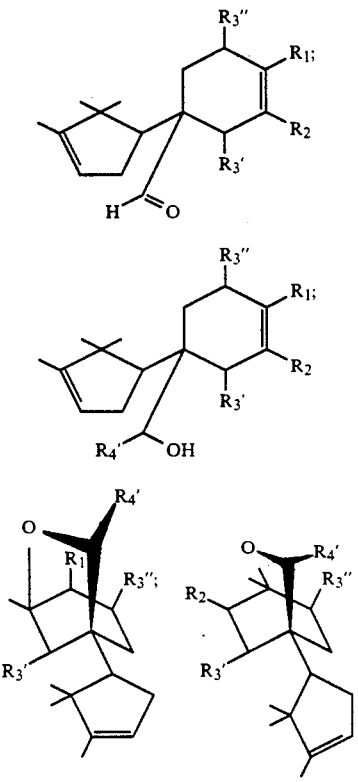

wherein $R_1$, $R_2$, $R_3'$ and $R_3''$ each represents hydrogen or methyl with the provisos:
(i) one or two of $R_1$, $R_2$, $R_3'$ and $R_3''$ is methyl;
(ii) $R_1$ and/or $R_2$ is methyl;
(iii) at least one of $R_3'$ and $R_3''$ represents hydrogen; and
(iv) when $R_1$ and $R_2$ are both methyl then each of $R_3'$ and $R_3''$ each represent hydrogen.

Nothing in the prior art, however, discloses the substituted cyclopentyl oxabicyclooctanes, cyclopentyl vinyl pyrans, cyclopentylformylcyclohexenes and cyclopentylhydroxymethyl cyclohexenes of our invention or their organoleptic uses.

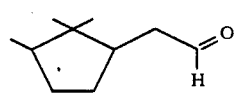

(Conditions: SE-30 column programmed at 150°-220° C. at 8° C. per minute).

Figure 2:
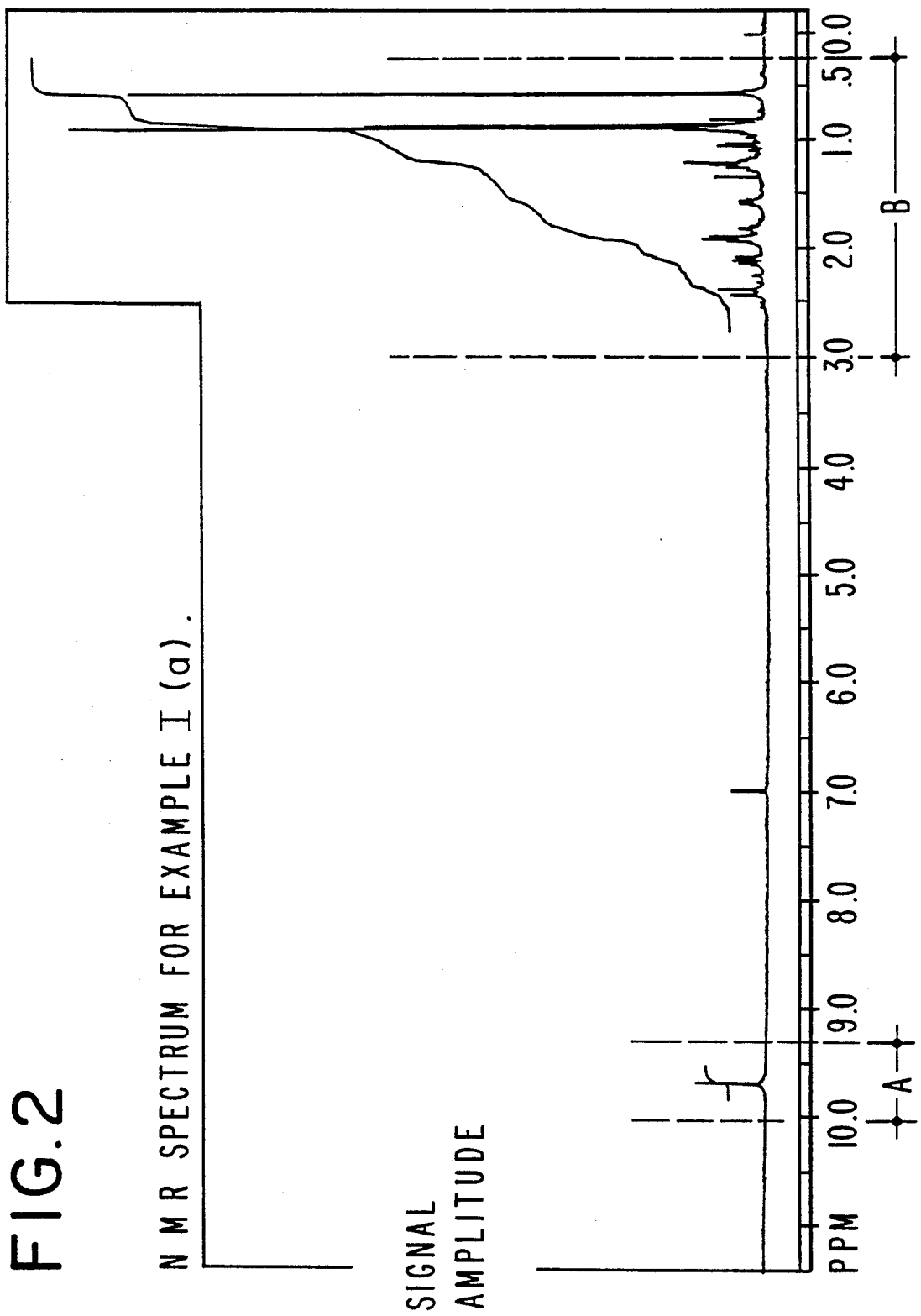

FIG. 2 is the NMR spectrum for the compound having the structure:

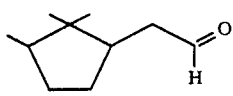

produced according to Example I(a).

FIGS. 2A and 2B are enlarged sections "A" and "B" of FIG. 2.

Figure 3:
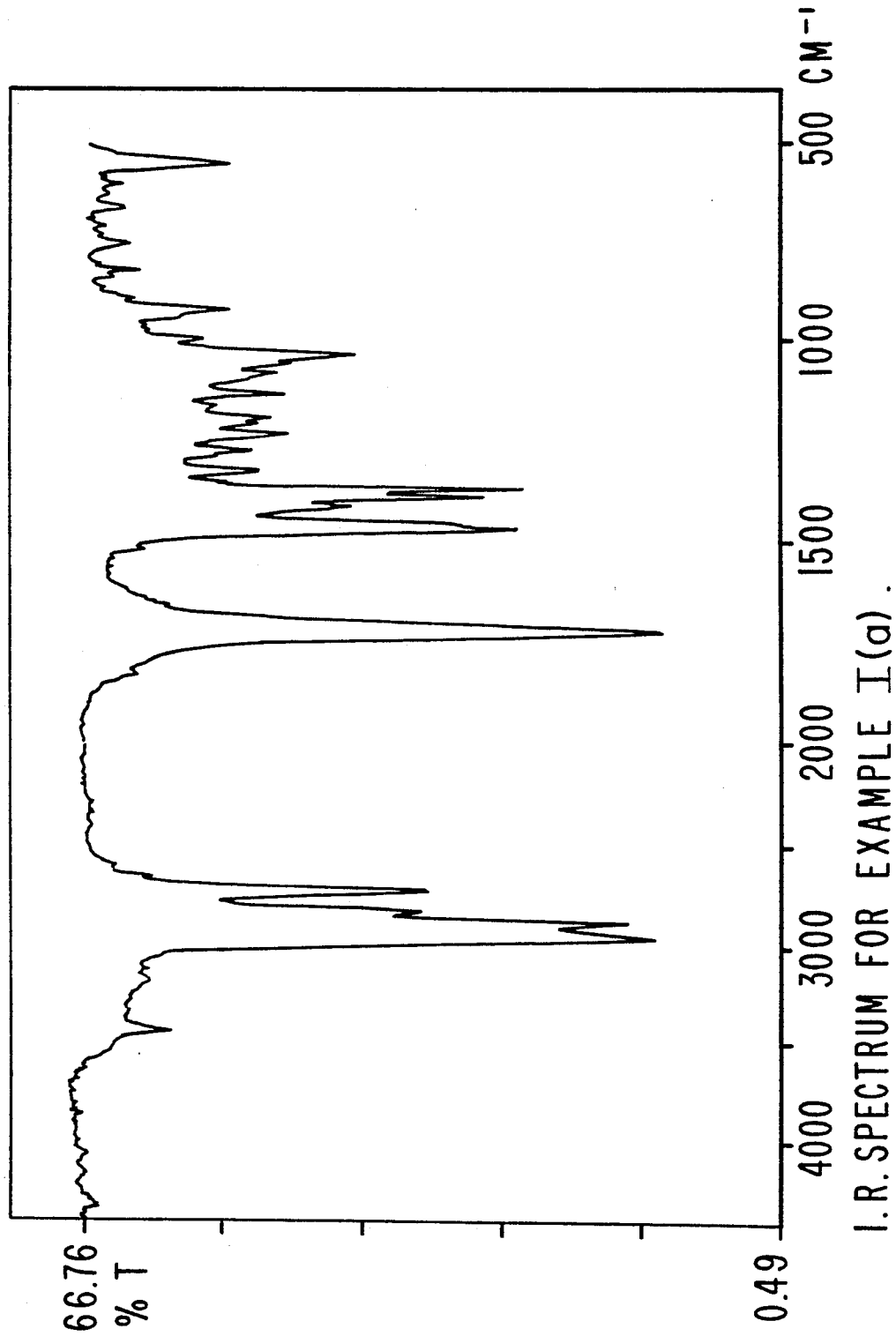

FIG. 3 is the infra-red spectrum for the compound having the structure:

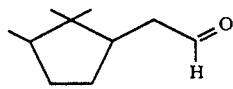

produced according to Example I(a).

Figure 4:
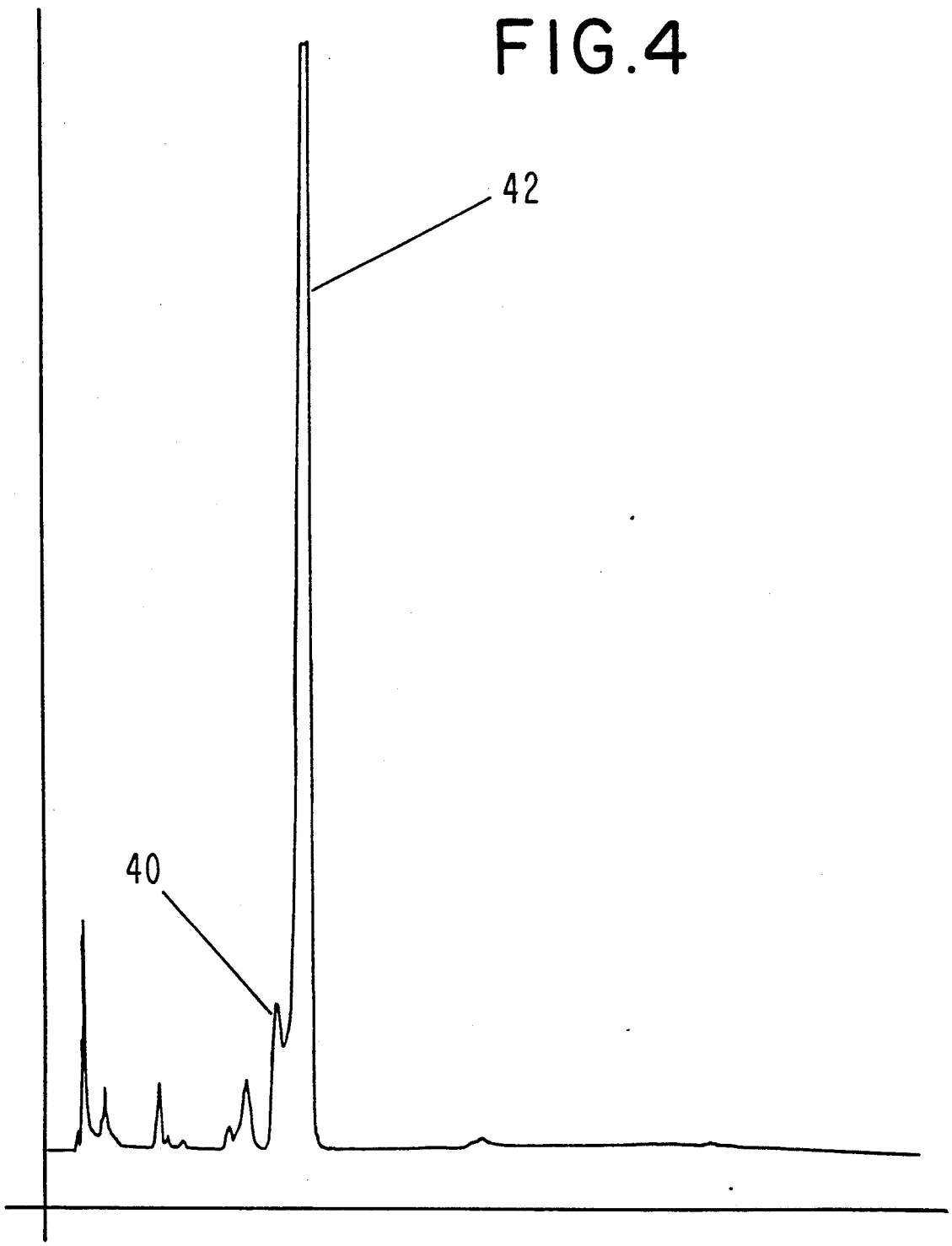

FIG. 4 is the GC profile for the reaction product of Example I(b) containing the compound having the structure:

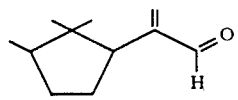

(Conditions: SE-30 column programmed at 150°–220° C. at 8° C. per minute).

Figure 5:
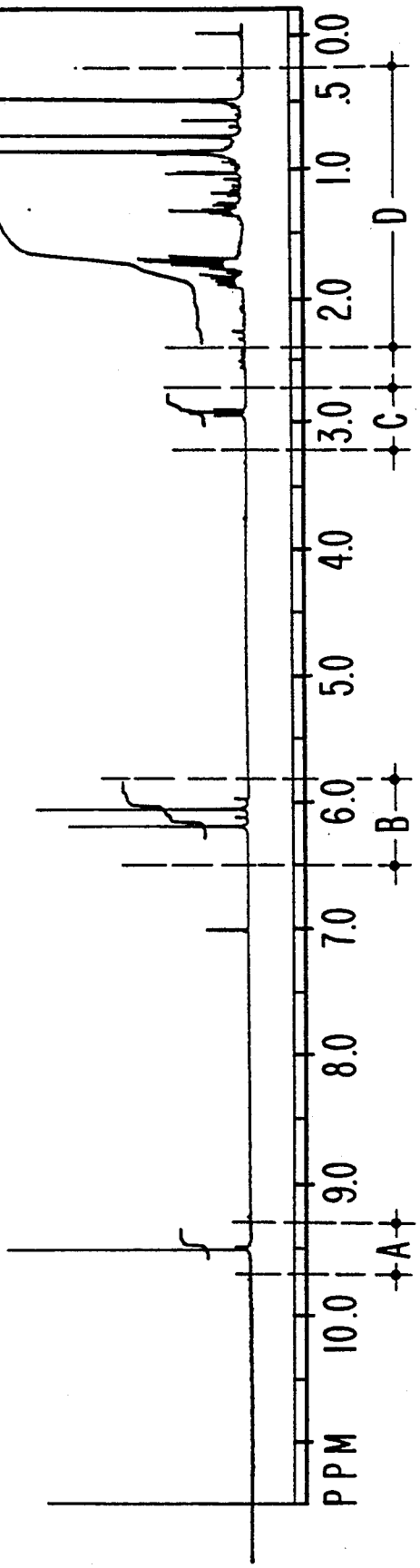

FIG. 5 is the NMR spectrum for the compound having the structure:

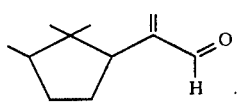

FIGS. 5A, 5B, 5C and 5D are enlarged sections "A", "B", "C" and "D", respectively, of the NMR spectrum of FIG. 5.

FIG. 6 is the infra-red spectrum for the compound having the structure:

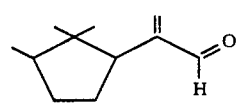

prepared according to Example I(b).

Figure 7:
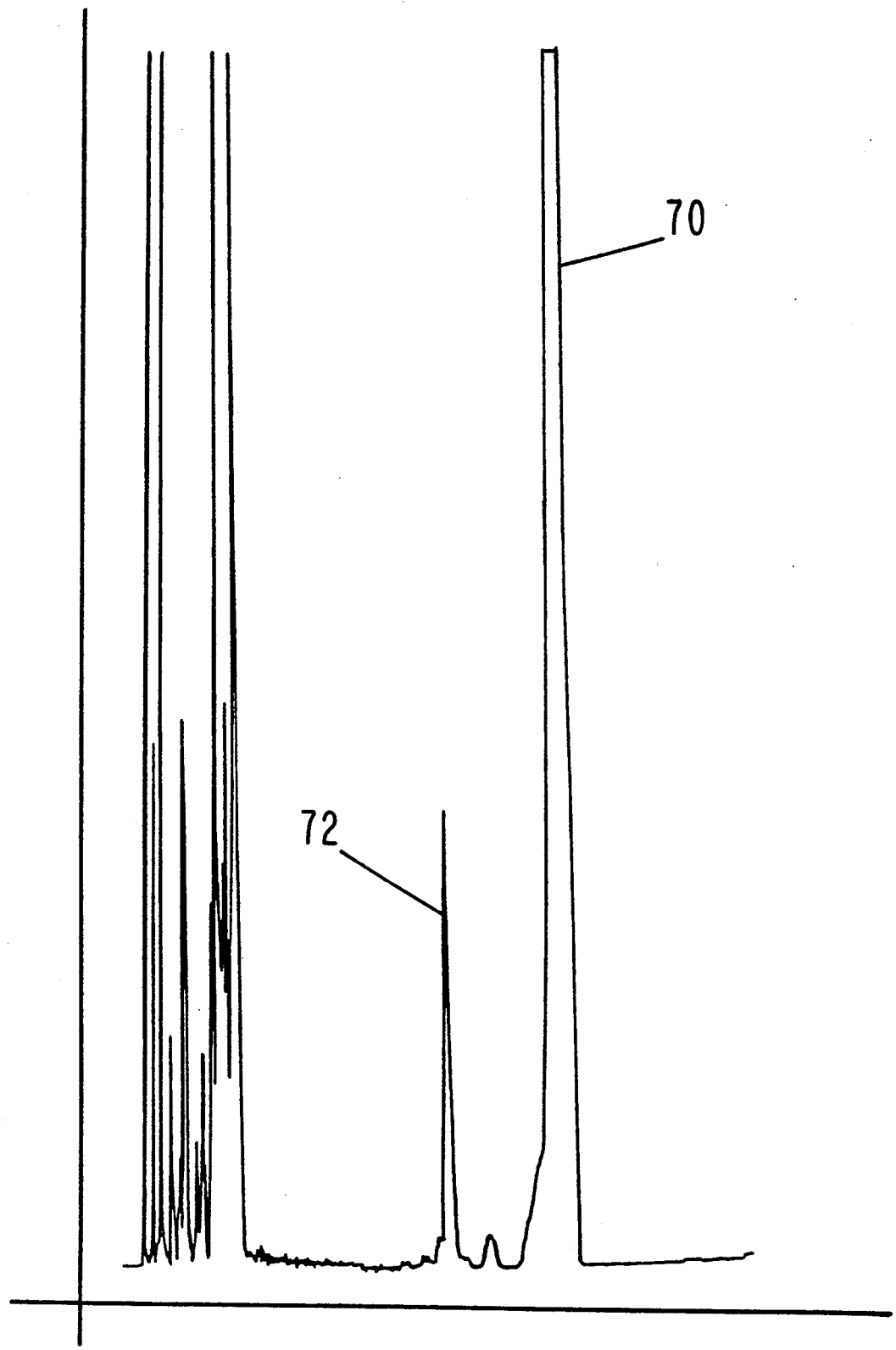

FIG. 7 is the GC profile for the reaction product of Example I(c) containing the compounds having the structures:

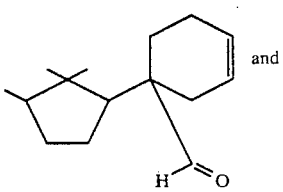

and

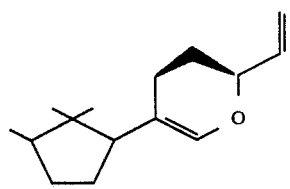

(Conditions: SE-30 column programmed at 150°–220° C. at 8° C. per minute).

FIG. 8 is the NMR spectrum for the compound having the structure:

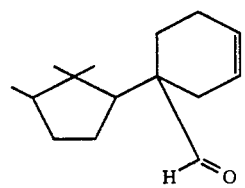

prepared according to Example I(c).

FIGS. 8A, 8B and 8C are enlarged sections "A", "B" and "C" of the NMR spectrum of FIG. 8.

FIG. 9 is the infra-red spectrum for the compound having the structure:

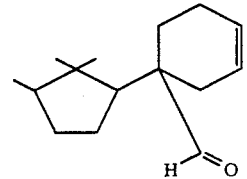

prepared according to Example I(c).

FIG. 10 is the NMR spectrum for the compound having the structure:

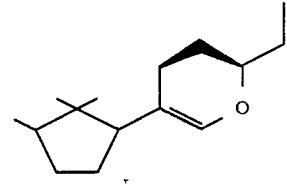

produced according to Example I(c).

FIGS. 10A, 10B, 10C and 10D are enlarged sections "A", "B", "C" and "D" of the NMR spectrum of FIG. 10.

Figure 11:
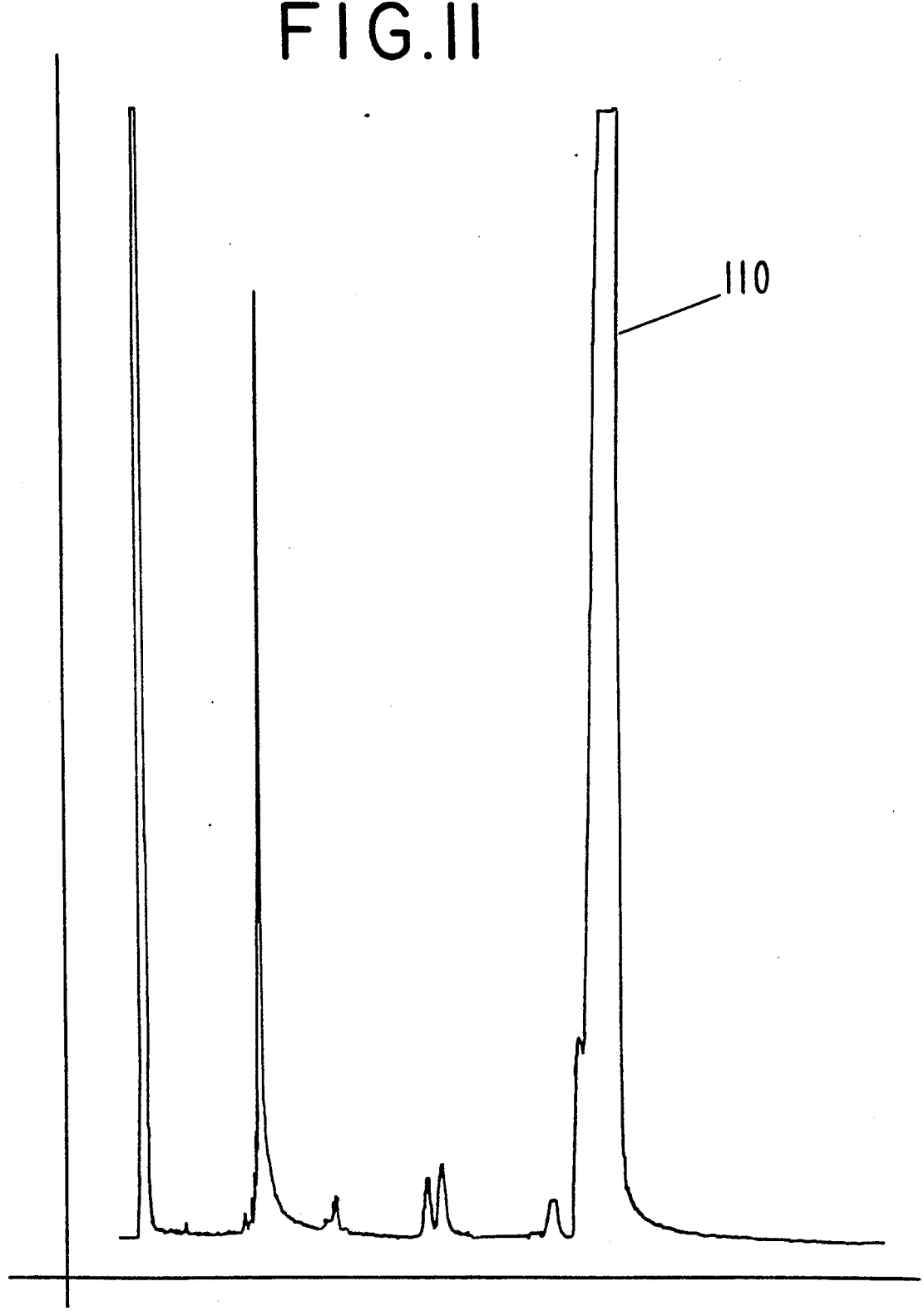

FIG. 11 is the GC profile for the reaction product of Example I(d) containing the compound having the structure:

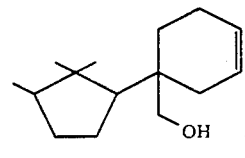

FIG. 12 is the NMR spectrum for the compound having the structure:

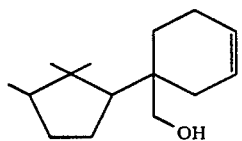

prepared according to Example I(d).

FIGS. 12A, 12B and 12C are enlarged sections "A", "B" and "C" of the NMR spectrum of FIG. 12.

Figure 13:
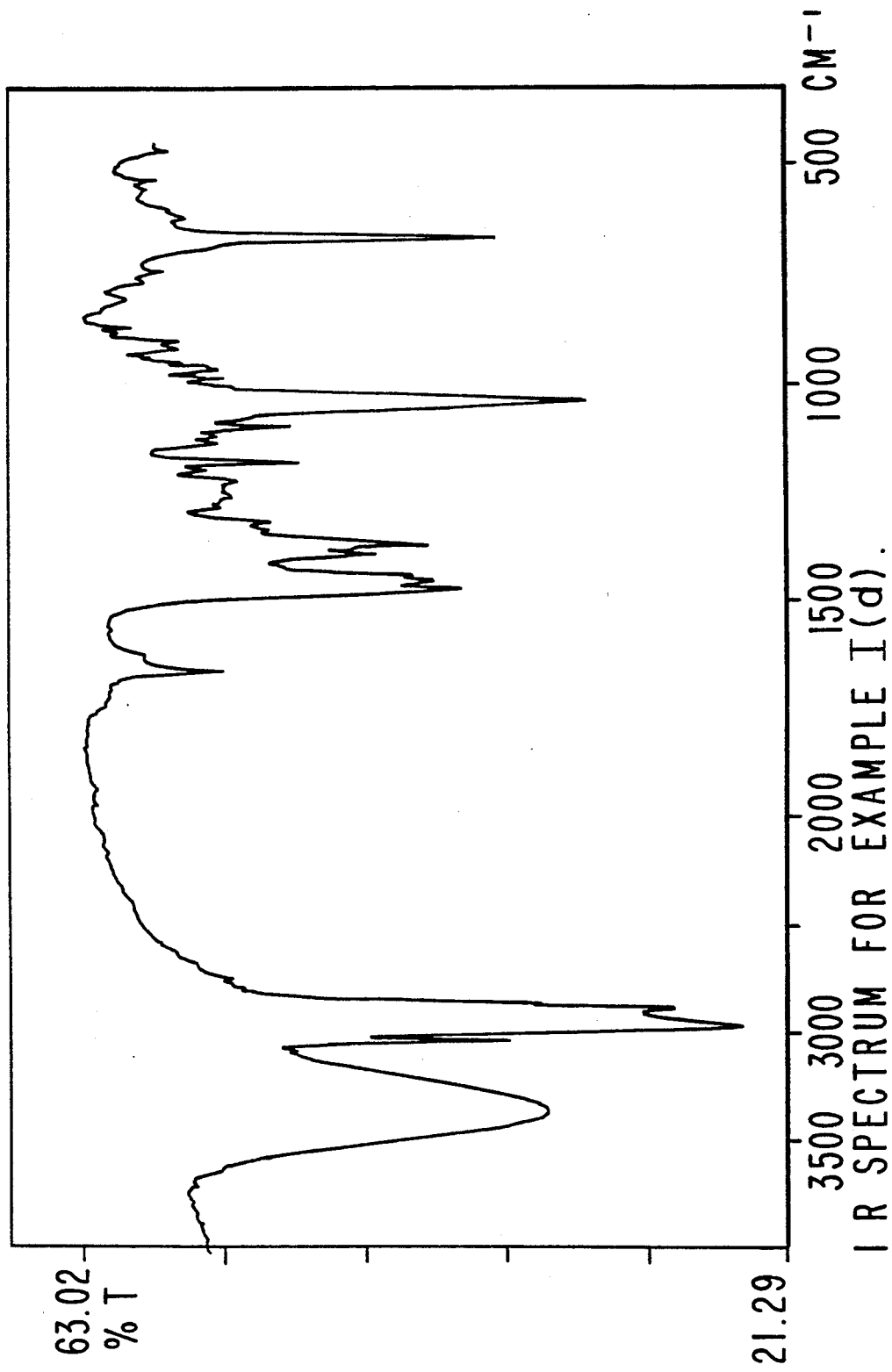

FIG. 13 is the infra-red spectrum for the compound having the structure:

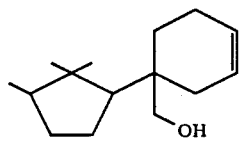

prepared according to Example I(d).

Figure 14:
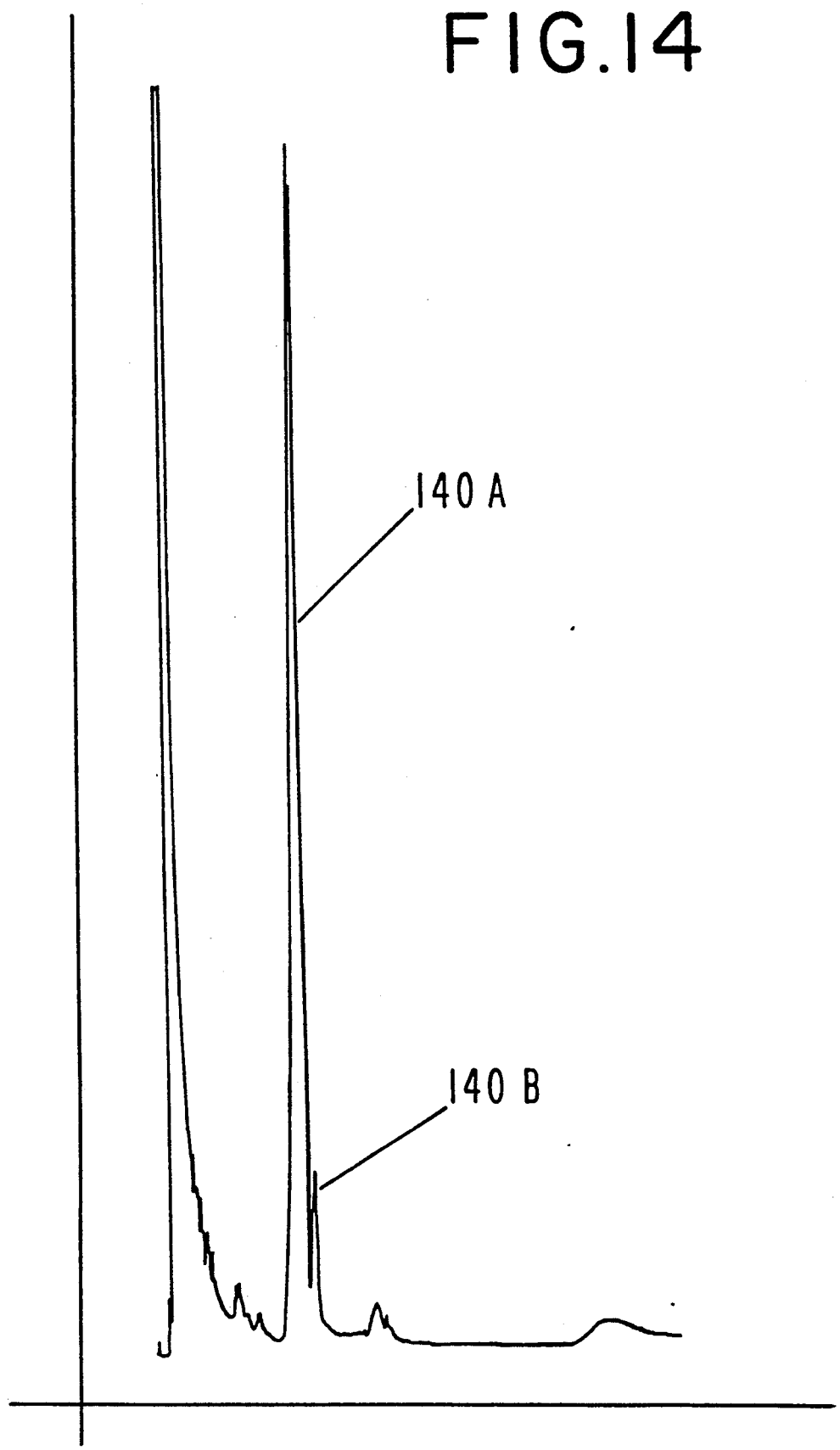

FIG. 14 is the GC profile for the reaction product of Example I(e) containing the compound having the structure:

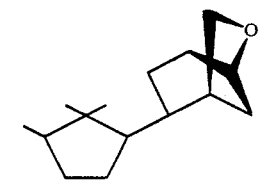

and

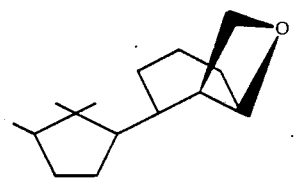

FIG. 15 is the NMR spectrum for the mixture of compounds having the structures:

and

prepared according to Example I(e).

FIGS. 15A and 15B are enlarged sections "A" and "B", respectively, of the NMR spectrum of FIG. 15.

FIG. 16 is the infra-red spectrum for the mixture of compounds having the structures:

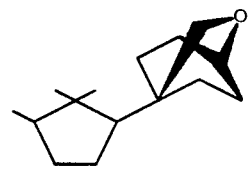

and

prepared according to Example I(e).

Figure 17:
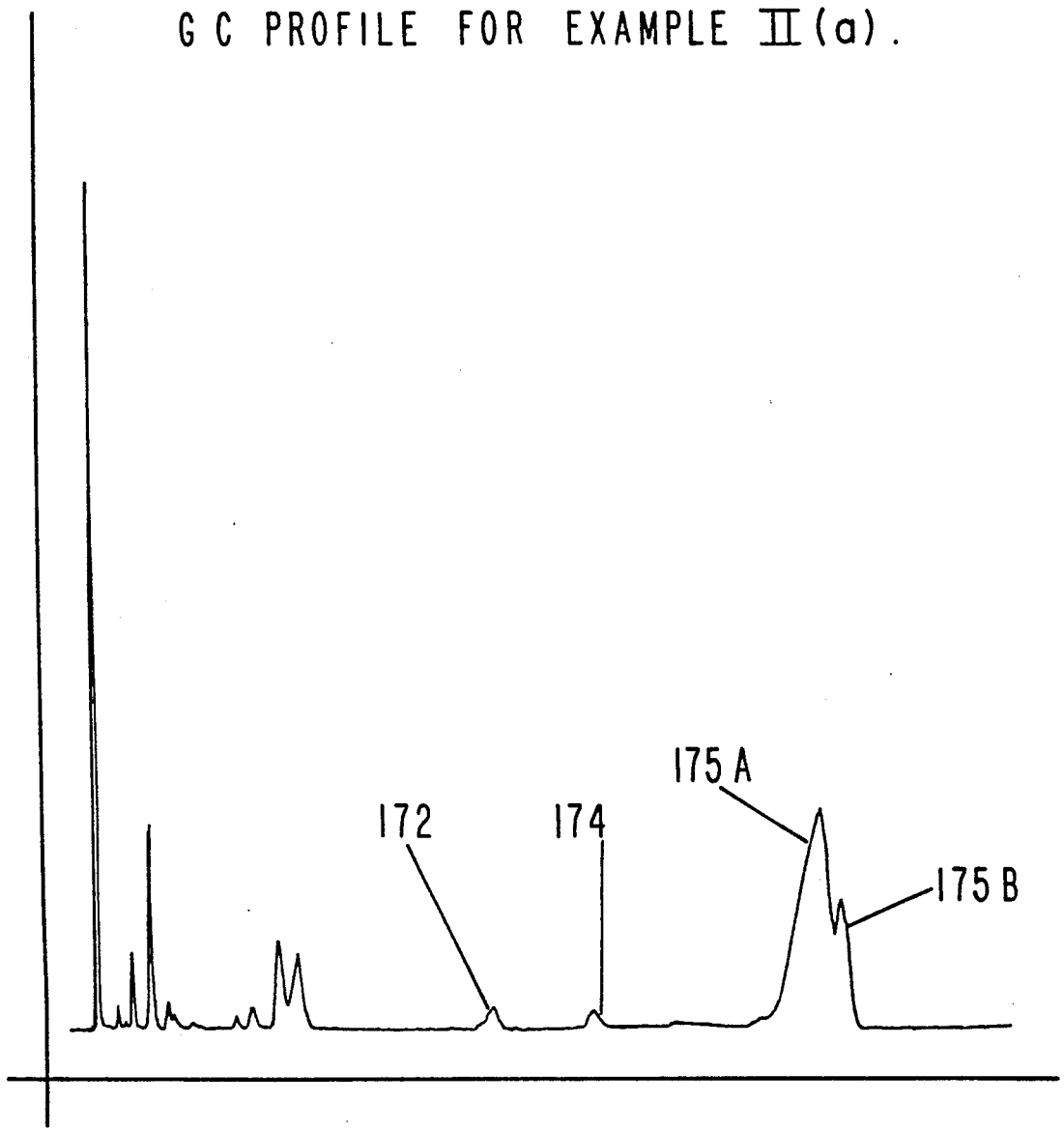

FIG. 17 is the GC profile for the reaction product of Example II(a) containing the compounds having the structures:

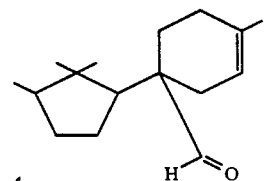

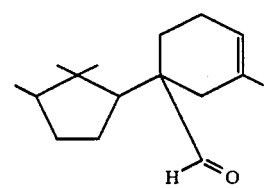

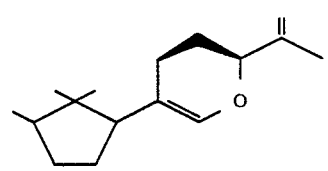

and

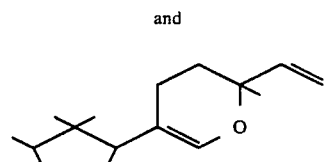

(Conditions: Carbowax column programmed at 150°–220° C. at 8° C. per minute)

FIG. 18 is the NMR spectrum for the mixture of compounds having the structures:

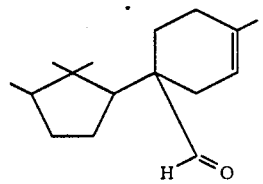

-continued
and

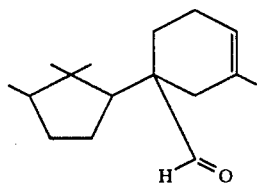

prepared according to Example II(a).

FIG. 19 is the infra-red spectrum for the mixture of compounds having the structures:

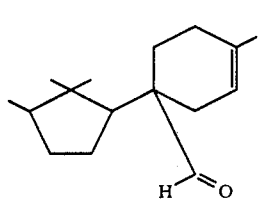

and

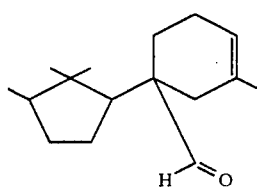

prepared according to Example II(a).

FIG. 20 is the NMR spectrum for the compound having the structure:

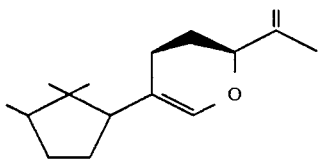

prepared according to Example II(a).

FIGS. 20A, 20B, 20C and 20D are enlargements of sections "A", "B", "C" and "D" of the NMR spectrum of FIG. 20.

FIG. 21 is the infra-red spectrum for the compound having the structure:

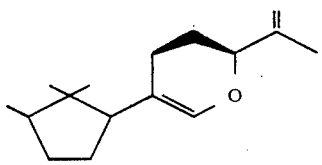

prepared according to Example II(a).

FIG. 22 is the NMR spectrum for the compound having the structure:

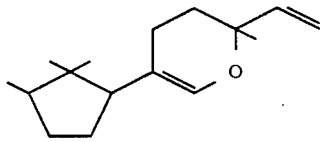

prepared according to Example II(a).

FIGS. 22A, 22B and 22C are enlargements of sections "A", "B" and "C" of the NMR spectrum of FIG. 22.

Figure 23:
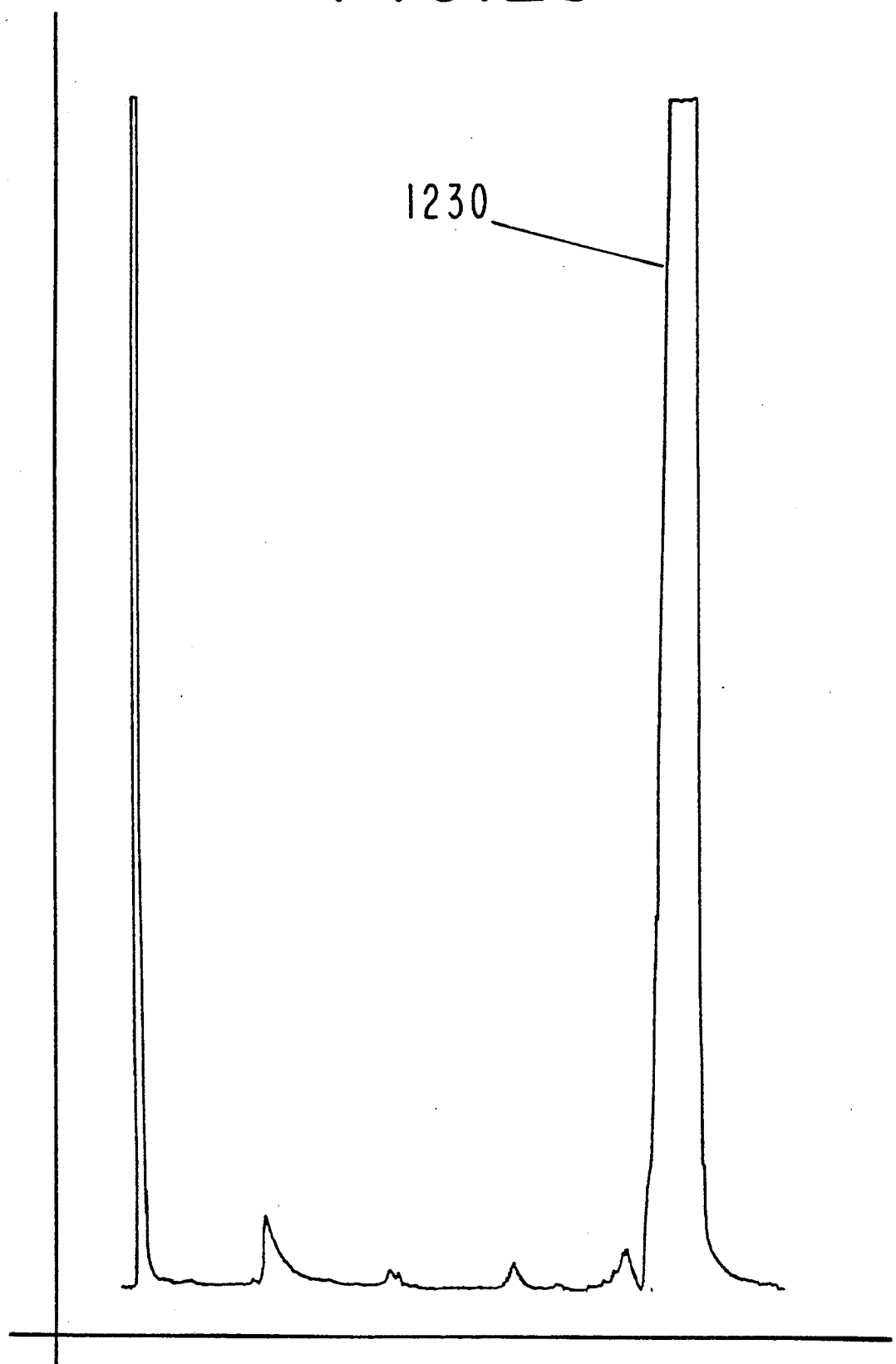

FIG. 23 is the GC profile for the reaction product of Example II(b) containing the compounds having the structures:

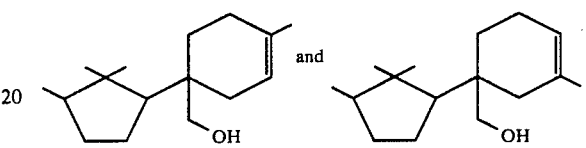

Figure 24:
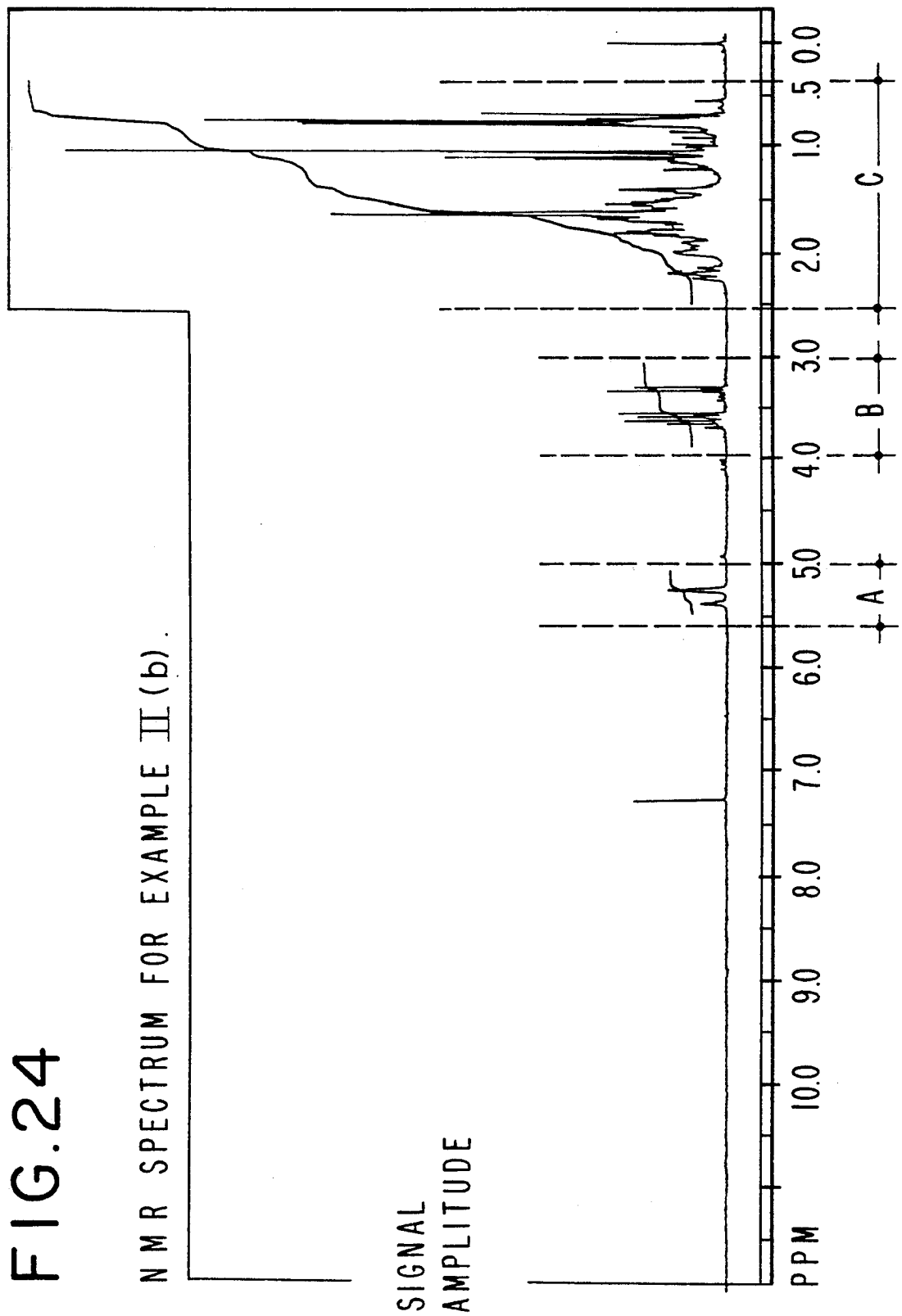

FIG. 24 is the NMR spectrum for the mixture of compounds having the structures:

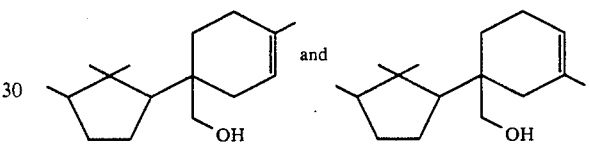

prepared according to Example II(b).

FIGS. 24A, 24B and 24C are enlargements of sections "A", "B" and "C", respectively, of the NMR spectrum of FIG. 24.

FIG. 25 is the infra-red spectrum for the mixture of compounds having the structures:

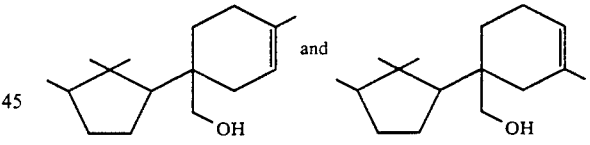

prepared according to Example II(b).

Figure 26:
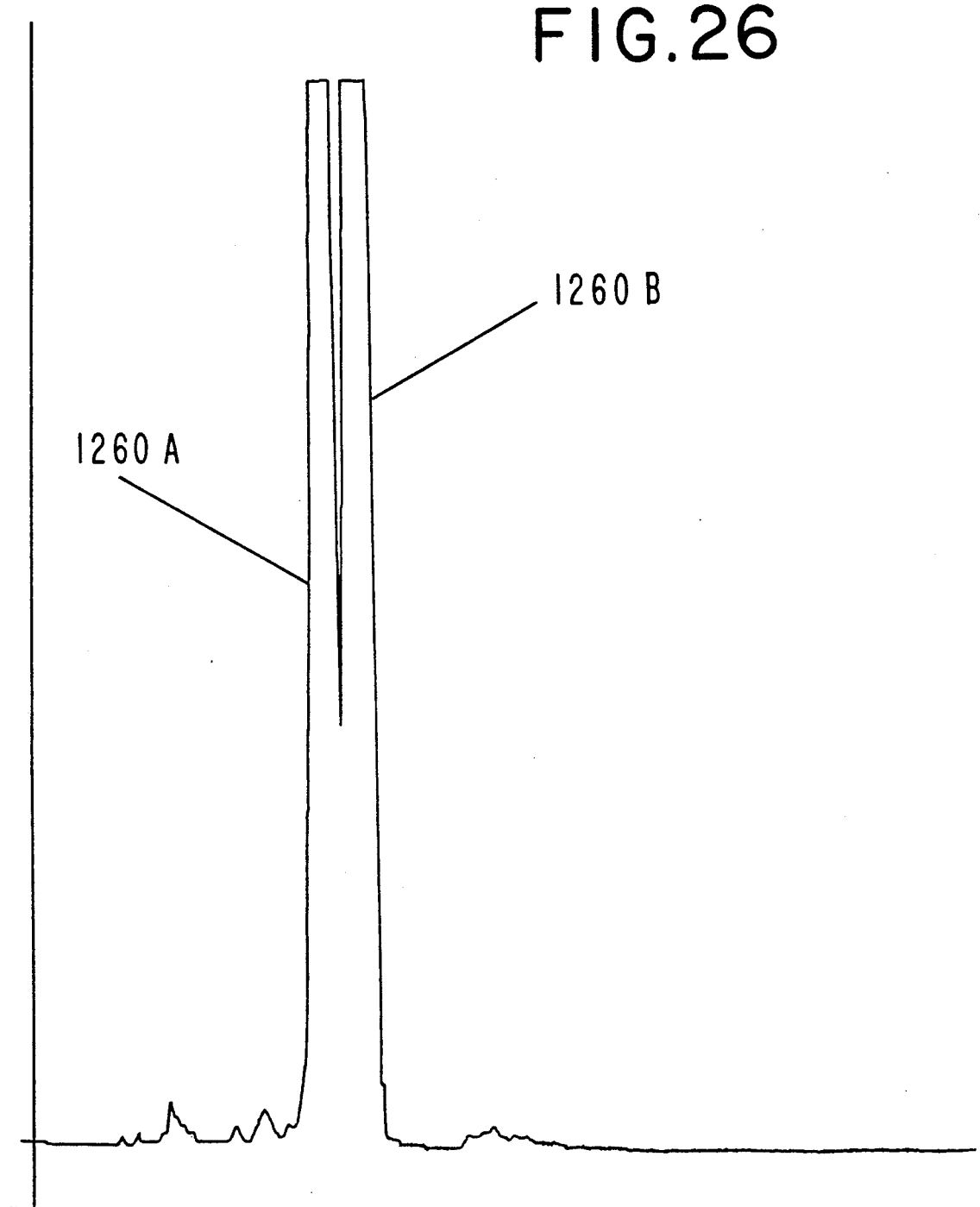

FIG. 26 is the GC profile for the mixture of compounds having the structures:

and

prepared according to Example II(c)(Conditions: SE-30 column programmed at 150°-220° C. at 8° C. per minute).

Figure 27:
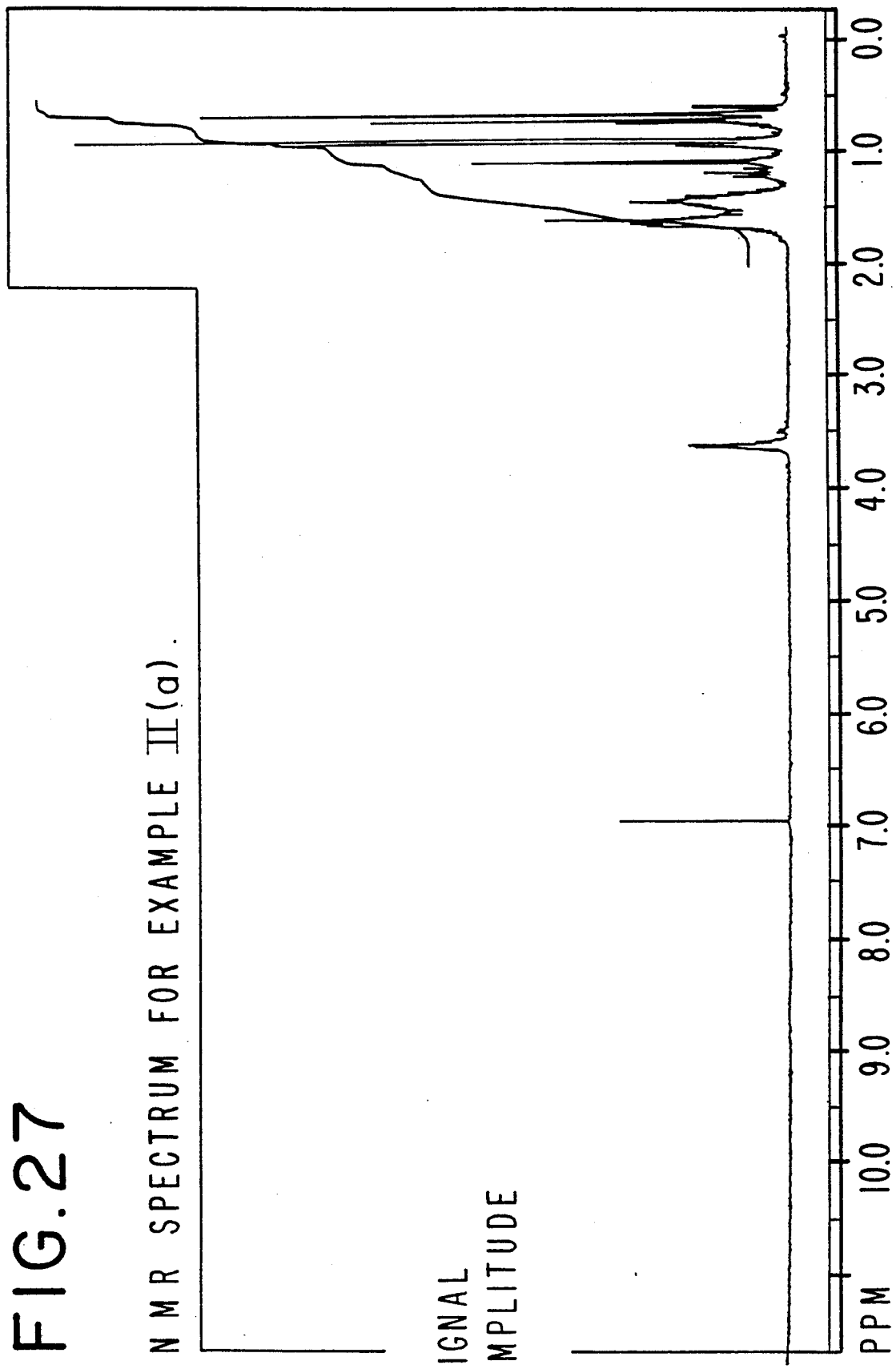

FIG. 27 is the NMR spectrum for the mixture of compounds having the structures:

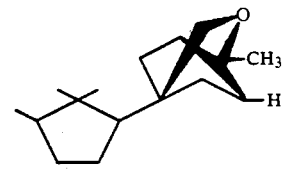

and

prepared according to Example II(c).

Figure 28:
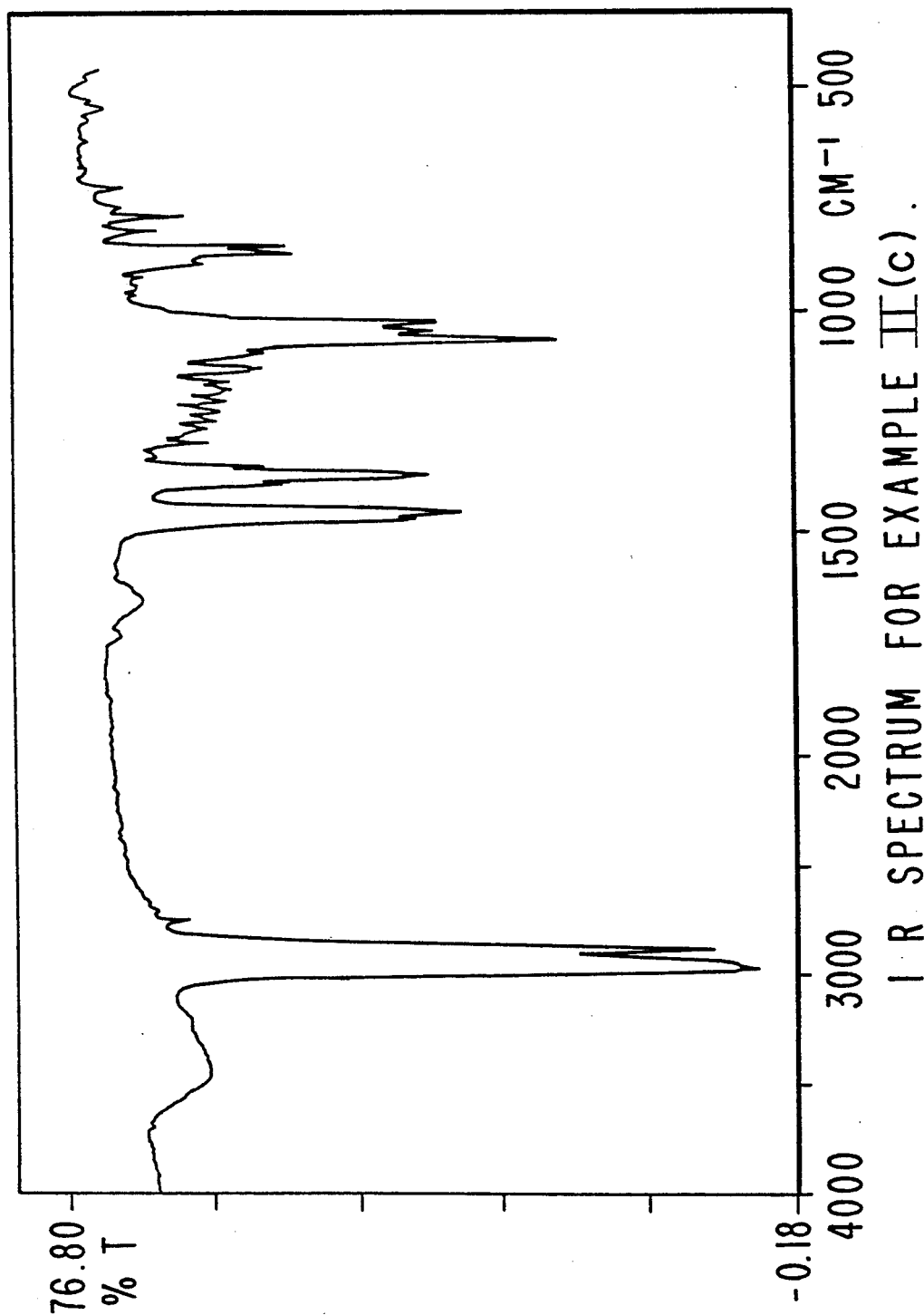

FIG. 28 is the infra-red spectrum for the mixture of compounds having the structures:

and

prepared according to Example II(c).

FIG. 29 is a partial side elevation and partial sectional view of an apparatus for forming polymer pellets scented with one of the perfume compositions or perfumery materials of our invention containing at least one of the substituted cyclopentyl oxabicyclooctanes, cyclopentyl vinyl pyrans, cyclopentylformylcyclohexenes and cyclopentylhydroxymethyl cyclohexenes of our invention.

FIG. 30 is a section taken on line 30—30 of FIG. 29.

DETAILED DESCRIPTION OF THE DRAWINGS

Figure 1:
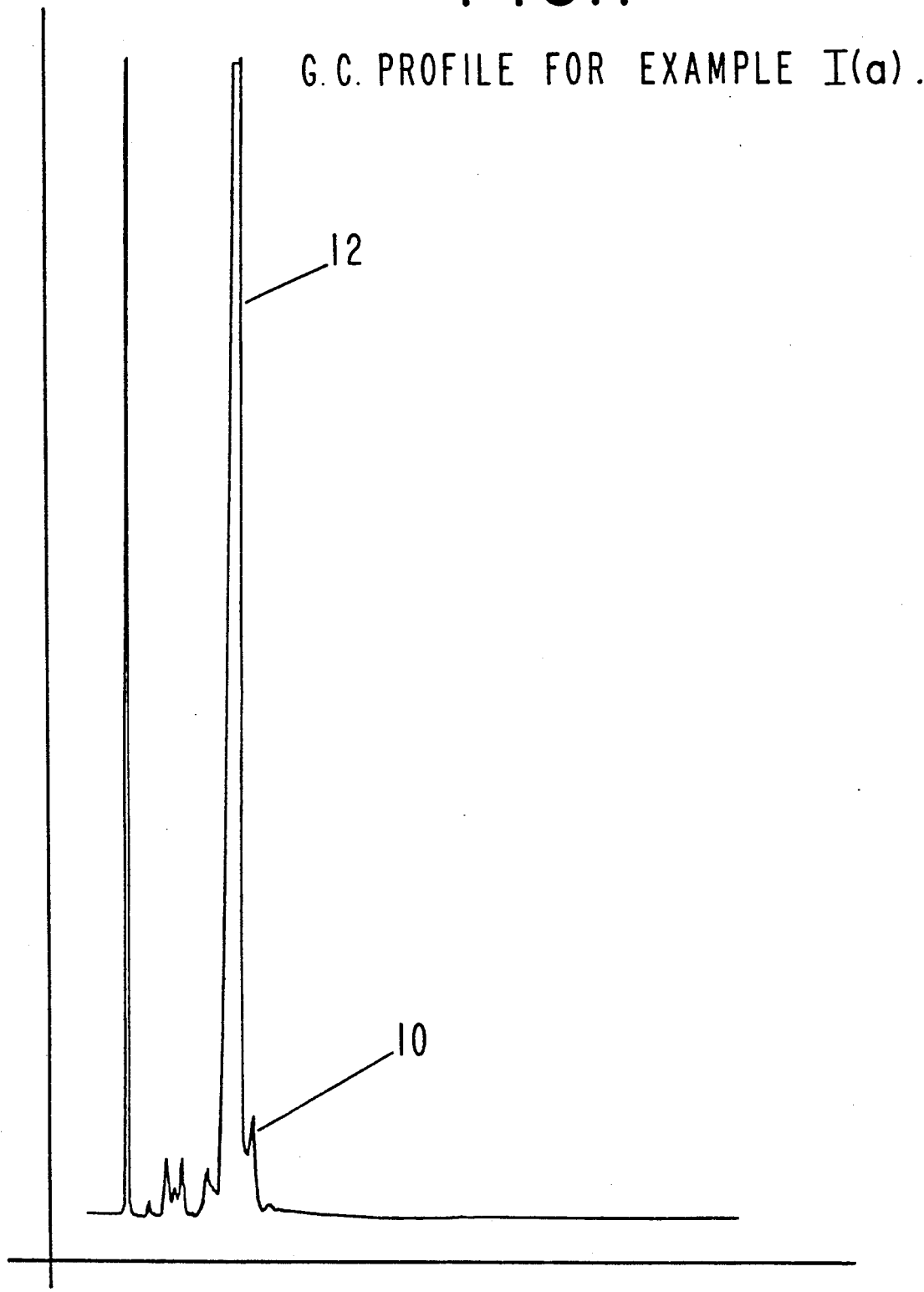
FIG. 1 is the GLC profile for the reaction product of Example I(a) containing the compound having the structure.

FIG. 1 is the GC profile of the reaction product of Example I(a)(Conditions: SE-30 column programmed at 150°-220° C. at 8° C. per minute). The peak indicated by reference numeral 12 is the peak for the compound having the structure:

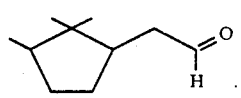

The peak indicated by reference numeral 10 is the peak for the compound having the structure:

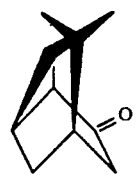

FIG. 4 is the GC profile for the reaction product of Example I(b)(Conditions: SE-30 column programmed at 150°-220° C. at 8° C. per minute). The peak indicated by reference numeral 42 is the peak for the compound having the structure:

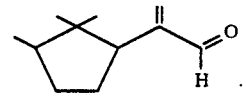

The peak indicated by reference numeral 40 is for the compound having the structure:

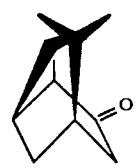

FIG. 7 is the GC profile for the reaction product of Example I(c)(Conditions: SE-30 column programmed at 150°-220° C. at 8° C. per minute). The peak indicated by reference numeral 70 is the peak for the compound having the structure:

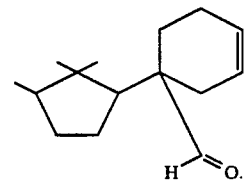

The peak indicated by reference numeral 72 is the peak for the compound having the structure:

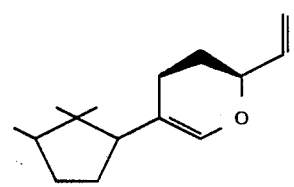

FIG. 11 is the GC profile for the reaction product of Example I(d)(Conditions: SE-30 column programmed at 150°-220° C. at 8° C. per minute). The peak indicated by reference numeral 110 is the peak for the compound having the structure:

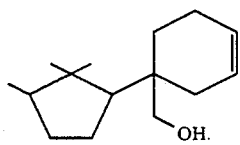

FIG. 14 is the GC profile for the reaction product of Example I(e)(Conditions: SE-30 column programmed at 220° C. isothermal). The peaks indicated by reference numerals 140A and 140B are for the two compounds having the structures:

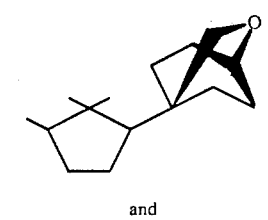

and

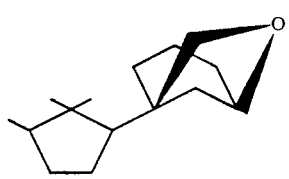

FIG. 17 is the GC profile for the reaction product of Example II(a)(Conditions: Carbowax column programmed at 150°-220° C. at 8° C. per minute). The peak indicated by reference numeral 172 is the peak for the compound having the structure:

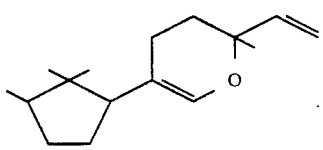

The peak indicated by reference numeral 174 is the peak for the compound having the structure:

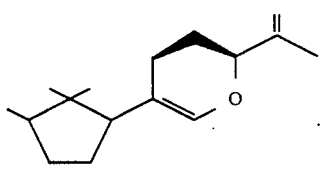

The peaks indicated by reference numerals 170A and 170B are for the two compounds having the structures:

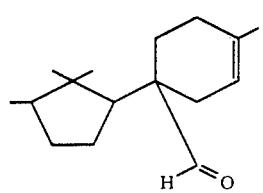

and

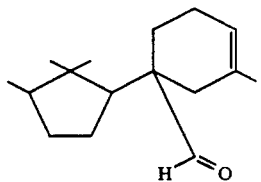

FIG. 23 is the GC profile for the reaction product of Example II(b)(Conditions: SE-30 column programmed at 150°-220° C. at 8° C. per minute). The peak indicated by reference numeral 1230 is the peak for the mixture of compounds having the structures:

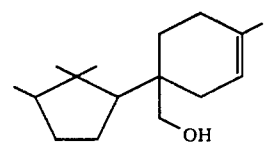

and

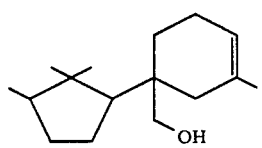

FIG. 26 is the GC profile for the reaction product of Example II(c)(Conditions: SE-30 column programmed at 150°-220° C. at 8° C. per minute). The peaks indicated by reference numerals 1260A and 1260B are for the compounds having the structures:

and

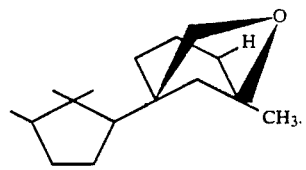

Referring to FIGS. 29 and 30, the apparatus used in producing polymeric fragrances containing at least one of the substituted cyclopentyl oxabicyclooctanes, cyclopentyl vinyl pyrans cyclopentylformylcyclohexenes and cyclopentylhydroxymethyl cyclohexenes of our invention comprises a device for forming scented polyolefin (for example) pellets which comprises a vat or container 212 into which a mixture of polyolefin such as polyethylene or an aromatic substance or scented material containing or consisting of at least one of the substituted cyclopentyl oxabicyclooctanes, cyclopentyl vinyl pyrans cyclopentylformylcyclohexenes and cyclopentylhydroxymethyl cyclohexenes is placed. The container is closed by an air tight lid 228 and clamped to the container by bolts 265. A stirrer 273 traverses the lid or cover 228 in air tight manner and is rotated in a suitable manner. A surrounding cylinder 212 having heating coils which are supplied with electric current through cable 224 from a rheostat or control 216 is operated to maintain the temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 200°–280° F. The heater 212A is operated to maintain the upper portion of the container 212 within a temperature range of from 250°–350° F. The bottom portion of the container 212 is heated by means of heating coils 212A heated through a control 220 connected thereto through a connecting wire 226 to maintain the lower portion of the container 212 within a temperature range of from 250°–350° F.

Thus, polymer (e.g., polyolefin) added to the container 212 is heated from 10–12 hours whereafter a scent or aroma imparting material which contains or consists of at least one of the substituted cyclopentyl oxabicyclooctanes, cyclopentyl vinyl pyrans cyclopentylformylcyclohexenes and cyclopentylhydroxymethyl cyclohexenes of our invention is quickly added to the melt. The material must be compatible with the polyolefin and forms a homogeneous liquid melt therewith. The scented material containing or consisting or at least one of the substituted cyclopentyl oxabicyclooctanes, cyclopentyl vinyl pyrans cyclopentylformylcyclohexenes and cyclopentylhydroxymethyl cyclohexenes of our invention is of a type for the particular aroma desired and formulated specifically for the scenting purpose for which the polyolefin will be employed. The aromatic materials in some instances in solid or powdered form may be employed or added to the polyolefin in the container 212. Generally about 10–30% by weight of the scenting material is added to the polyolefin.

After the scent imparting material containing or consisting of at least one of the substituted cyclopentyl oxabicyclooctanes, cyclopentyl vinyl pyrans cyclopentylformylcyclohexenes and cyclopentylhydroxymethyl cyclohexenes of our invention is added to the container 212, the mixture is stirred for a few minutes, for example, 5–15 minutes and maintained within the temperature ranges indicated previously by the heating coils 212A and 218, respectively. The controls 216 and 220 are connected through cables 224 and 226 to a suitable supply of electric current for supplying the power for heating purposes. The controls 216 and 220 are connected to the heating coils 212A, respectively, through wires 214 and 222.

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g., polyolefin) and aroma imparting material mixture (containing or consisting of at least one of the substituted cyclopentyl oxabicyclooctanes, cyclopentyl vinyl pyrans cyclopentylformylcyclohexenes and cyclopentylhydroxymethyl cyclohexenes of our invention) will continuously drop through the orifices 234 downwardly from the conduit 232. During this time, the temperature of the polymer (e.g., polyolefin) containing an aroma mixture containing or consisting of at least one of the substituted cyclopentyl oxabicyclooctanes, cyclopentyl vinyl pyrans cyclopentylformylcyclohexenes and cyclopentylhydroxymethyl cyclohexenes of our invention in the container 212 is accurately controlled so that a temperature in the range of from about 210°–275° F. will exist in the conduit 232. The regulation of the temperature through the control 216 and the control 220 is essential in order to insure temperature balance to provide for the continuous dropping or dripping of molten polymer (e.g., polyolefin) and scenting material containing or consisting of at least one of the substituted cyclopentyl oxabicyclooctanes, cyclopentyl vinyl pyrans cyclopentylformylcyclohexenes and cyclopentylhydroxymethyl cyclohexenes of our invention through the orifices 234 at a rate which will insure the formation of droplets 236 which will fall downwardly onto a moving conveyor belt 238 trained to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with water or some other suitable cooling liquid in order to insure the rapid cooling of each of the pellets. The pellets 244 are then collected from the container 245 and utilized in a process as illustrated, infra.

A feature of this aspect of the process of our invention is in the provision for moistening the conveyor belt 238 to insure rapid formation of the solid polymer (e.g., polyolefin)-scented pellets 244 without sticking to the belt. The belt 238 is advantageously of a material which will not normally stick to a melted plastic but the moistening means 248 insures a sufficiently cold temperature of the belt surface for the adequate formation of the pellets 244. The moistening means comprises a container 250 which is continuously fed with water 254 to maintain a level for moistening a sponge element 256 which bears against the exterior surface of the belt 238.

Thus, a perfumed polymer consisting of a microporous polymer (e.g., polyethylene) is created which has intimately admixed therewith in the interstices thereof an aroma augmenting, enhancing or imparting quantity of at least one of the substituted cyclopentyl oxabicyclooctanes, cyclopentyl vinyl pyrans cyclopentylformylcyclohexenes and cyclopentylhydroxymethyl cyclohexenes of our invention.

THE INVENTION

The instant invention provides substituted cyclopentyl oxabicyclooctanes, cyclopentyl vinyl pyrans cyclopentylformylcyclohexenes and cyclopentylhydroxymethyl cyclohexenes defined according to the generic structures:

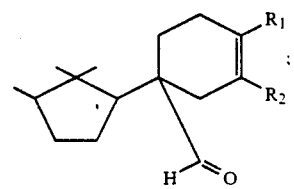

-continued

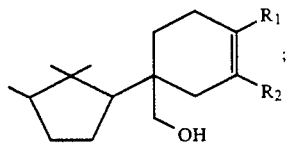

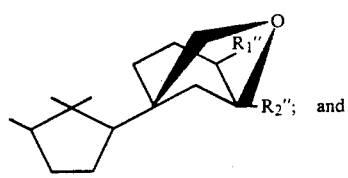

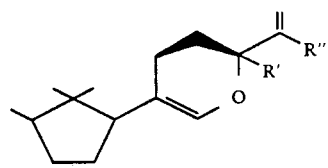

wherein $R_1$, $R_2$, $R'$, $R''$, $R_1'$, $R_2'$, $R_1''$ and $R_2''$, are the same or different and each represents hydrogen or methyl with the provisos that:
(i) $R_1$ and $R_2$ are not both methyl;
(ii) $R'$ and $R''$ are not both methyl;
(iii) when $R_1'$ is methyl, then $R_2'$ is hydrogen; and
(iv) when $R_2''$ is methyl, then $R_1''$ is hydrogen.

The substituted cyclopentyl oxabicyclooctanes, cyclopentyl vinyl pyrans cyclopentylformylcyclohexenes and cyclopentylhydroxymethyl cyclohexenes of our invention are useful in augmenting or enhancing the aroma of perfume compositions, colognes and perfumed articles (including but not limited to solid or liquid, anionic, cationic, nonionic or zwitterionic detergents, perfumed polymers, fabric softener compositions, fabric softener articles, cosmetic powders, hair preparations and the like).

Briefly, our invention also employs the substituted cyclopentyl oxabicyclooctanes, cyclopentyl vinyl pyrans cyclopentylformylcyclohexenes and cyclopentylhydroxymethyl cyclohexenes of our invention to impart, augment and/or enhance balsamic, piney, sweaty, animalic, woody, ambery, fruity, musky, tobacco-like, sweet, apple-like, lactonic and coumarin aromas, with piney, ozoney, balsamic, herbaceous, buttery, ambery, orris-like, woody, plum-like, sweaty and animalic topnotes and "air dried clothing" undertones in or to perfume compositions, colognes and perfumed articles (e.g., solid or liquid, anionic, cationic, nonionic or zwitterionic detergents, perfumed polymers, fabric softener compositions, fabric softener articles, hair preparations, cosmetic powders and the like).

Briefly, the substituted cyclopentyl oxabicyclooctanes, cyclopentyl vinyl pyrans cyclopentylformylcyclohexenes and cyclopentylhydroxymethyl cyclohexenes of our invention may be prepared by first forming a compound having the structure:

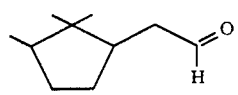

by means of hydrogenating a compound having the structure:

with hydrogen using, for example, a palladium on carbon catalyst according to the reaction:

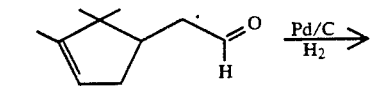

The product having the structure:

is then reacted with formaldehyde according to the reaction:

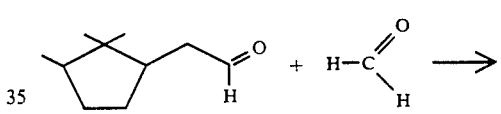

in order to produce the compound having the structure:

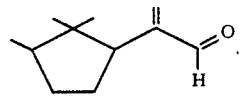

The compound having the structure:

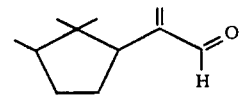

is then reacted with a diene/dienophile having the structure:

according to the reaction:

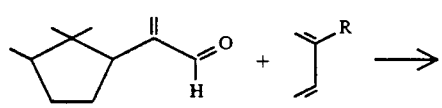

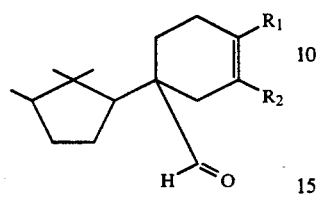

wherein R is hydrogen or methyl and $R_1$ and $R_2$ are the same or different hydrogen or methyl. When this reaction is carried out a side product is formed also having good organoleptic utilites defined according to the generic structure:

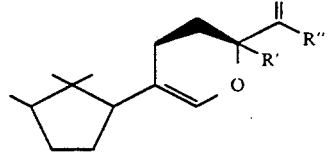

wherein R' and R" are the same or diffferent hydrogen or methyl. R' and R", in separate compounds in the mixture are each methyl when R is methyl. The compound having the structure:

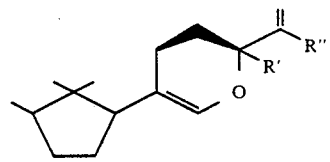

is formed under a mechanism where the compound having the structure:

acts as a dienophile and the compound having the structure:

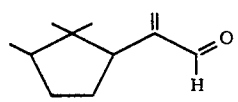

acts as the "diene".

The resulting compounds having the structure:

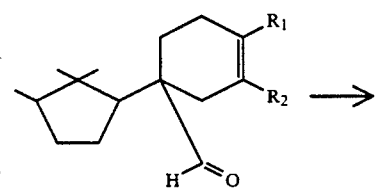

are then reduced according to the reaction:

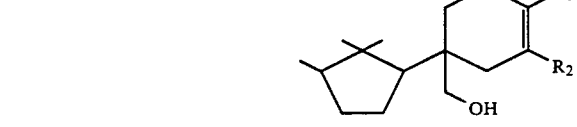

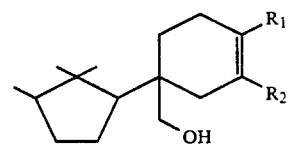

whereby compounds defined according to the structure:

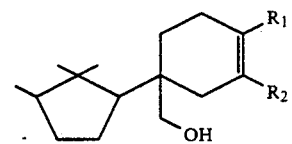

are formed. Again, when R is hydrogen, then $R_1$ and $R_2$ are each hydrogen; and when R is methyl, a mixture is formed where one of $R_1$ or $R_2$ is methyl in one of the compounds of the mixture and the other of $R_1$ or $R_2$ is methyl in the other of the compounds of the mixture.

The resulting compounds have the structure:

are then caused to be cyclized to form compounds having the structures:

and

-continued

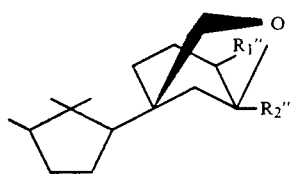

according to the reaction:

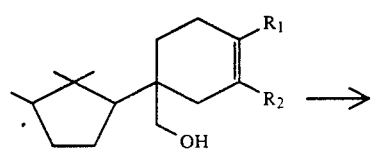

having the reaction mechanism:

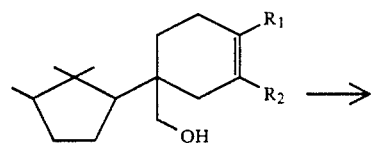

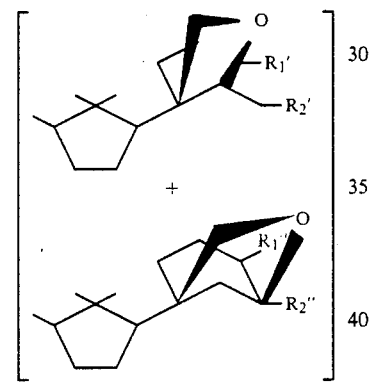

-continued

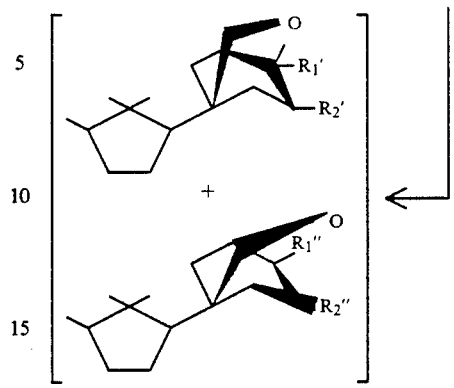

It should be noted, that when $R_1$ or $R_2$ are methyl, the carbon having the methyl group (carbon atom "3" or carbon atom "4") is more electrophilic and nucleophilic attack of the oxygen of the hydroxyl moiety takes place at the most electrophilic carbon atom. Hence, in the mixture of compounds having the structures:

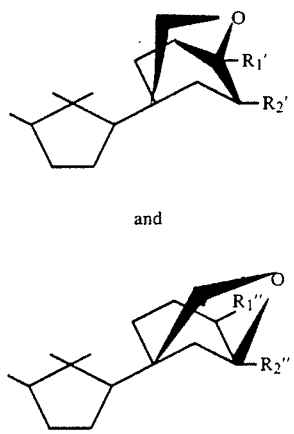

and when $R_1'$ is methyl then $R_2'$ is hydrogen and when $R_2''$ is methyl, $R_1''$ is hydrogen and in such case, $R_1''$ is always hydrogen and $R_2'$ is always hydrogen.

With respect to each of the reactions set forth above whereby compounds having the structures:

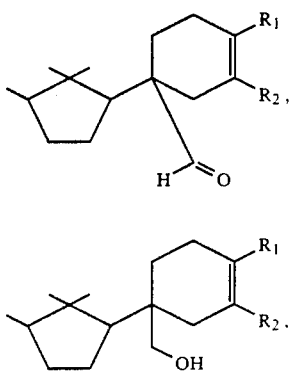

-continued

and

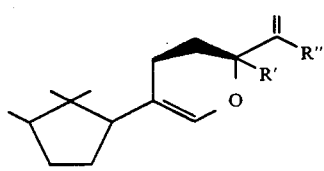

are produced, at the end of each of the reactions, the reaction products can be used as is for a subsequent reaction or the reaction products can be used for their organoleptic properties (and thus fractionally distilled).

Starting with the production of the compounds having the structures:

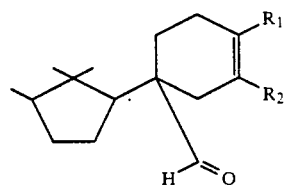

and

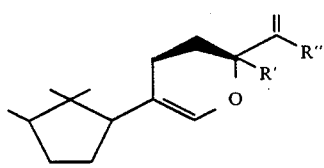

the reaction sequences; that is, the Diels-Alder reaction, the alcohol formation reactions and the cyclization reactions are carried out using the conditions substantially the same as those set forth in U.S. Pat. Nos. 4,269,862 and 4,267,067, the specifications for which are incorporated by reference herein. The conditions set forth in the above stated U.S. Pat. Nos. 4,269,862 and 4,267,067 are for the reaction schemes:

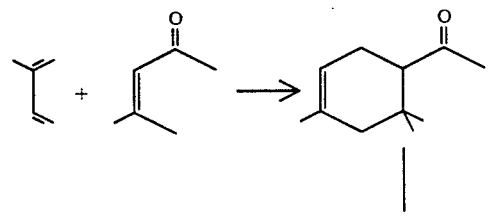

-continued

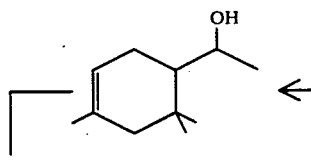

and said conditions are set forth at column 5, lines 50-68; column 6, lines 1-62; column 7, lines 1-68 and column 8, lines 1-34 of U.S. Pat. No. 4,269,862 as well as column 5, lines 41-68; column 6, column 7 and column 8, lines 1-29 of U.S. Pat. No. 4,267,067.

Thus, the Diels-Alder reaction of the aldehyde having the structure:

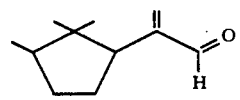

with the conjugated diene having the structure:

is, in general, a procedure known in the prior art. The reaction may be carried out in the presence of Lewis acid catalysts such as zinc chloride, aluminum chloride or aluminum bromide; or it may be carried out in the absence of catalysts at higher temperatures, e.g., up to 200° C. When carrying out the Diels-Alder reaction in the presence of catalysts, lower temperatures, e.g., −10° C. up to 30° C. may be utilized. The Diels-Alder reaction may be carried out in the presence of or in the absence of a solvent. When solvents are used it is preferred to use such solvents as xylene or tetralin.

The reaction of the cyclohexene carboxaldehyde to form the cyclohexene carbinol followed by cyclization may take place in a single reactor without separation of the cyclohexene carbinol or may take place in two separate reactors with separation of the cyclohexene carbinol followed by cyclization.

When carrying out that part of the reaction sequence whereby the cyclohexene carboxaldehyde defined according to the structure:

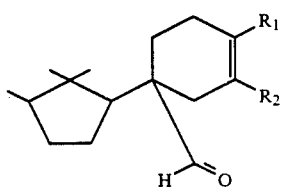

is reduced to form the compounds defined according to the structure:

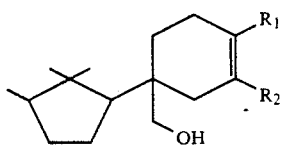

according to the reaction:

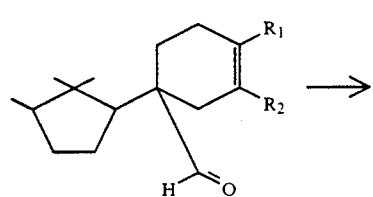

the reaction takes place in the presence of a solvent such as isopropenol, tetrahydrofuran, dioxane, diethyl ether, or diglyme using a reducing agent such as sodium borohydride, lithium aluminum hydride or VITRIDE® (registered trademark for the compound having the structure:

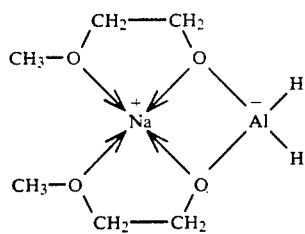

of the Hexcel Company).

The reaction:

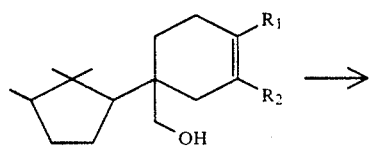

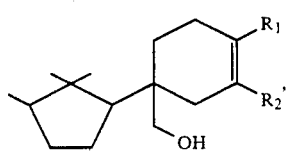

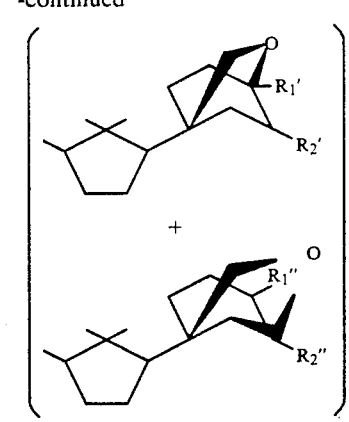

the "cyclization reaction" takes place using a cyclization reagent such as methane sulphonic acid or sulfuric acid.

The following table sets forth specific products produced according to our invention and their perfumery properties:

TABLE I

| Product Identification | Perfumery Property |
|---|---|
| The compound having the structure: [structure] prepared according to Example I (c), fraction 2. | A woody, sweet, balsamic aroma with "air dried clothing" undertones and buttery topnotes. |
| The compound having the structure: [structure] prepared according to Example I (d). | A piney, woody, sweaty, animalic aroma with piney, woody, sweaty and animalic topnotes. |
| The mixture of compounds having the structures: [structure] and [structure] prepared according to Example II (a). | A woody aroma with woody, ozoney, balsamic and herbaceous topnotes. |

TABLE I-continued

| Product Identification | Perfumery Property |
|---|---|
| distillation fraction 3. | |
| The mixture of compounds having the structures:<br>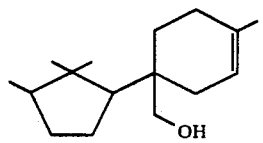<br>and<br>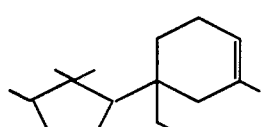<br>prepared according to Example II (b). | A woody aroma with woody and ozoney topnotes. |
| The mixture of compounds having the structures:<br>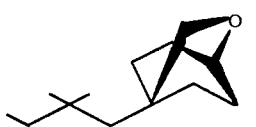<br>and<br><br>prepared according to Example I (e). bulked distillation fractions 8-10. | A woody, ambery, fruity, musky and tobacco-like aroma with ambery, orris-like and woody topnotes. |
| The mixture of compounds having the structures:<br><br>and<br><br>prepared according to Example II (c), bulked distillation fractions 8-11. | An ambery, woody and sweet aroma profile with woody, plum-like, sweaty and animalic topnotes. |
| The compound having the structure: | A fruity, apple-like, sweet, lactonic and coumarin-like |

TABLE I-continued

| Product Identification | Perfumery Property |
|---|---|
| 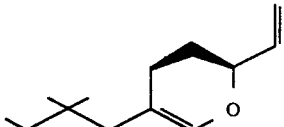<br>prepared according to Example I (c). | aroma profile. |

At least one of the substituted cyclopentyl oxabicyclooctanes, cyclopentyl vinyl pyrans cyclopentylformylcyclohexenes and cyclopentylhydroxymethyl cyclohexenes of our invention and one or more auxiliary perfume ingredients including, for example, alcohols (other than the alcohols of our invention), aldehydes (other than the aldehydes of our invention), ketones, terpenic hydrocarbons, esters, lactones, ethers (other than the cyclic ethers of our invention), natural essential oils and synthetic essential oils may be admixed so that the combined odors of the individual components produce a pleasant and desired fragrance, particularly and preferably in the balsamic and pine fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, at least one of the substituted cyclopentyl oxabicyclooctanes, cyclopentyl vinyl pyrans cyclopentylformylcyclohexenes and cyclopentylhydroxymethyl cyclohexenes of our invention can be used to alter, modify or enhance the aroma characteristics of a perfume composition, for example, by utilizing or moderating the olfactory reaction contributed by another ingredient in the composition.

The amount of one or more of the substituted cyclopentyl oxabicyclooctanes, cyclopentyl vinyl pyrans cyclopentylformylcyclohexenes and cyclopentylhydroxymethyl cyclohexenes of our invention which will be effective in the perfume composition as well as in the perfumed articles and colognes depends on many factors including the other ingredients, their amounts and the effects which are desired. It has been found that perfume compositions containing as little as 0.01% of at least one of the substituted cyclopentyl oxabicyclooctanes, cyclopentyl vinyl pyrans cyclopentylformylcyclohexenes and cyclopentylhydroxymethyl cyclohexenes of our invention or even less (e.g., 0.005%) can be used to impart, augment or enhance balsamic, piney, sweaty, animalic, woody, ambery, fruity, musky, tobacco-like, sweet, apple-like, lactonic and coumarinic aromas with piney, ozoney, balsamic, herbaceous, buttery, ambery, orris-like, woody, plum-like, sweaty and animalic topnotes and "air dried clothing" undertones to soaps, cosmetics, solid or liquid, anionic, cationic, nonionic or zwitterionic detergents, fabric softener compositions, fabric softener articles, hair preparations and perfumed polymers. The amount employed can range up to 70% of the fragrance components and will depend on considerations of cost, nature of the end product, the effect desired on the finished product and the particular fragrance sought. In fact, as much as 100% of the fragrance component can be the substituted cyclopentyl oxabicyclooctanes, cyclopentyl vinyl pyrans cyclopentylformylcyclohexenes and cyclopentylhydroxymethyl cyclohexenes of our invention in certain specific instances, e.g., the formation of specific perfumed polymers on an industrial level.

One or more of the substituted cyclopentyl oxabicyclooctanes, cyclopentyl vinyl pyrans cyclopentylformylcyclohexenes and cyclopentylhydroxymethyl cyclohexenes of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions and sun screens; powders such as talcs, dusting powders, face powders and the like. When used as (an) olfactory component(s) as little as 1% of at least one of the substituted cyclopentyl oxabicyclooctanes, cyclopentyl vinyl pyrans cyclopentylformylcyclohexenes and cyclopentylhydroxymethyl cyclohexenes of our invention or even less will suffice to impart intense and substantive balsamic, piney, sweaty, animalic, woody, ambery, fruity, musky, tobacco-like, sweet, apple-like, lactonic, and coumarin-like aromas, with piney, ozoney, balsamic, herbaceous, buttery, ambery, orris-like, woody, plum-like, sweaty and animalic topnotes with "air dried clothing" undertones to pine formulations and xobalsamic formulations. Generally, no more 20% of at least one of the substituted cyclopentyl oxabicyclooctanes, cyclopentyl vinyl pyrans cyclopentylformylcyclohexenes and cyclopentylhydroxymethyl cyclohexenes of our invention based on the ultimate end product is required in the perfume composition; however, perfume compositions can in their entireties in certain specific instances only contain the substituted cyclopentyl oxabicyclooctanes, cyclopentyl vinyl pyrans cyclopentylformylcyclohexenes and cyclopentylhydroxymethyl cyclohexenes of our invention.

Accordingly, in perfume compositions and colognes from about 0.01% up to about 100% of the perfume composition may be at least one of the substituted cyclopentyl oxabicyclooctanes, cyclopentyl vinyl pyrans cyclopentylformylcyclohexenes and cyclopentylhydroxymethyl cyclohexenes of our invention. In perfumed articles, the quantity of at least one of the substituted cyclopentyl oxabicyclooctanes, cyclopentyl vinyl pyrans cyclopentylformylcyclohexenes and cyclopentylhydroxymethyl cyclohexene of our invention in a perfumed article may vary from about 0.005% up to about 25% of the perfumed article. In the case of perfumed polymers, for example, up to 50% by weight of the substituted cyclopentyl oxabicyclooctanes, cyclopentyl vinyl pyrans cyclopentylformylcyclohexenes and cyclopentylhydroxymethyl cyclohexenes of our invention can be used. In the cases of solid or liquid, anionic, cationic, nonionic or zwitterionic detergents up to 8% of the substituted cyclopentyl oxabicyclooctanes, cyclopentyl vinyl pyrans cyclopentylformylcyclohexenes and cyclopentylhydroxymethyl cyclohexene of our invention can be used.

In addition, the perfume composition or fragrance composition of our invention can contain a vehicle or carrier for at least one of the substituted cyclopentyl oxabicyclooctanes, cyclopentyl vinyl pyrans cyclopentylformylcyclohexenes and cyclopentylhydroxymethyl cyclohexenes of our invention. The vehicle can be a liquid such as a non-toxic alcohol such as ethyl alcohol or a non-toxic glycol such as propylene glycol or the like. The carrier can also be an absorbent solid, such as a gum (e.g., gum arabic, xanthan gum, or guar gum or mixtures of same) or components for encapsulating the composition (such as gelatin as by means of coacervation or such as a urea/formaldehyde prepolymer when a polymeric wall is intended to be formed around a liquid perfume composition center).

The following Examples I and II serve to illustrate the processes for preparing the compounds of our invention and compounds useful for their organoleptic properties. Examples following Example II, (Examples III, et seq.) illustrate organoleptic utilities of the substituted cyclopentyl oxabicyclooctanes, cyclopentyl vinyl pyrans cyclopentylformylcyclohexenes and cyclopentylhydroxymethyl cyclohexenes of our invention.

All parts and percentages given herein are by weight unless otherwise specified.

EXAMPLE I(a)

Preparation of Dihydrocampholenic Aldehyde

Reaction

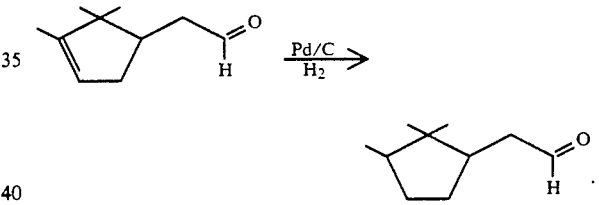

Into a 4 liter zipper autoclave equipped with hydrogen feed line is placed 2500 grams of the compound having the structure:

The autoclave is closed and the temperature is raised to 85°–87° C. The hydrogenation takes place at a pressure of 100 psig for a period of four hours. The amount of catalyst (palladium on carbon, 5% palladium) used in the autoclave is 125 grams.

At the end of the reaction, the reaction mass is filtered and distilled to yield a 50% product. The distillation data is as follows:

| Fraction No. | Vapor Temp. (°C.) | Liquid Temp. (°C.) | Vacuum mm/Hg. Pressure |
|---|---|---|---|
| 1 | 30/73 | 74/80 | 10.9/10.9 |
| 2 | 76 | 90 | 9.00 |
| 3 | 98 | 158 | 1.74 |
| 4 | 130 | 160 | 0.730. |

EXAMPLE I(b)

Preparation of Alpha Methylene Dihydrocampholenic Aldehyde

Reaction

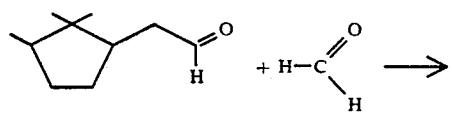

Into a 12 liter reaction vessel equipped with stirrer, thermometer, reflux condenser and heating mantle are placed 66 grams of dibutyl amine and 31 grams of acetic acid. The contents of the reaction flask are heated to 35° C. Over a period of 5 minutes while maintaining the reaction mass at 30°-35° C., 1182 grams (14.6 moles) of formaldehyde are added to the reaction mass. With stirring, the reaction mass is heated to 70°-75° C. Over a 2.25 hour period while maintaining the reaction mass at 70°-75° C., 1545 grams of the compound having the structure:

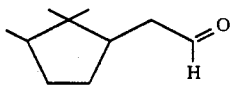

prepared according to Example I(a) are added to the reaction mass The reaction mass is then maintained at a temperature of 74° C. with stirring for a period of four hours. The reaction mass is then cooled to room temperature. The organic phase is separated from the aqueous phase. The organic phase is washed with 1 liter of saturated sodium chloride and filtered through anhydrous magnesium sulfate. The resulting organic layer is then fractionally distilled to yield 1298 grams of product (94% yield). The distillation data is as follows:

| Fraction No. | Vapor Temp. (°C.) | Liquid Temp. (°C.) | Vacuum mm/Hg. Pressure |
|---|---|---|---|
| 1 | 31/61 | 81/94 | 64/18.5 |
| 2 | 87 | 100 | 16.6 |
| 3 | 140 | 200 | 10.1. |

The analytical data for the resulting product having the structure:

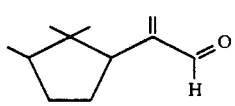

is set forth in FIGS. 5 and 6, described, supra.

EXAMPLE I(c)

Diels-Alder Reaction

Reaction

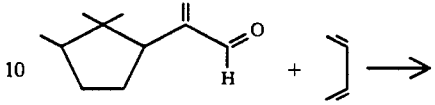

(with by-product formation of:

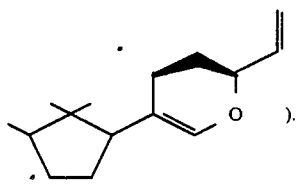

).

Into a 2 liter Parr Bomb is placed 667 grams (4.02 moles) of the compound having the structure:

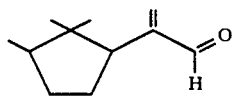

(prepared according to Example I(b) and 344 grams (6.93 moles) of butadiene having the structure:

The Parr Bomb is closed and the contents are heated to a temperature of 150° C. while maintaining the pressure of the Parr Bomb at 260 psig. The Parr Bomb with stirring is maintained at 260 psig and 150° C. for a period of eight hours. At the end of the eight hour period, the Parr Bomb is cooled and opened and the reaction product is fractionally distilled yielding the following fractions:

| Fraction No. | Vapor Temp. (°C.) | Liquid Temp. (°C.) | Vacuum mm/Hg. Pressure |
|---|---|---|---|
| 1 | 21/71 | 44/104 | 10.5/6.15 |
| 2 | 120 | 125 | 25.3 |
| 3 | 81 | 200 | 1.49. |

The resulting products having the structures:

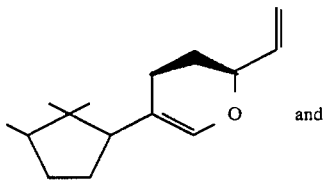

and

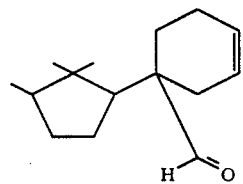

are analyzed by means of NMR and IR analyses. The analyses are set forth in FIGS. 8, 9 and 10.

EXAMPLE I(d)

Preparation of Cyclopentyl Hydroxymethyl Cyclohexene

Reaction

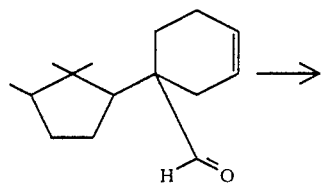

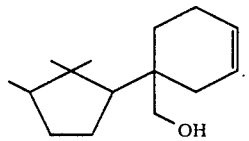

Into a 3 liter reaction vessel equipped with stirrer, thermometer, reflux condenser and heating mantle are placed 32 grams (0.85 moles) of sodium borohydride; 300 ml isopropyl alcohol and 300 ml water. While maintaining the reaction mass at 51° C. over a period of 1.5 hours, 373 grams (1.70 moles) of the compound having the structure:

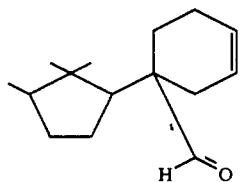

prepared according to Example I(c) is added to the reaction mass. The reaction mass is then maintained at 51° C. at atmospheric pressure for a period of nine hours. The reaction mass is then separated into two phases; an organic phase and an aqueous phase. The organic phase is washed with 500 ml saturated sodium chloride and filtered through anhydrous magnesium sulfate and then concentrated to yield 326.6 grams (1.47 moles) of 87% crude product. The resultant product is fractionally distilled to yield the compound having the structure:

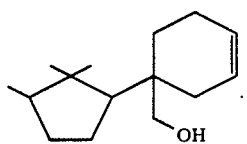

Analytical data for the compound having the structure:

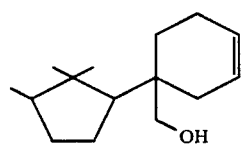

is set forth in FIG. 12 (NMR spectrum) and FIG. 13 (IR spectrum) described, supra.

EXAMPLE I(e)

Preparation of Substituted Cyclpentyloxabicyclooctane

Reaction

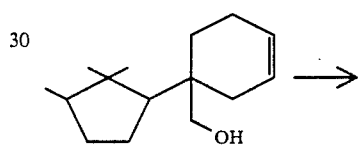

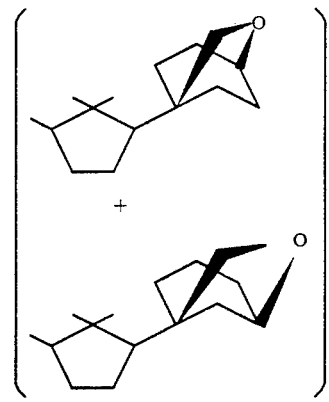

Into a 3 liter reaction vessel equipped with stirrer, thermometer, reflux condenser and heating mantle are placed 279 grams (0.87 moles) of the compound having the structure:

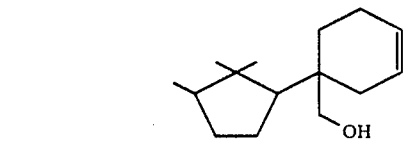

prepared according to Example I(d); 14.6 grams (0.15 moles) of methane sulphonic acid and 250 ml nitromethane. The reaction mass is heated to reflux (102° C.) and maintained at reflux for a period of 6.5 hours. At the end of the 6.5 hour period, an additional 2.1 grams (0.022 moles) of methane sulphonic acid is added to the reaction mass. The reaction mass is continued to be refluxed for a period of 4.5 hours. At the end of the 4.5 hour period, the reaction mass is combined with an additional 2.1 grams of methane sulphonic acid and refluxed for another four hours. The reaction mass is then cooled to room temperature and admixed with 500 ml 10% aqueous sodium bicarbonate with stirring. The organic phase is separated from the aqueous phase. The organic phase is washed with 500 ml saturated sodium chloride and filtered through anhydrous magnesium sulfate to yield 158 grams of product. The reaction product is then fractionally distilled yielding the following fractions:

| Fraction No. | Vapor Temp. (°C.) | Liquid Temp. (°C.) | Vacuum mm/Hg. Pressure |
|---|---|---|---|
| 1 | 43/46 | 49/90 | 15.0/3.32 |
| 2 | 103 | 130 | 0.623 |
| 3 | 110 | 132 | 0.640 |
| 4 | 111 | 135 | 0.720 |
| 5 | 110 | 136 | 0.635 |
| 6 | 110 | 138 | 0.600 |
| 7 | 111 | 140 | 0.585 |
| 8 | 113 | 143 | 0.580 |
| 9 | 114 | 146 | 0.590 |
| 10 | 116 | 154 | 0.605 |
| 11 | 115 | 170 | 0.745 |
| 12 | 105 | 200 | 0.918. |

The resulting product having the structures:

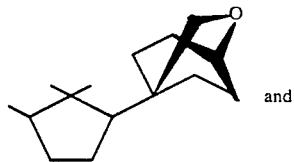

and

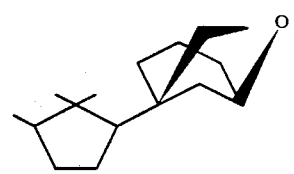

(mixture) is analyzed and the analytical data is set forth in FIGS. 15 and 16, described, supra.

EXAMPLE II(a)

Diels-Alder Reaction

Reaction

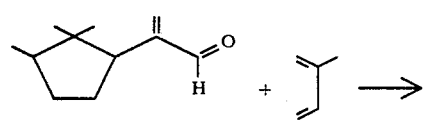

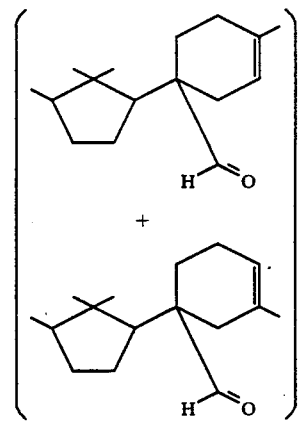

(with the production of the compounds having the structures:

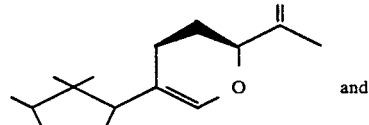

and

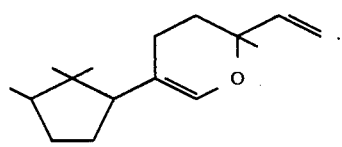

as side products).

Into a 2 liter Parr Bomb are placed 365 grams (6.29 moles) of isoprene having the structure:

and 800 grams (4.19 moles) of the compound having the structure:

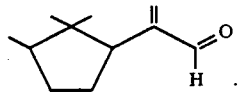

The Parr Bomb is sealed and heated to 150° C. While maintaining the Parr Bomb at 150° C., the Parr Bomb is pressurized to 140 psig. The Parr Bomb is maintained at 140 psig and 150°–175° C. for a period of five hours. At the end of the five hour period, the Parr Bomb is cooled and filtered through anhydrous magnesium sulfate to yield 697 grams of product.

The resulting product is distilled through a fractionation column with the following distillation data:

| Fraction No. | Vapor Temp. (°C.) | Liquid Temp. (°C.) | Vacuum mm/Hg. Pressure |
|---|---|---|---|
| 1 | 24/104 | 59/148 | 10.4/10.3 |

-continued

| Fraction No. | Vapor Temp. (°C.) | Liquid Temp. (°C.) | Vacuum mm/Hg. Pressure |
|---|---|---|---|
| 2 | 136 | 154 | 9.48 |
| 3 | 95 | 205 | 2.50. |

The resulting product is a mixture of compounds having the structures:

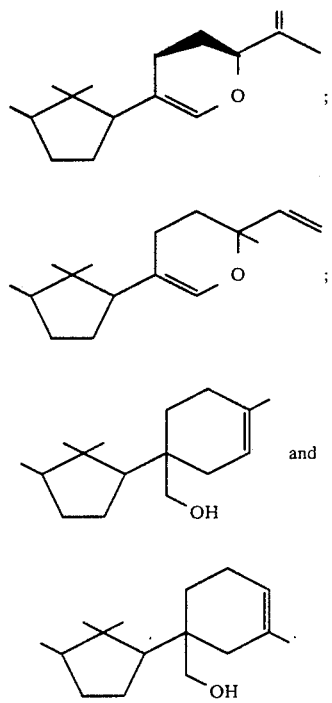

The compounds having the structures:

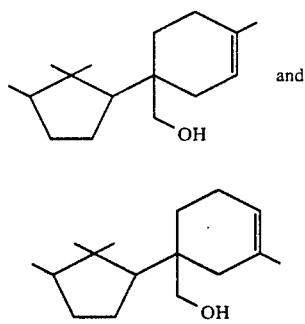

are separated from the compounds having the structures:

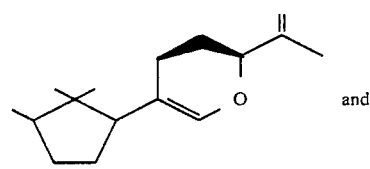

-continued

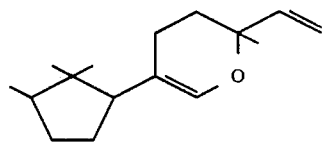

Analytical data for these compounds is set forth in FIGS. 18, 19, 20, 21 and 22. The analytical data is explained, supra.

EXAMPLE II(b)

Production of Cyclopentylhydroxymethyl Cyclohexene Derivatives

Reaction

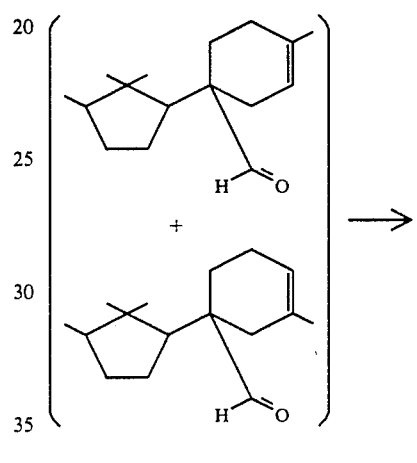

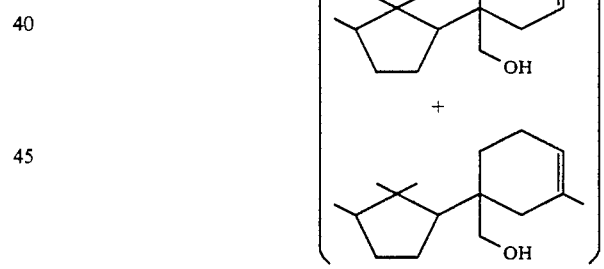

Into a 5 liter reaction flask equipped with stirrer, thermometer, reflux condenser and heating mantle are placed 37 grams of sodium borohydride; 400 ml isopropyl alcohol and 400 ml water. The resulting mixture is heated to 40° C. While maintaining the reaction mass at 40° C., over a period of 2.25 hours, 467 grams (1.96 moles) of the mixture of compounds having the structures:

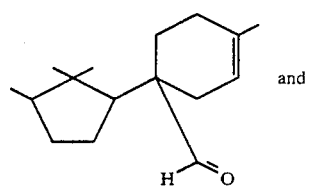

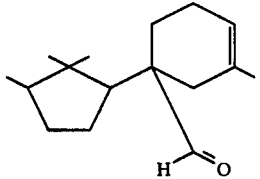

is added to the reaction mass. The reaction mass is then stirred at a temperature of 40° C. for a period of 8.5 hours.

At the end of the 8.5 hour period, the reaction mass exists in two phases; an organic phase and an aqueous phase. The organic phase is washed with 500 ml water followed by 500 ml saturated aqueous sodium chloride. The organic phase is then filtered through anhydrous magnesium sulfate to yield 428 grams of crude product.

The resultant product is analyzed as a mixture of compounds having the structures:

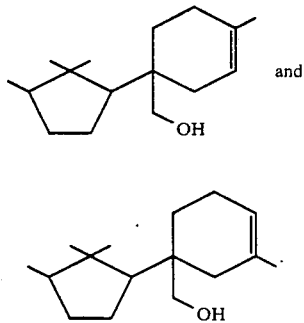

The analytical data is set forth in FIGS. 24 and 25 (NMR and IR spectra, respectively). The analytical data is interpreted and explained, supra.

EXAMPLE II(c)

Production of Cyclopentyl Oxabicyclooctane Derivatives

Reaction

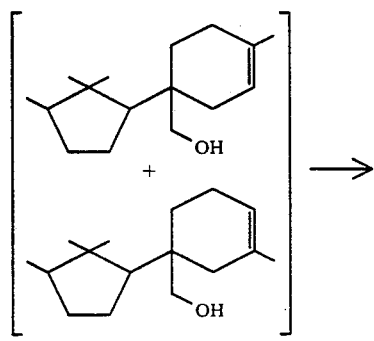

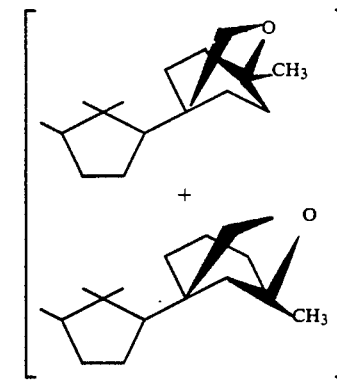

Into a 3 liter reaction flask equipped with stirrer, thermometer and reflux condenser are placed 410 grams (1.74 moles) of the mixture of compounds having the structures:

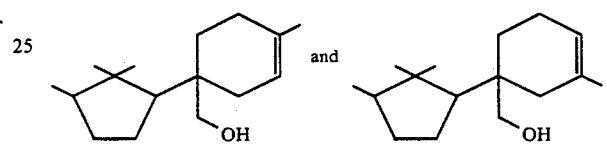

prepared according to Example II(b) and 400 ml nitromethane. The reaction mixture is heated to 40°-50° C. Over a period of five minutes while maintaining the reaction temperature at 40°-50° C., 6.7 grams (0.070 moles) of methane sulphonic acid is added to the reaction mass. The reaction mass is then heated to 75° C. and maintained at 75° C. for a period of six hours with stirring. At the end of the six hour period, the reaction mass is cooled and 400 ml of 10% aqueous sodium bicarbonate is added to the reaction mass. The reaction mass is then cooled to room temperature and remains at room temperature for a period of twelve hours. At the end of the twelve hour period, 200 ml toluene is added to the reaction mass. The reaction mass now exists in two phase; an organic phase and an aqueous phase. The organic phase is washed with 500 ml saturated aqueous sodium chloride. The organic phase is then filtered through anhydrous magnesium sulfate to yield 351 grams of crude product containing compounds having the structures:

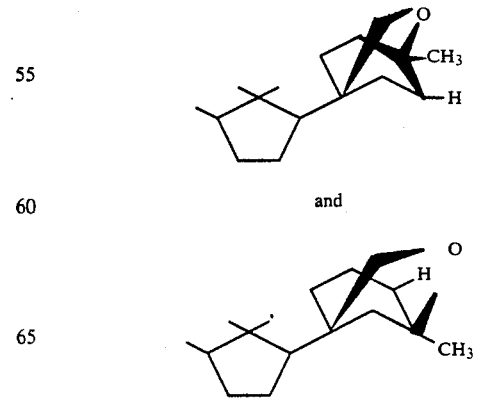

The resulting product is distilled on a fractionation column yielding the following fractions:

| Fraction No. | Vapor Temp. (°C.) | Liquid Temp. (°C.) | Vacuum mm/Hg. Pressure |
|---|---|---|---|
| 1 | 23/75 | 34/85 | 9.5/5.0 |
| 2 | 114 | 120 | 1.88 |
| 3 | 115 | 118 | 1.88 |
| 4 | 115 | 120 | 1.88 |
| 5 | 111 | 120 | 1.55 |
| 6 | 107 | 118 | 1.09 |
| 7 | 109 | 119 | 5.76 |
| 8 | 106 | 118 | 0.382 |
| 9 | 105 | 119 | 0.385 |
| 10 | 104 | 119 | 0.385 |
| 11 | 105 | 120 | 0.385 |
| 12 | 105 | 142 | 0.605 |
| 13 | 96 | 166 | 0.390 |

The resulting product is analyzed via NMR and IR spectra. The analytical data is set forth in FIGS. 27 and 28. The interpretation of FIGS. 27 and 28 is set forth, supra.

EXAMPLE III

The substituted cyclopentyl oxabicyclooctanes, cyclopentyl vinyl pyrans cyclopentylformylcyclohexenes and cyclopentylhydroxymethyl cyclohexenes of our invention prepared according to Examples I(c), I(d) and I(e), inclusive, have very long-lasting woody, sweet, balsamic, ambery, fruity, musky, tobbaco-like, piney, sweaty and animalic aromas, with ambery, orris-like, woody, piney, sweaty, animalic and buttery topnotes and "air dried clothing" undertones which may be utilized to a great extent in inexpensive functional products. The following pine fragrance demonstrates the use of these materials in perfume compositions.

| Ingredients | Parts by Weight | | |
|---|---|---|---|
| | III (a) | III (b) | III (c) |
| Isobornyl acetate | 100 | 100 | 100 |
| Camphor | 10 | 10 | 10 |
| Terpineol | 25 | 25 | 25 |
| Fir Balsam Absolute (50% in Diethyl Phthalate) | 20 | 20 | 20 |
| Coumarin | 4 | 4 | 4 |
| Linalool | 30 | 30 | 30 |
| Anethol | 2 | 2 | 2 |
| Fenchyl Alcohol | 10 | 10 | 10 |
| Lemon Terpenes Washed | 50 | 50 | 50 |
| Borneol | 5 | 5 | 5 |
| Galbanum Oil | 5 | 5 | 5 |
| Turpentine Russian | 150 | 150 | 150 |
| Pinus Pimilionus | 50 | 50 | 50 |
| Eucalyptol | 50 | 50 | 50 |
| Mixture of compounds having the structures: 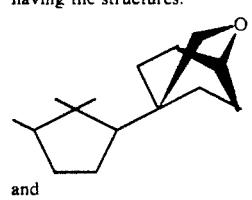 and  prepared according to Example I (e), bulked distillation fractions 8–10. | 12 | 0 | 0 |
| Compound having the structure: 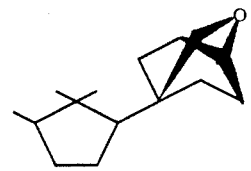 prepared according to Example I (c), distillation fraction 2. | 0 | 12 | 0 |
| Compound having the structure: 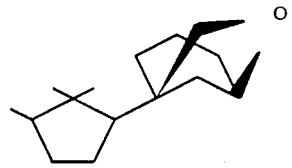 prepared according to Example I (d). | 0 | 0 | 12 |

The mixture of compounds having the structures:

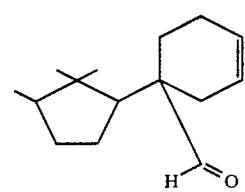

and prepared according to Example I(e) imparts to this pine formulation woody, ambery, fruity, musky and tobacco-like undertones, with ambery, orris-like and woody topnotes. Accordingly, the perfume composition of Example III(a) can be described as "piney aroma with woody, ambery, fruity, musky and tobacco-like undertones and ambery, orris-like and woody topnotes".

The compound having the structure:

prepared according to Example I(c) imparts to this piney formulation woody, sweet, balsamic and "air dried clothing" undertones with buttery topnotes. Accordingly, the perfume formulation of Example III(b) can be described as "a piney aroma, with woody, sweet, balsamic and "air dried clothing" undertones and buttery topnotes".

The compound having the structure:

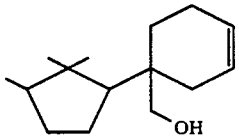

produced according to Example I(d) imparts to this piney aroma woody, sweaty, animalic undertones, with woody, sweaty and animalic topnotes. Accordingly, the perfume composition of Example III(c) can be described as "a piney aroma, with woody, sweaty and animalic undertones and woody, sweaty and animalic topnotes".

EXAMPLE IV

The substituted cyclopentyl oxabicyclooctanes, cyclopentyl vinyl pyrans cyclopentylformylcyclohexenes and cyclopentylhydroxymethyl cyclohexenes of our invention produced according to Example II(a), II(b) and II(c) have very long lasting ambery, woody and sweet aromas, with woody, plum-like, sweaty, animalic, ozoney, balsamic and herbaceous topnotes, which may be utilized to a great extent in expensive functional products. The following pine fragrance demonstrates the use of these materials in perfume compositions:

| Ingredients | Parts by Weight | | |
|---|---|---|---|
| | IV (a) | IV (b) | IV (c) |
| Isobornyl acetate | 100 | 100 | 100 |
| Camphor | 10 | 10 | 10 |
| Terpineol | 25 | 25 | 25 |
| Fir Balsam Absolute (50% in Diethyl Phthalate) | 20 | 20 | 20 |
| Coumarin | 4 | 4 | 4 |
| Linalool | 30 | 30 | 30 |
| Anethol | 2 | 2 | 2 |
| Fenchyl Alcohol | 10 | 10 | 10 |
| Lemon Terpenes Washed | 50 | 50 | 50 |
| Borneol | 5 | 5 | 5 |
| Galbanum Oil | 5 | 5 | 5 |
| Turpentine Russian | 150 | 150 | 150 |
| Pinus Pimilionus | 50 | 50 | 50 |
| Eucalyptol | 50 | 50 | 50 |
| The mixture of compounds having the structures: and prepared according to Example II (c). | 12 | 0 | 0 |
| The mixture of compounds having the structures: bulked distillation fractions 8-11. and produced according to Example II (a), distillation fraction 3. | 0 | 12 | 0 |
| The mixture of compounds having the structures: and prepared according to Example II (b). | 0 | 0 | 12 |

The mixture of compounds having the structures:

prepared according to Example II(c) imparts to this piney fragrance ambery, woody and sweet undertones, with woody, plum-like, sweaty and animalic topnotes. Accordingly, the perfume composition of Example IV(a) can be described as "a piney aroma, with ambery, woody and sweet undertones and woody, plum-like, sweaty and animalic topnotes".

The mixture of compounds having the structures:

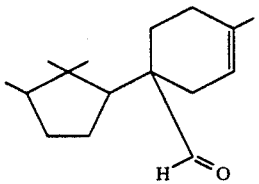

and

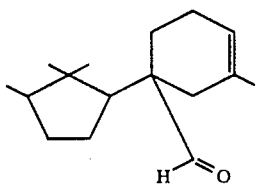

prepared according to Example II(a) imparts woody undertones with woody, ozoney, balsamic and herbaceous topnotes. Accordingly, the perfume composition of Example IV(b) can be described as a "piney aroma with a woody undertone and woody, ozoney, balsamic and herbaceous topnotes".

The mixture of compounds having the structures:

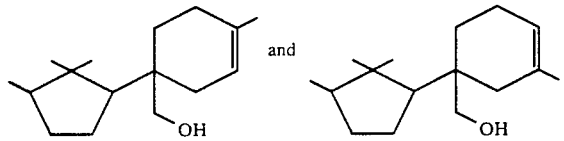

prepared according to Example II(b) imparts to this piney fragrance woody undertones with woody and ozoney topnotes. Accordingly, the perfume composition of Example IV(c) can be described as "a piney aroma with woody undertones and woody and ozoney topnotes".

EXAMPLE IV(d)

A perfume composition containing the following ingredients was prepared:

| Ingredients | Parts by Weight IV (d) |
| --- | --- |
| Isobornyl acetate | 100 |
| Camphor | 10 |
| Terpineol | 25 |
| Fir Balsam Absolute | 20 |
| (50% in Diethyl Phthalate) | |
| Coumarin | 4 |
| Linalool | 30 |
| Anethol | 2 |
| Fenchyl Alcohol | 10 |
| Lemon Terpenes Washed | 50 |
| Borneol | 5 |
| Galbanum Oil | 5 |
| Turpentine Russian | 150 |
| Pinus Pimilionus | 50 |
| Eucalyptol | 50 |
| The compound having the structure: | 12 |

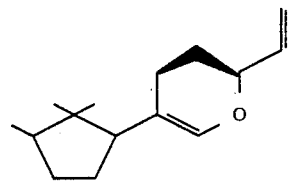

prepared according to Example I (c).

The compound having the structure:

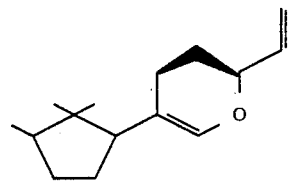

prepared according to Example I(c) imparts to this piney aroma fruity, applie-like, sweet, lactonic and coumarin-like undertones. Accordingly, the perfume composition of Example IV(d) can be described as "a piney aroma, with fruity, apple-like, sweet, lactonic and coumarin-like undertones".

EXAMPLE V

A Cosmetic Powder Preparation

A cosmetic powder is prepared by mixing in a ball mill 100 grams of talcum powder with 0.25 grams of one of the substances set forth in Table II below containing at least one of the substituted cyclopentyl oxabicyclooctanes, cyclopentyl vinyl pyrans cyclopentylformylcyclohexenes and cyclopentylhydroxymethyl cyclohexenes of our invention. Each of the cosmetic powders has an excellent aroma as described in Table II below.

TABLE II

| Perfumery Substance | Aroma Nuance |
| --- | --- |
| The compound having the structure:<br>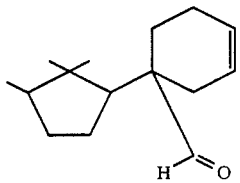<br>produced according to Example I (c), distillation fraction 2. | A woody, sweet, balsamic aroma, with "air dried clothing" undertones and buttery topnotes. |

TABLE II-continued

| Perfumery Substance | Aroma Nuance |
|---|---|
| The compound having the structure: 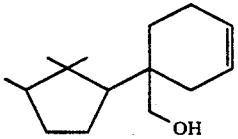 prepared according to Example I (d). | A piney, woody, sweaty and animalic aroma, with piney, woody, sweaty and animalic topnotes. |
| Mixture of compounds having the structures: 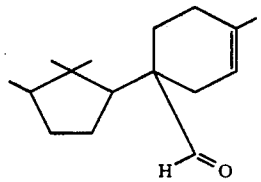 and 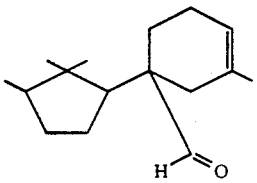 prepared according to Example II (a), distillation fraction 3. | A woody aroma, with woody, ozoney, balsamic and herbaceous topnotes. |
| Mixture of compounds having the structures: 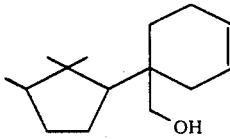 and 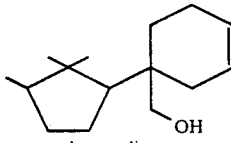 prepared according to Example II (b). | A woody aroma, with woody and ozoney topnotes. |
| Mixture of compounds having the structures:  and 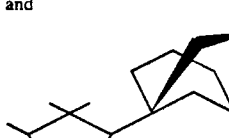 prepared according to Example I (e), bulked distillation fractions 8-10. | A woody, ambery, fruity, musky and tobacco-like aroma, with ambery, orris-like and woody topnotes. |
| Mixture of compounds | An ambery, woody and sweet aroma. |

TABLE II-continued

| Perfumery Substance | Aroma Nuance |
|---|---|
| having the structures:  and  prepared according to Example II (c), bulked distillation fractions 8-11. | with woody, plum-like, sweaty and animalic topnotes. |
| The compound having the structure: 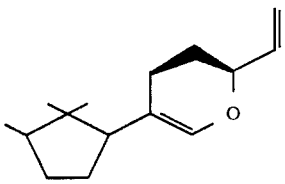 prepared according to Example I (c). | A fruity, apple-like, sweet, lactonic and coumarin-like aroma. |
| Perfume composition of Example III (a). | A piney aroma, with woody, ambery, fruity, musky and tobacco-like undertones and ambery, orris-like and woody topnotes. |
| Perfume composition of Example III (b). | A piney aroma, with woody, sweet, balsamic and "air dried clothing" undertones and buttery topnotes. |
| Perfume composition of Example III (c). | A piney aroma, with woody, sweaty and animalic undertones and woody, sweaty and animalic topnotes. |
| Perfume composition of Example IV (a). | A piney aroma, with ambery, woody and sweet undertones and woody plum-like, sweaty and animalic topnotes. |
| Perfume composition of Example IV (b). | A piney aroma with woody undertones and woody, ozoney, balsamic and herbaceous topnotes. |
| Perfume composition of Example IV (c). | A piney aroma, with woody undertones and woody and ozoney topnotes. |
| Perfume composition of Example IV (d). | A piney aroma, with fruity, apple-like, sweet, lactonic and coumarin-like undertones. |

EXAMPLE VI

Perfumed Liquid Detergent

Concentrated liquid detergents (Lysine salt of n-dodecylbenzene sulfonic acid as more specifically described in U.S. Pat. No. 3,948,818 issued on Apr. 6, 1976, the specification for which is incorporated herein) with aromas as set forth in Table II of Example V, supra, are prepared containing 0.10%, 0.15%, 0.20%, 0.25%, 0.30% and 0.35% of each of the substances of Table II of Example V. They are prepared by adding and homogeneously admixing the appropriate quantity of one of the substances of Table II of Example V in the liquid detergent. The detergents all possess excellent aromas as set forth in Table II of Example V.

EXAMPLE VII

Preparation of a Cologne and Handkerchief Perfume

The substances set forth in Table II of Example V are incorporated separately into colognes at concentrations of 2.0%, 2.5%, 3.0%, 3.5% 4.0%, 4.5% and 5.0% in 75%, 80%, 85% and 90% aqueous food grade ethanol solutions; and into handkerchief perfumes at concentrations of 15%, 20%, 25% and 30%, in 80%, 85%, 90% and 95% aqueous food grade ethanol solutions. Distinctive aromas as set forth in Table II of Example V, supra, are imparted to the colognes and to the handkerchief perfume compositions at levels indicated.

EXAMPLE VIII

Preparation of Soap Composition

One hundred grams of soap chips (IVORY ®, produced by the Procter & Gamble Company, of Cincinnati, Ohio) are admixed with 1 gram of each of the substances of Table II of Example V, supra, until homogeneous compositions are obtained. The homogeneous compositions are each separated then heated under 3 atmospheres pressure at 180° C. for a period of 3 hours and the resulting liquid samples are placed in soap molds. The resulting soap cake, on cooling, manifest excellent long-lasting aromas as set forth in Table II of Example V, supra.

EXAMPLE IX

Preparation of Solid Detergent Compositions

Detergents are prepared from the following ingredients according to Example II of Canadian Letters Patent No. 1,007,948 the specification for which is incorporated by reference herein:

| Ingredients | Parts by Weight |
| --- | --- |
| NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of the substances of Table II of Example V. Each of the detergent samples has excellent aromas as set forth in Table II of Example V.

EXAMPLE X

Drier-Added Fabric Softener Article

Utilizing the procedure of Example II at column 15 of U.S. Pat. No. 3,623,396, the specification for which is incorporated by reference herein, a non-woven cloth substrate useful as a drier-added fabric softening article of manufacture is prepared wherein the substrate, the substrate coating and the outer coating and the perfuming material are as follows:
1. A water "dissolvable" paper ("Dissolvo Paper");
2. Adogen 448 (m.p. about 140° F.) as the substrate coating; and
3. An outer coating have the following formulation (m.p. about 105° F.);
57% $C_{20-22}$HAPS
22% isopropyl alcohol
20% antistatic agent
1% of one of the substances of Table II of Example V, supra.

Fabric softening compositions containing one of the substances of Table II of Example V consist essentially of a substrate having a weight of about 3 grams per 100 square inches of substrate coating having a weight of about 1.85 grams per 100 square inches; and an outer coating having a weight of about 1.4 grams per 100 square inches thereby providing a total aromatized substrate and outer coating weight ratio of about 1:1 by weight of the substrate.

Pleasant aromas as set forth in Table II of Example V are imparted to the head space in the dryer on operation thereof using the said drier-added fabric softening non-woven fabric.

What is claimed is:

1. One or more substituted cyclopentyl oxabicyclooctanes and/or cyclopentyl vinyl pyrans having a structure selected from the group consisting of:

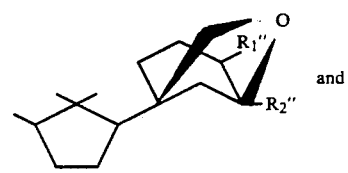

and

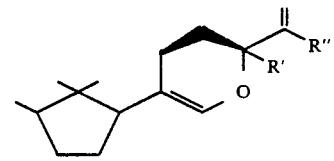

wherein $R'$, $R''$, $R_1'$, $R_2'$, $R_1''$ and $R_2''$ each represents hydrogen or methyl with the provisos that:
(i) $R'$ and $R''$ are not both methyl;
(ii) when $R_1'$ is methyl, $R_2'$ is hydrogen; and
(iii) when $R_2''$ is methyl, $R_1''$ is hydrogen.

2. One or more compounds of claim 1 defined according to the structure:

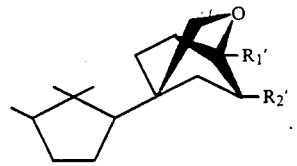

3. One or more compounds of claim 1 defined according to the structure:

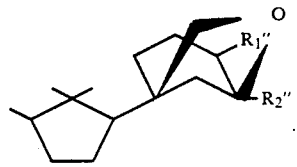

4. One or more compounds of claim 1 defined according to the structure:

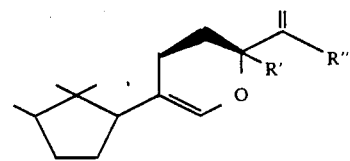

5. A mixture of compounds of claim 2 having the structures:

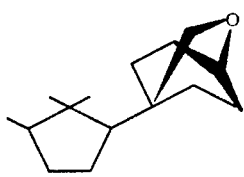

and

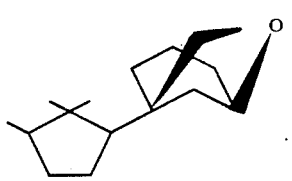

6. A mixture of compounds of claim 2 having the structures:

and

7. A compound of claim 4 having the structure:

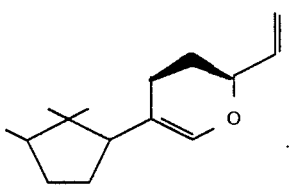

8. A mixture of compounds of claim 4 having the structures:

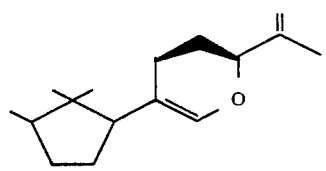

and

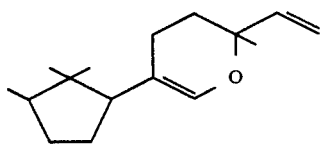

9. A process for augmenting or enhancing the aroma of a consumable material selected from the group consisting of perfume compositions, colognes and perfumed articles comprising the step of intimately admixing with a perfume base, a cologne base or a perfumed base, an aroma augmenting, enhancing or imparting quantity of at least one compound defined according to claim 1.

10. The process of claim 9 wherein the consumable material is a perfume composition.

11. The process of claim 9 wherein the consumable material is a cologne.

12. The process of claim 9 wherein the consumable material is a perfumed article and the perfumed article is a solid or liquid anionic, cationic, nonionic or zwitterionic detergent.

13. The process of claim 9 wherein the consumable material is a perfumed article and the perfumed article is a microporous polymer.

14. A perfume composition comprising a perfume base and intimately admixed therewith an aroma augmenting, enhancing or imparting quantity of at least one compound defined according to claim 1.

15. A cologne composition comprising water, ethyl alcohol and at least one compound defined according to claim 1.

16. A perfumed article comprising a perfumed article base and intimately admixed therewith an aroma augmenting, enhancing or imparting quantity of at least one compound defined according to claim 1.

17. A perfumed polymer comprising a microporous polymer and intimately admixed therewith in the interstices thereof an aroma augmenting, enhancing or imparting quantity of at least one compound defined according to claim 1.

* * * * *